US008404915B2

(12) United States Patent
McCullough et al.

(10) Patent No.: US 8,404,915 B2
(45) Date of Patent: Mar. 26, 2013

(54) PHOSPHINE LIGAND-METAL COMPOSITIONS, COMPLEXES, AND CATALYSTS FOR ETHYLENE TRIMERIZATIONS

(75) Inventors: Laughlin G. McCullough, League City, TX (US); Francis Charles Rix, League City, TX (US); John F. Walzer, Seabrook, TX (US); Lily Joy Ackerman, San Francisco, CA (US); Keith Anthony Hall, San Jose, CA (US); Gary Michael Diamond, Menlo Park, CA (US); Victor Oswaldo Nava-Salgado, Cupertino, CA (US)

(73) Assignee: ExxonMobil Chemical Patents Inc., Houston, TX (US)

(*) Notice: Subject to any disclaimer, the term of this patent is extended or adjusted under 35 U.S.C. 154(b) by 1060 days.

(21) Appl. No.: 11/844,562

(22) Filed: Aug. 24, 2007

(65) Prior Publication Data

US 2008/0058486 A1    Mar. 6, 2008

Related U.S. Application Data

(60) Provisional application No. 60/841,226, filed on Aug. 30, 2006.

(51) Int. Cl.
*C07C 2/22* (2006.01)
(52) U.S. Cl. ........ 585/513; 585/502; 585/510; 585/511; 585/512
(58) Field of Classification Search .............. 585/511, 585/512, 513, 521, 502, 510; 502/117, 103, 502/114
See application file for complete search history.

(56) References Cited

U.S. PATENT DOCUMENTS

| | | |
|---|---|---|
| 3,300,458 A | 1/1967 | Manyik et al. |
| 3,333,016 A | 7/1967 | Schultz |
| 4,472,525 A | 9/1984 | Singleton |
| 4,668,838 A | 5/1987 | Briggs |
| 4,689,437 A | 8/1987 | Murray |
| 4,777,315 A | 10/1988 | Levine et al. |
| 4,853,356 A | 8/1989 | Briggs |
| 5,137,994 A | 8/1992 | Goode et al. |
| 5,198,563 A | 3/1993 | Reagen et al. |
| 5,376,612 A | 12/1994 | Reagen et al. |
| 5,382,738 A | 1/1995 | Reagen et al. |
| 5,438,027 A | 8/1995 | Reagen et al. |
| 5,439,862 A | 8/1995 | Kemp |
| 5,451,645 A | 9/1995 | Reagen et al. |
| 5,491,272 A | 2/1996 | Tanaka et al. |
| 5,523,507 A | 6/1996 | Reagen et al. |
| 5,543,375 A | 8/1996 | Lashier et al. |
| 5,550,305 A | 8/1996 | Wu |
| 5,557,026 A | 9/1996 | Tanaka et al. |
| 5,563,312 A | 10/1996 | Knudsen et al. |
| 5,637,660 A | 6/1997 | Nagy et al. |
| 5,668,249 A | 9/1997 | Baardman et al. |
| 5,731,487 A | 3/1998 | Tamura et al. |
| 5,744,677 A | 4/1998 | Wu |
| 5,750,816 A | 5/1998 | Araki et al. |
| 5,750,817 A | 5/1998 | Tanaka et al. |
| 5,763,723 A | 6/1998 | Reagen et al. |
| 5,811,618 A | 9/1998 | Wu |
| 5,814,575 A | 9/1998 | Reagen et al. |
| 5,853,551 A | 12/1998 | Boucot et al. |
| 5,856,257 A | 1/1999 | Freeman et al. |
| 5,856,610 A | 1/1999 | Tamura et al. |
| 5,856,612 A | 1/1999 | Araki et al. |
| 5,859,303 A | 1/1999 | Lashier |
| 5,910,619 A | 6/1999 | Urata et al. |
| 5,919,996 A | 7/1999 | Freeman et al. |
| 5,968,866 A | 10/1999 | Wu |
| 6,004,256 A | 12/1999 | Townsend et al. |
| 6,031,145 A | 2/2000 | Commereuc et al. |
| 6,103,657 A | 8/2000 | Murray |
| 6,133,495 A | 10/2000 | Urata et al. |
| 6,136,748 A | 10/2000 | Smith |
| 6,137,748 A | 10/2000 | Murakami |
| 6,265,513 B1 | 7/2001 | Murray et al. |
| 6,268,447 B1 | 7/2001 | Murray et al. |
| 6,277,841 B1 | 8/2001 | Rajagopalan et al. |
| 6,303,719 B1 | 10/2001 | Murray et al. |
| 6,320,002 B1 | 11/2001 | Murray et al. |
| 6,320,005 B1 | 11/2001 | Murray |
| 6,337,297 B1 | 1/2002 | Mimura et al. |
| 6,344,594 B1 | 2/2002 | Sen et al. |
| 6,380,451 B1 | 4/2002 | Kreischer et al. |
| 6,437,161 B1 | 8/2002 | Mihan et al. |
| 6,455,648 B1 | 9/2002 | Freeman et al. |
| 6,489,263 B2 | 12/2002 | Murray et al. |

(Continued)

FOREIGN PATENT DOCUMENTS

| | | |
|---|---|---|
| CA | 2087578 | 7/1994 |
| CA | 2115639 | 9/1994 |

(Continued)

OTHER PUBLICATIONS

Carter et al., "High Activity Ethylene Trimerization Catalysts Based on Diphosphine Ligands", Chem. Commun., 2002, pp. 858-859.*
Theopold, et al., "Chromium: Organometallic Chemistry" in Encyclopedia of Inorganic Chemistry, 2006, John Wiley & Sons, available on-line Mar. 15, 2006.*
R.D. Kohn et al., 1,3,5-Triazacyclohexane Complexes of Chromium as Homogeneous Model Systems for the Phillips Catalyst, ACS Symposium Series, 2003, 857, pp. 88-100.
Hecheng Shuzhi Ji Suliao, China Synthetic Resin and Plastics, 2001, 18(2), 23-25, 43.
N. J. Robertson et al., "Chromium(II) and Chromium (III) Complexes Supported by Tris(2-pyridylmethyl)amine: Synthesis, Structures, and Reactivity," Inorg. Chem., 42, pp. 6876-6885 (2003).

(Continued)

*Primary Examiner* — In Suk Bullock
*Assistant Examiner* — Bradley Etherton
(74) *Attorney, Agent, or Firm* — Robert L. Abdon

(57) ABSTRACT

This invention relates to a method to selectively oligomerize olefins comprising contacting olefins with: 1) at least one diaryl-substituted diphosphine ligand; 2) a chromium metal precursor; and 3) optionally, one or more activators. In a particular embodiment, the method for selectively oligomerizing olefins includes trimerizing ethylene to selectively form 1-hexene.

25 Claims, No Drawings

U.S. PATENT DOCUMENTS

| | | | |
|---|---|---|---|
| 6,521,806 B1 | 2/2003 | Tamura et al. | |
| 6,583,083 B2 | 6/2003 | Murray et al. | |
| 6,610,627 B2 | 8/2003 | Murray | |
| 6,610,805 B1 | 8/2003 | Guram et al. | |
| 6,706,829 B2 | 3/2004 | Boussie et al. | |
| 6,713,577 B2 | 3/2004 | Boussie et al. | |
| 6,727,361 B2 | 4/2004 | LaPointe et al. | |
| 6,750,345 B2 | 6/2004 | Boussie et al. | |
| 6,800,702 B2 * | 10/2004 | Wass | 526/124.3 |
| 6,828,269 B2 | 12/2004 | Commereuc et al. | |
| 6,828,397 B2 | 12/2004 | Boussie et al. | |
| 6,844,290 B1 | 1/2005 | Maas et al. | |
| 6,844,920 B2 | 1/2005 | Louellau | |
| 6,900,152 B2 | 5/2005 | Yoshida et al. | |
| 7,214,842 B2 | 5/2007 | Mihan et al. | |
| 2001/0034297 A1 | 10/2001 | Murray et al. | |
| 2002/0035029 A1 | 3/2002 | Yoshida et al. | |
| 2002/0065379 A1 | 5/2002 | Murray | |
| 2002/0137845 A1 | 9/2002 | Boussie et al. | |
| 2002/0142912 A1 | 10/2002 | Boussie et al. | |
| 2002/0147288 A1 | 10/2002 | Boussie et al. | |
| 2002/0153697 A1 | 10/2002 | Amirola | |
| 2002/0156279 A1 | 10/2002 | Boussie et al. | |
| 2002/0173419 A1 | 11/2002 | Boussie et al. | |
| 2002/0177711 A1 | 11/2002 | LaPointe et al. | |
| 2002/0183574 A1 | 12/2002 | Dixon et al. | |
| 2003/0130551 A1 | 7/2003 | Drochon et al. | |
| 2003/0149198 A1 | 8/2003 | Small et al. | |
| 2003/0153697 A1 | 8/2003 | Boussie et al. | |
| 2003/0166456 A1 | 9/2003 | Wass | |
| 2004/0122247 A1 | 6/2004 | Boussie et al. | |
| 2004/0122271 A1 | 6/2004 | Van Zon et al. | |
| 2004/0228775 A1 | 11/2004 | Ewert et al. | |
| 2004/0236163 A1 | 11/2004 | Ewert et al. | |
| 2005/0020788 A1 | 1/2005 | Wass | |
| 2005/0020866 A1 | 1/2005 | Kobayashi et al. | |
| 2005/0113524 A1 | 5/2005 | Stevens et al. | |
| 2005/0113622 A1 * | 5/2005 | Drent et al. | 585/521 |
| 2005/0197521 A1 | 9/2005 | Kreischer | |
| 2006/0094839 A1 | 5/2006 | Diamond et al. | |
| 2006/0094867 A1 | 5/2006 | Diamond et al. | |
| 2006/0173226 A1 | 8/2006 | Blann et al. | |
| 2006/0211903 A1 | 9/2006 | Blann et al. | |
| 2006/0229480 A1 | 10/2006 | Blann et al. | |
| 2006/0235250 A1 * | 10/2006 | De Boer et al. | 585/502 |
| 2006/0247339 A1 | 11/2006 | Harashina et al. | |
| 2006/0247399 A1 | 11/2006 | McConville et al. | |
| 2006/0247483 A1 | 11/2006 | McConville et al. | |
| 2006/0293546 A1 | 12/2006 | Nabika | |
| 2007/0027350 A1 | 2/2007 | Nabika | |
| 2007/0185358 A1 | 8/2007 | Buchanan et al. | |
| 2007/0185364 A1 | 8/2007 | Buchanan et al. | |

FOREIGN PATENT DOCUMENTS

| | | |
|---|---|---|
| CN | 1256968 | 6/2000 |
| EP | 237 079 | 7/1990 |
| EP | 668 106 | 8/1995 |
| EP | 537 609 | 8/1996 |
| EP | 416 304 | 3/1997 |
| EP | 614 865 | 10/1997 |
| EP | 699 648 | 4/1998 |
| EP | 622 347 | 6/1998 |
| EP | 706 983 | 8/1998 |
| EP | 889 061 | 1/1999 |
| EP | 993 464 | 4/2000 |
| EP | 780 353 | 8/2000 |
| EP | 608 447 | 10/2001 |
| EP | 1 308 450 | 5/2003 |
| EP | 1 110 930 | 9/2003 |
| EP | 1 364 974 | 11/2003 |
| EP | 1 607 415 | 12/2005 |
| GB | 2 298 864 | 9/1996 |
| JP | 07010780 | 1/1995 |
| JP | 06515783 | 3/1995 |
| JP | 06515873 | 3/1995 |
| JP | 7215896 | 8/1995 |
| JP | 7267881 | 10/1995 |
| JP | 9020692 | 1/1997 |
| JP | 9020693 | 1/1997 |
| JP | 9268133 | 10/1997 |
| JP | 9268134 | 10/1997 |
| JP | 9268135 | 10/1997 |
| JP | 10007593 | 1/1998 |
| JP | 10007594 | 1/1998 |
| JP | 10007595 | 1/1998 |
| JP | 10007712 | 1/1998 |
| JP | 10036431 | 2/1998 |
| JP | 10036432 | 2/1998 |
| JP | 10045638 | 2/1998 |
| JP | 10087518 | 4/1998 |
| JP | 11092407 | 4/1999 |
| JP | 11092408 | 4/1999 |
| JP | 11222445 | 8/1999 |
| JP | 2000176291 | 6/2000 |
| JP | 2000202299 | 7/2000 |
| JP | 2000212212 | 8/2000 |
| JP | 2007-010780 | 1/2001 |
| JP | 2001009290 | 1/2001 |
| JP | 2001187345 | 7/2001 |
| JP | 2002045703 | 2/2002 |
| JP | 2002066329 | 3/2002 |
| JP | 2002102710 | 4/2002 |
| JP | 2002172327 | 6/2002 |
| JP | 2002200429 | 7/2002 |
| JP | 2002205960 | 7/2002 |
| JP | 2002233765 | 8/2002 |
| JP | 3351068 | 11/2002 |
| JP | 2003071294 | 3/2003 |
| JP | 3540827 | 7/2004 |
| JP | 3540828 | 7/2004 |
| JP | 3577786 | 10/2004 |
| WO | WO 97/37765 | 10/1997 |
| WO | WO 99/01460 | 1/1999 |
| WO | WO 99/19280 | 4/1999 |
| WO | WO 00/37175 | 6/2000 |
| WO | WO 00/50470 | 8/2000 |
| WO | WO 01/10876 | 2/2001 |
| WO | WO 01/47839 | 7/2001 |
| WO | WO 01/48028 | 7/2001 |
| WO | WO 01/68572 | 9/2001 |
| WO | WO 01/83447 | 11/2001 |
| WO | WO 02/04119 | 1/2002 |
| WO | WO 02/38628 | 5/2002 |
| WO | WO 02/46249 | 6/2002 |
| WO | WO 02/066404 | 8/2002 |
| WO | WO 02/066405 | 8/2002 |
| WO | WO 02/083306 | 10/2002 |
| WO | WO 03/004158 | 1/2003 |
| WO | WO 03/053890 | 7/2003 |
| WO | WO 03/053891 | 7/2003 |
| WO | WO 2004/056477 | 7/2004 |
| WO | WO 2004/056478 | 7/2004 |
| WO | WO 2004/056479 | 7/2004 |
| WO | WO 2004/056480 | 7/2004 |
| WO | WO 2004056477 A1 * | 7/2004 |
| WO | WO 2004056478 A1 * | 7/2004 |
| WO | WO 2004/083263 | 9/2004 |
| WO | WO 2005/123633 | 12/2005 |
| WO | WO 2005/123884 | 12/2005 |
| WO | WO 2006/096881 | 9/2006 |
| WO | WO 2007/007272 | 1/2007 |

OTHER PUBLICATIONS

Kohn et al., Triazacyclohexane complexes of chromium as highly active homogeneous model sytstems for the Philips catalyst, Chem. Commun., 2000, pp. 1927-1928.

P.J.W. Deckers et al., "Catalytic Trimerization of Ethene with Highly Active Cyclopentadienyl-Arene Titanium Catalysts," Organometallics, 2002; 21, pp. 5122-5135.

S. Naqvi, "1-Hexene From Ethylene by the Phillips Trimerization Technology," available on-line at http://www.sriconsulting.com/PEP/Reports/Phase_95/RW95-1-1/RW95-1-8.html, Dec. 1997.

A. Ranwell et al., "Potential Application of Ionic Liquids for Olefin Oligomerization,"ACS Symposium Series, Chapter 12, 2002, 818, pp. 147-160.

K.R. Dunbar et al., "Structure of [HTMPP] 3W2CL9[HTMPP=Tris(2,4,6-trimethoxyphenyl)-phosphonium]," Acta Cryst., 1991, C47, pp. 23-26.

D.H. Morgan et al., "The Effect of Aromatic Ethers on the Trimerisation of Ethylene using a CHromium Catalyst and Aryloxy Ligands," Adv. Synth. & Catalysis, 2003, 345, pp. 939-942.

Agapie et al.; "A Chromium-Diphosphine System for Catalytic Ethylene Trimerization: Synthetic and Structural Studies of Chromium Complexes with a Nitrogen-Bridged Diphosphine Ligand with ortho-Methoxyaryl Substituents"; Organometallicas, 25(11); 2006, pp. 2733-2742.

Y.Yang et al., "Roles of chloro compound in homogeneous [Cr(2-ethylhexanoate)3/2,5-dimethylpyrrole/triethylaluminum/chloro compound] catalyst system for ethylene trimerization," Applied Catalysis A: General, 2000, 193, pp. 29-38.

H. Mahomed et al., "Ethylene trimerisation catalyst based on substituted cyclopentadienes," Applied Catalysis A: General, 2003, 255, pp. 355-359.

A. Carter et al., "High activity ethylene trimerisation catalysts based on diphosphine ligands," Chem. Commun., 2002, 8, pp. 858-859.

D.S. McGuinness et al., "Novel Cr-PNP complexes as catalysts for the trimerisation of ethylene," Chem. Commun. 2003, 3, pp. 334-335.

K. Blann et al., "Highly selective chromium-based ethylene trimerisation catalysts with bulky diphosphinoamine ligands," Chem. Commun., 2005, pp. 620-621.

M.J. Overett et al., "Ethylene trimerisation and tetramerisation catalysts with polar-substituted diphosphinoamine ligands," Chem. Commun., 2005, pp. 622-624.

C.N. Nenu et al., "Single-site heterogeneous Cr-based catalyst for the selective timerisation of ethylene," Chem. Commun., 2005, pp. 1865-1867.

T. Imamoto et al., "Synthesis and reactions of Optically Pure Cyclohexyl (o-methoxyphenyl) phosphine-Borane and t-Butyl-(o-methoxyphenyl)phosphine-Borane," Heteroatom Chemistry, 1993,vol. 4, No. 5, pp. 475-486.

L. Hirsivaara et al., "M(CO)6 (M=Cr, Mo, W) derivatives of (o-anisyl)diphenylphosphine, bis(o-anisyl)phenylphosphine tris(o-anisyl)phosphine and (p-anisyl)bis(o-anisyl)phosphine," Inorganics Chimica ACTA, 2000, 307(1-2), pp. 47-56.

A. Ariffin et al., "The asymmetric synthesis of phosphorus- and sulfur-containing tricarbonyl(n6-arcne)chromium complexes using the chiral base approach," J. Chem. Soc., Perkin Trans., 1, 1999, pp. 3177-3189.

C. Andes et al., "New Tantalum-based Catalyst System for the Selective Trimerization of ethene to 1-Hexene," J. Am. Chem. Soc., 2001, 123, pp. 7423-7424.

D.S. McGuinness et al., "First Cr(III)-SNS Complexes and Their Use as Highly Efficient Catalysts for the Trimerization of Ethylene to 1-Hexene," J. Am .Chem. Soc., 2003, 125, pp. 5272-5273.

T.Agapie et al., "Mechanistic Studies of the Ethylene Trimerization Reaction with Chromium-Diphosphine Catalysts: Experimental Evidence for a mechanism Involving Metallacyclic Intermediates," J. Am. Chem. Soc., 126, 2004, pp. 1304-1305.

A. Bollmann et al., "Ethylene Tetramerization: A New Route to Produce 1-Octene in Exceptionally High Selectivities," J. Am. Chem. Soc., 126, 2004, pp. 14712-14713.

T. Monoi et al., "Silica-supported Cr{N(SiMe3)2]3/ isobutylalumoxane catalyst for selective ethylene trimerization," Journal of Mol. Catalysis A: Chemical, 187, 2002, pp. 135-141.

R.M. Manyuk et al., "A Soluble Chromium-Based Catalyst for Ethylene Trimerization and Polymerization," Journal of Catalysis, 1977, 47, pp. 197-209.

J. Pietsch et al., "Koordinationschemie funktioneller Phosphine II. Carbonyl(nitrosyl) wolfram-Komplexe mit 2-Diphenylphosphphinoanisol sowie 2-Diphenylphosphinoanilid, -benzoat und—phenolat als Liganden," Journal of Organometallic Chemistry, 495, 1995, pp. 113-125.

L. Hirsivaara et al., "Organometallic derivatives of multidentate phosphines [o-(methylthio)phenyl]diphenylphosphine and bis(o-(methylthio)phenyl(phenylphosphine: preparation and characterization of group 6 metal carbonyl derivatives," Journal of Organometallic Chemistry, 579, 1999, pp. 45-52.

L. Dahlenburg et al., "Koordinationschemie funktioneller Phosphane VIII. Tetracarbonylkomplexe des Wolframs und Molybdans mit 2-(Diphenylphosphanyl)anilin-Liganden," Journal of Organometallic Chemistry, 585, 1999, pp. 225-233.

J.T. Dixon et al., "Advances in selective ethylene trimezisation—a critical overview," Journal of Organometallic Chemistry, 689, 2004, pp. 3641-3668.

D. de Wet-Roos et al., "Homogeneous Tandem Caatalysis of Bis(2-decylthioethyl)amine-Chromium Trimerization Catalyst in Combination with Metallocene Catalysts," Macromolecules, 2004, 37, pp. 9314-9320.

R. Blom et al., "1,3,5-Triazacyclohexane Complexes of Chromium as Homogeneous Model Systems for the Phillips Catalyst," Organometallic Catalysts and Olefin Polymerization, 2001, pp. 147-155.

K. Burgess, Stereochemically Matched (and Mismatched) Bisphosphine Ligands: DIOP-DIPAMP Hybrids, Organometallics, 1992, 11, pp. 3588-3600.

K.R. Dunbar et al., Carbon Monoxide Reactions of the Fluxional Phosphine Complex (n3-PR3)Mo(CO)3 (R=2,4,6-Trimethoxyphenyl), Organometallics, 1994, 13, pp. 2713-2720.

G. Boni et al., "Heterobimetallic Dibridged Complexes [Cp2Ta(u-CO)(u-PMe2)M'(CO)4] (M'=Cr, W): Synthesis and Reactivity toward Two-Electron Donor Ligands L (L=PR3, Me2P(CH2)nPMe2, CNR)," Organometallics, 1995, 14, pp. 5652-5656.

R.L. Wife et al., "Phosphine Oxide Anions in the Synthesis of Phosphine Ligands," Synthesis, 1983, 1, pp. 71-73.

R. Agrawal "*More Operable Fully Thermally Coupled Distillation Column Configurations for Multicompoent Distillation*", Transactions of the Institution of Chemical Engineers, 1999, 77(A) pp. 543-553.

Y. T. Shah, et al. "*Design Parameters Estimations for Bubble Column Reactors*", American Institute of Chemical Engineers' Journal, 1982, vol. 28 No. 3, pp. 353-379.

K.M. Sundaram, et al. "*Ethylene*" Kirk-Othmer Encyclopedia of Chemical Technology, John Wiley, 2001, vol. 10, pp. 593-632, posted on-line Apr. 16, 2001.

B. L. Small et al., "New Chromium Complexes for Ethylene Oligomerization: Extended Use of Tridentate Ligands in Metal-Catalyzed Olefin Polymerization," Macromolecules, vol. 37, No. 12, 2004, pp. 4375-4386.

* cited by examiner

PHOSPHINE LIGAND-METAL COMPOSITIONS, COMPLEXES, AND CATALYSTS FOR ETHYLENE TRIMERIZATIONS

CROSS REFERENCE TO RELATED APPLICATIONS

This application claims priority to U.S. Provisional Patent Application No. 60/841,226, filed Aug. 30, 2006, the disclosures of which are incorporated by reference.

FIELD OF THE INVENTION

This invention relates to a process to oligomerize olefins using catalysts comprising di-phosphine ligands and oligomers produced therefrom. Specifically this invention relates to the trimerization of ethylene to prepare 1-hexene.

BACKGROUND OF THE INVENTION

The oligomerization of ethylene typically returns a broad distribution of 1-olefins having an even number of carbon atoms ($C_4$, $C_6$, $C_8$, $C_{10}$, etc.). These products range in commercial value, of which 1-hexene may be the most useful, as it is a comonomer commonly used in the production of commercial ethylene based copolymers.

Several catalysts useful for the oligomerization of olefin monomers have been developed, including the trimerization of ethylene. Several of these catalysts use chromium as a metal center. For example, U.S. Pat. No. 4,668,838, assigned to Union Carbide Chemicals and Plastics Technology Corporation, discloses a chromium catalyst complex formed by contacting a chromium compound with hydrolyzed hydrocarbyl aluminum and a donor ligand such as hydrocarbyl isonitriles, amines, and ethers. U.S. Pat. No. 5,137,994 discloses a chromium catalyst formed by the reaction products of bistriarylsilyl chromates and trihydrocarbylaluminum compounds.

U.S. Pat. No. 5,198,563 and related patents, issued to Phillips Petroleum Company, disclose chromium-containing catalysts containing monodentate amide ligands. A chromium catalyst complex formed by contacting an aluminum alkyl or a halogenated aluminum alkyl and a pyrrole-containing compound prior to contacting with a chromium containing compound is disclosed in U.S. Pat. Nos. 5,382,738, 5,438,027, 5,523,507, 5,543,375, and 5,856,257. Similar catalyst complexes are also disclosed in EP 0 416 304 B1, EP 0 608 447 B1, EP 0 780 353 B1, and CA2087578.

Several patents assigned to Mitsubishi Chemicals also disclose chromium catalyst complexes formed from a chromium compound, a pyrrole ring-containing compound, an aluminum alkyl, and a halide containing compound, including U.S. Pat. Nos. 5,491,272, 5,750,817, and 6,133,495. Other catalyst complexes are formed by contacting a chromium compound with a nitrogen containing compound such as a primary or secondary amine, amide, or imide, and an aluminum alkyl, as disclosed in U.S. Pat. Nos. 5,750,816, 5,856,612, and 5,910,619.

EP 0 537 609 discloses a chromium complex containing a coordinating polydentate ligand and an aluminoxane. Similarly, CA2115639 discloses a polydentate phosphine ligand.

EP 0 614 865 B1, issued to Sumitomo Chemical Co., Ltd., discloses a catalyst prepared by dissolving a chromium compound, a heterocyclic compound having a pyrrole ring or an imidazole ring, and an aluminum compound. EP 0 699 648 B1 discloses a catalyst obtained by contacting chromium containing compound with a di- or tri-alkyl aluminum hydride, a pyrrole compound or a derivative thereof, and a group 13 (III B) halogen compound.

WO03/053890, and McGuinness et al., *J. Am. Chem. Soc.* 125, 5272-5273, (2003), disclose a chromium complex of tridentate phosphine ligands and methylalumoxane (MAO) cocatalyst. However, due to serious drawbacks in the preparation of the phosphine-containing system, the use of a thioether donor group to replace the phosphorus donor in the ligands was also investigated.

WO02/083306A2 discloses a catalyst formed from a chromium source, a substituted phenol, and an organoaluminum compound. WO03/004158A2 discloses a catalyst system which includes a chromium source and a ligand comprising a substituted five membered carbocyclic ring or similar derivatives.

U.S. Pat. No. 5,968,866 discloses a catalyst comprising a chromium complex which contains a coordinating asymmetric tridentate phosphane, arsane, or stibane ligand (hydrocarbyl groups) and an aluminoxane. Similarly, WO02/04119A1 discloses a catalyst comprising a source of chromium, molybdenum, or tungsten, and a ligand containing at least one phosphorus, arsenic, or antimony atom bound to at least one (hetero)hydrocarbyl group.

Japanese patent application JP 2001187345A2 (Tosoh Corp., Japan) discloses ethylene trimerization catalysts comprising chromium complexes having ligands which are amines substituted with two (pyrazol-1-yl)methyl groups.

Further U.S. Pat. No. 6,800,702 (and related WO 2002/04119, US 2003/166456, and US 2005/020788) disclose olefin trimerization catalysts represented by the formula $(R^1)(R^2)X$—Y—$X(R^3)(R^4)$ where $R^1$, $R^2$, $R^3$ and $R^4$ may be, among other things, phenyl groups or methoxyphenyl groups, and X may be phosphorus, arsenic or antimony, and Y is a bridging group and may be, among other things, a hydrocarbyl, heterocarbyl, substituted hydrocarbyl, substituted heterohydrocarbyl or an inorganic bridging group. Most of the examples reported in U.S. Pat. No. 6,800,702 use (2-methoxyphenyl)$_2$PN(Me)P(2-methoxyphenyl)$_2$ in combination with $CrCl_3$ or $Cr(p-tolyl)Cl_2(THF)_3$ activated with methylalumoxane to prepare various mixtures of oligomerized ethylene. Comparative Example A, which is reported to produce no product, combined 1,2-bis(diphenylphosphino)ethane with methylalumoxane and ethylene. Likewise, Carter et al., *Chem. Commun.,* 2002, pp. 858-859 disclosed an ethylene trimerization catalyst obtained by contacting a chromium source, ligands bearing ortho-methoxy-substituted aryl groups, and an alkyl aluminoxane activator. Carter et al., also disclosed however in runs 18 and 19 that certain compounds produced no product. One of these ligands was (ortho-methoxyphenyl)$_2$P—$CH_2$—$CH_2$—P (ortho-methoxyphenyl)$_2$ also referred to as ligand 7 or 1,2-bis[(2-methoxyphenyl)phenylphosphino]ethane. In explaining this data, Carter et al speculated that "[t]his has lead us to hypothesize that the potential for ortho-methoxy groups to act as pendant donors and increase the coordinative saturation of the chromium centre is an important factor. Building on this hypothesis ligands 6 and 7, which contain the same aryl substitution pattern as [ligand] 1 but different chelate backbones, were tested but both proved to be inactive. Clearly the ligand backbone also plays an important role." (Chem. Comm., 2002 pg 859.)

Other references of interest include *J. Am. Chem. Soc.* 123, 7423-7424 (2001), WO01/68572A1, WO02/066404A1, WO04/056477, WO04/056478, WO04/056479, WO04/056480, WO01/10876, WO97/37765, EP1110930A1, U.S. Pat. No. 3,333,016, U.S. Pat. No. 5,439,862, U.S. Pat. No.

5,744,677, U.S. Pat. No. 6,344,594, U.S. Pat. No. 4,689,437, U.S. Pat. No. 4,472,525, U.S. Pat. No. 5,668,249, U.S. Pat. No. 5,856,610, U.S. Pat. No. 3,300,458, U.S. Pat. App. Pub. No. 2002/0035029A1, *Journal of Organometallic Chemistry* 579 (1999) 45-52, *Organometallics* 1992, 11 3588-3600, *Organometallics* 1995, 14, 5652-5656, *J. Chem. Soc., Perkin Trans.* 1, 1999, 3177-3189, *Organometallics* 1994, 13, 2713-2720, *Journal of Organometallic Chemistry*, Volume 585, Issue 2, 15 Aug. 1999, pgs 225-233, *Acta Cryst.* (1991). C47, 23-26, *Journal of Organometallic Chemistry*, Vol 495, No. 1, 14 Jun. 1995, pgs 113-125, *Inorg. Chim. ACTA* (2000), 307 (1-2), 47-56. *Chem. Commun.* 2005, 620-621, *Chem. Commun.* 2005, 622-624, *Chem. Commun.* 2005, 1865-1867, *J. Am. Chem. Soc.* 2004, 126, 14712-14713, *J. Am. Chem. Soc.* 2004, 126, 1304-1305, *Macromolecues*, 2004, 37, 9314-9320, *Journal of Organometallic Chemistry*, 2004, 689, 3641-3668.

Still other references of interest include *Heteroatom Chemistry*, 1993, 4, 475-486; *Synthesis*, 1983, 1, 71-73; U.S. Pat. No. 6,800,702; *Chem. Commun.*, 2002, 8, 858-859; *PERP Report*, Nexant/Chem Systems, 2004, 57-60; *Dangadi Shiyou Shihu*, 2002, 10, 25-29; *ACS Symposium Series*, 2002, 818, 147-160; *Journal of Organometallic Chemistry*, 2004689, 3641-3668; U.S. Pat. No. 4,668,838; U.S. Pat. No. 4,777,315; U.S. Pat. No. 4,853,356; U.S. Pat. No. 5,744,677; EP-608447; U.S. Pat. No. 5,557,026; JP06515873; U.S. Pat. No. 5,750,817; U.S. Pat. No. 5,731,487; EP-622347; U.S. Pat. No. 5,376,612; U.S. Pat. No. 5,382,738; JP3540827 B2; JP3540828 B2; JP3351068 B2; U.S. Pat. No. 5,563,312; JP07215896; JP07267881; U.S. Pat. No. 6,521,806; EP-706983; U.S. Pat. No. 5,523,507; U.S. Pat. No. 5,910,619; U.S. Pat. No. 5,550,305; U.S. Pat. No. 5,750,816; GB2298864; JP3577786 B2; JP09020692; JPO9020693; U.S. Pat. No. 5,859,303; U.S. Pat. No. 5,856,612; U.S. Pat. No. 6,133,495; JP09268133; JP09268134; JP09268135; JP10007593; JP10007594; JP10007595; JP10036431; JP10036432; JP10045638; JP10087518; U.S. Pat. No. 5,763,723; U.S. Pat. No. 5,811,618; U.S. Pat. No. 5,814,575; U.S. Pat. No. 6,031,145; U.S. Pat. No. 5,856,257; JP11092407; JP11092408; US2004228775; U.S. Pat. No. 5,919,996; JP11222445; U.S. Pat. No. 5,968,866; U.S. Pat. No. 6,610,805; CN1256968; JP2000176291; JP2000202299; U.S. Pat. No. 6,337,297; JP2000212212; JP2001009290; US2002183574; U.S. Pat. No. 6,828,269; WO200147839 U.S. Pat. No. 6,455,648; WO200183447; JP2002045703; JP2002066329; JP2002102710; US2002035029; JP2002172327; JP2002200429; JP2002233765; WO200283306; WO2003004158; JP2002205960; US2003130551; WO2003053890; WO2003053891; JP2003071294; US2003149198; US2004122271; WO2004056479; WO2004056478; WO2004083263; *Journal of Catalysis*, 1977, 47, 197-209; *J. Am. Chem. Soc.*, 1989, 11, 674-675; *Applied Catalysis, A* (General) 2000, 193, 29-38; *Hecheng Shuzhi Ji Suliao*, 2001, 18, 23-25, 43; *Organometallic Catalysts and Olefin Polymerization*, 2001, 147-155; *J. Mol. Catalysis. A: Chemical* (2002), 187, 135-141; *J. Am. Chem. Soc.*, 2002, 125, 5272-5273; *Chem. Commun.* 2003, 3, 334-335; *Beijing Huagong Daxue Xuebao, Ziran Kexueban*, 2003, 30, 80-82; *Adv. Synth. & Catalysis*, 2003, 345, 939-942; *Applied Catalysis, A: General*, 2003, 255, 355-359; *J. Am. Chem. Soc.* 2004, 126, 1304-1305; *ACS Symposium Series*, 2003, 857 (Beyond Metallocenes), 88-100; and *J. Am. Chem. Soc.*, 2004, 126, 14712-14713.

Although each of the above described catalysts is useful for the trimerization of ethylene, there remains a desire to improve the performance of olefin oligomerization catalysts from the standpoint of productivity and selectivity for oligomers such as 1-hexene and or 1-octene.

SUMMARY OF THE INVENTION

This invention relates to methods to selectively oligomerize olefins, compositions to accomplish the oligermization, ligands to prepare the compositions, methods to prepare the ligands, compositions and complexes. In general, the olefins are contacted with a composition comprising:

1) at least one ligand characterized by the general formula:

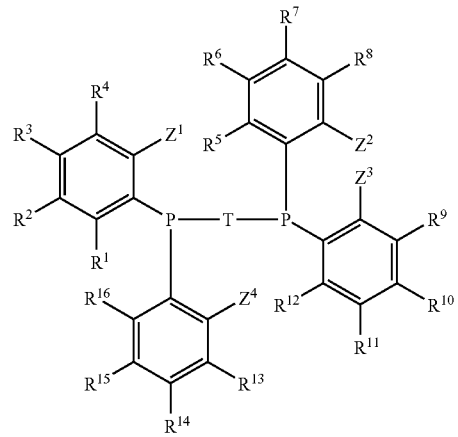

wherein
P is phosphorus;
each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$ and $R^{16}$ is, independently, selected from the group consisting of hydrogen, halogen, optionally substituted hydrocarbyl and optionally substituted heteroatom containing hydrocarbyl;
each of $Z^1$, $Z^2$, $Z^3$, and $Z^4$ is, independently, selected from a first group consisting of hydrogen, a hydrocarbyl, alkoxy, aryloxy, alkylthio, arylthio, hydroxyl, mercapto and amino;
T is a bridging group selected from the group consisting of optionally substituted hydrocarbyl having from 2 to 20 carbon atoms;

2) a metal precursor characterized by the general formula $Cr(L)_n$ where each L is independently selected from the group consisting of halide, alkyl, substituted alkyl, cycloalkyl, substituted cycloalkyl, heteroalkyl, substituted heteroalkyl heterocycloalkyl, substituted heterocycloalkyl, aryl, substituted aryl, heteroaryl, substituted heteroaryl, alkoxy, aryloxy, hydroxy, boryl, silyl, amino, amine, hydrido, allyl, diene, seleno, phosphino, phosphine, ether, thioether, carboxylates, thio, 1,3-dionates, oxalates, carbonates, nitrates, sulfates, ethers, thioethers and combinations thereof, and wherein two or more L groups may be combined in a ring structure having from 3 to 50 non-hydrogen atoms; n is 1, 2, 3, 4, 5, or 6; and 3) optionally, one or more activators,
and wherein at least one of the following conditions are satisfied:
a) at least two and less than all four of $Z^1$, $Z^2$, $Z^3$, and $Z^4$ are selected from a second group consisting of alkoxy, aryloxy, alkylthio, arylthio, hydroxyl, mercapto, and amino, and $Z^1$, $Z^2$, $Z^3$, and $Z^4$ may not all be methoxy, and either of the pairs of $Z^1$ and $Z^2$ or $Z^3$ and $Z^4$ are not both selected from the second group; and
b) when $Z^1$, $Z^2$, $Z^3$, and $Z^4$ are each methoxy and T is an ethylene or methylene bridge, the metal precursor is not $CrCl_3(THF)_3$, where THF is tetrahydrofuran.

In one embodiment, T can be a hydrocarbyl bridge formed by an aryl or cycloalkyl group. For example, such aryl or cycloalkyl bridging groups include phenyl, naphthyl, biphenyl and cyclohexyl. In certain embodiments, the phosphorus atoms are connected apart from each other by two, three, four, five or six carbon bonds. For example, when a phenyl or cyclohexyl group is T, the phosphorus atoms can be attached 1, 2 or 1, 3 or 1, 4 relative to each other (ortho, meta or para).

Further aspects of this invention will be evident to those of skill in the art upon review of this specification.

DETAILED DESCRIPTION OF THE INVENTION

For the purposes of this invention and the claims thereto when an oligomeric material (such as a dimer, trimer, or tetramer) is referred to as comprising an olefin, the olefin present in the material is the reacted form of the olefin. Likewise, the active species in a catalytic cycle may comprise the neutral or ionic forms of the catalyst. In addition, a reactor is any container(s) in which a chemical reaction occurs.

As used herein, the new numbering scheme for the Periodic Table Groups is used as set out in CHEMICAL AND ENGINEERING NEWS, 63(5), 27 (1985).

As used herein, the term "independently selected" is used herein to indicate that the groups in question—e.g. $R^1, R^2, R^3, R^4$, and $R^5$—can be identical or different (e.g., $R^1, R^2, R^3, R^4$, and $R^5$ may all be alkyls, or $R^1$ and $R^2$ may be an alkyl and $R^3$ may be an aryl, etc.). Use of the singular includes use of the plural and vice versa (e.g., a hexane solvent, includes hexanes). A named R group will generally have the structure that is recognized in the art as corresponding to R groups having that name. The terms "compound" and "complex" are generally used interchangeably in this specification, but those of skill in the art may recognize certain compounds as complexes and vice versa. In addition, the term "catalyst" will be understood by those of skill in the art to include either activated or unactivated forms of the molecules that comprise the catalyst, for example, a procatalyst, and including complexes and activators or compositions of ligands, metal precursors and activators and optionally including scavengers and the like. For purposes of this invention, a catalyst system is defined to be a metal ligand complex and an optional activator. A metal ligand complex is defined to be the product of the combination of a metal precursor and a ligand. Preferably the catalyst system is a combination of a metal ligand complex and an activator. For the purposes of illustration, representative certain groups are defined herein. These definitions are intended to supplement and illustrate, not preclude, the definitions known to those of skill in the art.

"Optional" or "optionally" means that the subsequently described event or circumstance may or may not occur, and that the description includes instances where the event or circumstance occurs and instances where it does not. For example, the phrase "optionally substituted hydrocarbyl" means that a hydrocarbyl moiety may or may not be substituted and that the description includes both unsubstituted hydrocarbyl and hydrocarbyl where there is substitution.

The term "substituted" as in "substituted hydrocarbyl," "substituted aryl," "substituted alkyl," and the like, means that in the group in question (i.e., the hydrocarbyl, alkyl, aryl or other moiety that follows the term), at least one hydrogen atom bound to a carbon atom is replaced with one or more substituent groups such as hydroxy, alkoxy, alkylthio, phosphino, amino, halo, silyl, and the like. When the term "substituted" introduces a list of possible substituted groups, it is intended that the term apply to every member of that group. That is, the phrase "substituted alkyl, alkenyl and alkynyl" is to be interpreted as "substituted alkyl, substituted alkenyl and substituted alkynyl." Similarly, "optionally substituted alkyl, alkenyl and alkynyl" is to be interpreted as "optionally substituted alkyl, optionally substituted alkenyl and optionally substituted alkynyl." Further the term "substituted heteroatom" means that at least at least one hydrogen atom bound to the heteroatom atom is replaced with one or more substituent groups such as hydrocarbyl, hydroxy, alkoxy, alkylthio, phosphino, amino, halo, silyl, and the like.

The term "saturated" refers to the lack of double and triple bonds between atoms of a radical group such as ethyl, cyclohexyl, pyrrolidinyl, and the like. The term "unsaturated" refers to the presence of one or more double and triple bonds between atoms of a radical group such as vinyl, allyl, acetylide, oxazolinyl, cyclohexenyl, acetyl and the like, and specifically includes alkenyl and alkynyl groups, as well as groups in which double bonds are delocalized, as in aryl and heteroaryl groups as defined below.

The terms "cyclo" and "cyclic" are used herein to refer to saturated or unsaturated radicals containing a single ring or multiple condensed rings. Suitable cyclic moieties include, for example, cyclopentyl, cyclohexyl, cyclooctenyl, bicyclooctyl, phenyl, napthyl, pyrrolyl, furyl, thiophenyl, imidazolyl, and the like. In particular embodiments, cyclic moieties include between 3 and 200 atoms other than hydrogen, between 3 and 50 atoms other than hydrogen or between 3 and 20 atoms other than hydrogen.

The term "hydrocarbyl" as used herein refers to hydrocarbyl radicals containing 1 to about 50 carbon atoms, specifically 1 to about 24 carbon atoms, most specifically 1 to about 16 carbon atoms, including branched or unbranched, cyclic or acyclic, saturated or unsaturated species, such as alkyl groups, alkenyl groups, aryl groups, and the like.

The term "alkyl" as used herein refers to a branched or unbranched saturated hydrocarbon group typically although not necessarily containing 1 to about 50 carbon atoms, such as methyl, ethyl, n-propyl, isopropyl, n-butyl, isobutyl, sec-butyl, t-butyl, octyl, decyl, and the like, as well as cycloalkyl groups such as cyclopentyl, cyclohexyl and the like. Generally, although again not necessarily, alkyl groups herein may contain 1 to about 20 carbon atoms.

The term "alkenyl" as used herein refers to a branched or unbranched, cyclic or acyclic hydrocarbon group typically, although not necessarily, containing 2 to about 50 carbon atoms and at least one double bond, such as ethenyl, n-propenyl, isopropenyl, n-butenyl, isobutenyl,
octenyl, decenyl, and the like. Generally, although again not necessarily, alkenyl groups herein contain 2 to about 20 carbon atoms.

The term "alkynyl" as used herein refers to a branched or unbranched, cyclic or acyclic hydrocarbon group typically although not necessarily containing 2 to about 50 carbon atoms and at least one triple bond, such as ethynyl, n-propynyl, isopropynyl, n-butynyl, isobutynyl, octynyl, decynyl, and the like. Generally, although again not necessarily, alkynyl groups herein may have 2 to about 20 carbon atoms.

The term "aromatic" is used in its usual sense, including unsaturation that is essentially delocalized across several bonds around a ring. The term "aryl" as used herein refers to a group containing an aromatic ring. Aryl groups herein include groups containing a single aromatic ring or multiple aromatic rings that are fused together, linked covalently, or linked to a common group such as a methylene or ethylene moiety. More specific aryl groups contain one aromatic ring or two or three fused or linked aromatic rings, e.g., phenyl, naphthyl, biphenyl, anthracenyl, or phenanthrenyl. In particular embodiments, aryl substituents include 1 to about 200 atoms other than hydrogen, typically 1 to about 50 atoms other than hydrogen, and specifically 1 to about 20 atoms other than hydrogen. In some embodiments herein, multi-ring moieties are substituents and in such embodiments the multi-ring moiety can be attached at an appropriate atom. For example, "naphthyl" can be 1-naphthyl or 2-naphthyl; "anthracenyl" can be 1-anthracenyl, 2-anthracenyl or 9-anthracenyl; and "phenanthrenyl" can be 1-phenanthrenyl, 2-phenanthrenyl, 3-phenanthrenyl, 4-phenanthrenyl, or 9-phenanthrenyl.

The term "alkoxy" as used herein intends an alkyl group bound through a single, terminal ether linkage; that is, an "alkoxy" group may be represented as:

—O-alkyl where alkyl is as defined above. The term "aryloxy" is used in a similar fashion, and may be represented as —O-aryl, with aryl as defined herein. The term "hydroxy" refers to —OH.

Similarly, the term "alkylthio" as used herein intends an alkyl group bound through a single, terminal thioether linkage; that is, an "alkylthio" group may be represented as —S-alkyl where alkyl is as defined above. The term "arylthio" is used similarly, and may be represented as —S-aryl, with aryl as defined below. The term "mercapto" refers to —SH.

The terms "halo" and "halogen" are used in the conventional sense to refer to a chloro, bromo, fluoro or iodo radical.

The terms "heterocycle" and "heterocyclic" refer to a cyclic radical, including ring-fused systems, including heteroaryl groups as defined below, in which one or more carbon atoms in a ring is replaced with a heteroatom—that is, an atom other than carbon, such as nitrogen, oxygen, sulfur, phosphorus, boron or silicon. Heterocycles and heterocyclic groups include saturated and unsaturated moieties, including heteroaryl groups as defined below. Specific examples of heterocycles include pyridine, pyrrolidine, pyrroline, furan, tetrahydrofuran, thiophene, imidazole, oxazole, thiazole, indole, and the like, including any isomers of these. Additional heterocycles are described, for example, in Alan R. Katritzky, *Handbook of Heterocyclic Chemistry*, Pergammon Press, 1985, and in *Comprehensive Heterocyclic Chemistry*, A. R. Katritzky et al., eds., Elsevier, 2d. ed., 1996. The term "metallocycle" refers to a heterocycle in which one or more of the heteroatoms in the ring or rings is a metal.

The term "heteroaryl" refers to an aryl radical that includes one or more heteroatoms in the aromatic ring. Specific heteroaryl groups include groups containing heteroaromatic rings such as thiophene, pyridine, pyrazine, isoxazole, pyrazole, pyrrole, furan, thiazole, oxazole, imidazole, isothiazole, oxadiazole, triazole, and benzo-fused analogues of these rings, such as indole, carbazole, benzofuran, benzothiophene and the like.

More generally, the modifiers "hetero" and "heteroatom-containing", as in "heteroalkyl" or "heteroatom-containing hydrocarbyl group" refer to a molecule or molecular fragment in which one or more carbon atoms is replaced with a heteroatom. Thus, for example, the term "heteroalkyl" refers to an alkyl substituent that is heteroatom-containing. When the term "heteroatom-containing" introduces a list of possible heteroatom-containing groups, it is intended that the term apply to every member of that group. That is, the phrase "heteroatom-containing alkyl, alkenyl and alkynyl" is to be interpreted as "heteroatom-containing alkyl, heteroatom-containing alkenyl and heteroatom-containing alkynyl."

By "divalent" as in "divalent hydrocarbyl", "divalent alkyl", "divalent aryl" and the like, is meant that the hydrocarbyl, alkyl, aryl or other moiety is bonded at two points to atoms, molecules or moieties with the two bonding points being covalent bonds.

As used herein the term "silyl" refers to the —SiQ$^1$Q$^2$Q$^3$ radical, where each of Q$^1$, Q$^2$, and Q$^3$ is independently selected from the group consisting of hydrogen and optionally substituted alkyl, alkenyl, alkynyl, heteroatom-containing alkyl, heteroatom-containing alkenyl, heteroatom-containing alkynyl, aryl, heteroaryl, alkoxy, aryloxy, amino, silyl and combinations thereof.

As used herein the term "boryl" refers to the -BQ$^1$Q$^2$ group, where each of Q$^1$ and Q$^2$ is as defined above. As used herein, the term "phosphino" refers to the group —PQ$^1$Q$^2$, where each of Q$^1$ and Q$^2$ is as defined above. As used herein, the term "phosphine" refers to the group: pQ$^1$Q$^2$Q$^3$, where each of Q$^1$, Q$^3$ and Q$^2$ is as defined above. The term "amino" is used herein to refer to the group —NQ$^1$Q$^2$, where each of Q$^1$ and Q$^2$ is as defined above. The term "amine" is used herein to refer to the group: NQ$^1$Q$^2$Q$^3$, where each of Q$^1$, Q$^2$ and Q$^3$ is as defined above.

Throughout text, several abbreviations may be used to refer to specific compounds or elements. Abbreviations for atoms are as given in the periodic table (Li=lithium, for example). Other abbreviations that may be used are as follows: "i-Pr" to refer to isopropyl; "t-Bu" to refer to tertiary-butyl; "i-Bu" to refer to isobutyl; "n-Bu" to refer to normal butyl; "Me" to refer to methyl; "Et" to refer to ethyl; "Ph" to refer to phenyl; "Mes" to refer to mesityl (2,4,6-trimethyl phenyl); "acac" to refer to acetylacetonate; "AcO" to refer to acetate; "TFA" to refer to trifluoroacetate; "THF" to refer to tetrahydrofuran; "TsOH" to refer to para-toluenesulfonic acid; "cat." to refer to catalytic amount of; "LDA" to refer to lithium diisopropylamide; "DMF" to refer to dimethylformamide; "eq." to refer to molar equivalents; "TMA" to refer to trimethylaluminum; "TIBA" to refer to triisobutylaluminum. SJ$_2$BF$_{20}$ refers to [(n-C$_{10}$H$_{21}$)$_2$(4-n-C$_4$H$_9$—C$_6$H$_4$)NH][B(C$_6$F$_5$)$_4$].

This invention relates to methods for selectively oligomerizing (e.g., trimerizing and/or tetramerizing) C$_2$ to C$_{12}$ olefins, specifically ethylene, comprising reacting a catalytic composition or compound(s), optionally with one or more activators, with the olefin. As referred to herein, selective oligomerization refers to producing the desired oligomer with a selectivity of the reaction being at least 70%, more specifically at least 80% by mole of oligomer, with the possibility that an acceptable amount of polymer is present, but with the preference that no polymer is present in the product. In other embodiments, less than 20 weight % of polymer is present, specifically less than 5 weight %, more specifically less than 2 weight %, based upon the total weight of monomer converted to oligomers and polymers, where a polymer is defined to mean a molecule comprising more than 100 monomers. In other embodiments, selective oligomerization refers to producing two desired oligomers, with the selectivity of the two desired oligomers summing to at least 80% by sum of mole of oligomers.

In another embodiment, this invention relates to a method to trimerize or tetramerize a C$_2$ to C$_{12}$ olefin wherein the method produces at least 70% selectivity for the desired oligomer(s) (specifically at least 80%, specifically at least 85%, specifically at least 90%, specifically at least 95%, specifically at least 98%, specifically at least 99%, specifically 100%), calculated based upon the amount of the desired oligomer produced relative to the total yield; and at least 70% of the olefin monomer reacts to form product (specifically at least 80%, specifically at least 85%, specifically at least 90%, specifically at least 95%, specifically at least 98%, specifically at least 99%, specifically 100%).

This invention also relates to metal ligand complexes useful for the selective oligomerization of olefins. The methods of this invention specifically contact the desired monomers with a metal ligand complex or a combination of a ligand and a metal precursor (and optional activators) to form the desired oligomer. This invention also relates to a method to selectively oligomerize olefins comprising contacting olefins with a catalyst system comprising:

2) at least one ligand characterized by the general formula:

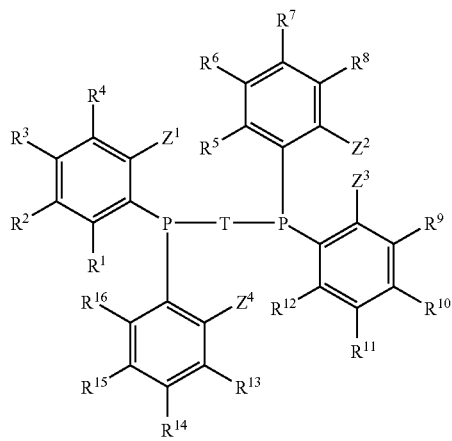

wherein

P is phosphorus;

each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$ and $R^{16}$ is, independently, selected from the group consisting of hydrogen, halogen, optionally substituted hydrocarbyl and optionally substituted heteroatom containing hydrocarbyl;

each of $Z^1$, $Z^2$, $Z^3$ or $Z^4$ is, independently, selected from a first group consisting of hydrogen, a hydrocarbyl, alkoxy, aryloxy, alkylthio, arylthio, hydroxyl, mercapto and amino, provided that at least two and less than all four of $Z^1$, $Z^2$, $Z^3$ or $Z^4$ is selected from a second group consisting of alkoxy, aryloxy, alkylthio, arylthio, hydroxyl, mercapto and amino, further provided that $Z^1$, $Z^2$, $Z^3$ and $Z^4$ may not all be methoxy, still further provided that either of the pairs of $Z^1$ and $Z^2$ or $Z^3$ and $Z^4$ are not both selected from the second group;

T is a bridging group selected from the group consisting of optionally substituted hydrocarbyl having from 2 to 20 carbon atoms;

3) a metal precursor characterized by the general formula $Cr(L)_n$ where each L is independently selected from the group consisting of halide, alkyl, substituted alkyl, cycloalkyl, substituted cycloalkyl, heteroalkyl, substituted heteroalkyl heterocycloalkyl, substituted heterocycloalkyl, aryl, substituted aryl, heteroaryl, substituted heteroaryl, alkoxy, aryloxy, hydroxy, boryl, silyl, amino, amine, hydrido, allyl, diene, seleno, phosphino, phosphine, ether, thioether, carboxylates, thio, 1,3-dionates, oxalates, carbonates, nitrates, sulfates, ethers, thioethers and combinations thereof, and wherein two or more L groups may be combined in a ring structure having from 3 to 50 non-hydrogen atoms; n is 1, 2, 3, 4, 5, or 6; and 4) optionally, one or more activators.

This invention further relates to metal ligand complexes useful for the selective oligomerization of olefins. The methods of this invention specifically contact the desired monomers with a metal ligand complex or a combination of a ligand and a metal precursor (and optional activators) to form the desired oligomer. This invention further relates to a method to selectively oligomerize olefins comprising contacting olefins with a catalyst system comprising:

2) at least one ligand characterized by the general formula:

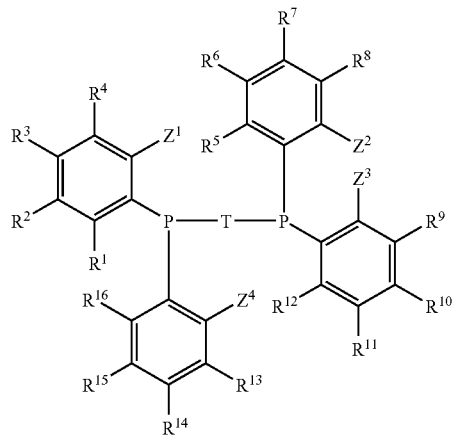

wherein

P is phosphorus;

each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$ and $R^{16}$ is, independently, selected from the group consisting of hydrogen, halogen, optionally substituted hydrocarbyl and optionally substituted heteroatom containing hydrocarbyl;

each of $Z^1$, $Z^2$, $Z^3$ or $Z^4$ is, independently, selected from the group consisting of a hydrocarbyl, alkoxy, aryloxy, alkylthio, arylthio, hydroxyl, mercapto and amino;

T is a bridging group selected from the group consisting of optionally substituted hydrocarbyl having from 2 to 20 carbon atoms;

3) a metal precursor characterized by the general formula $Cr(L)_n$ where each L is independently selected from the group consisting of halide, alkyl, substituted alkyl, cycloalkyl, substituted cycloalkyl, heteroalkyl, substituted heteroalkyl heterocycloalkyl, substituted heterocycloalkyl, aryl, substituted aryl, heteroaryl, substituted heteroaryl, alkoxy, aryloxy, hydroxy, boryl, silyl, amino, amine, hydrido, allyl, diene, seleno, phosphino, phosphine, ether, thioether, carboxylates, thio, 1,3-dionates, oxalates, carbonates, nitrates, sulfates, ethers, thioethers and combinations thereof, and wherein two or more L groups may be combined in a ring structure having from 3 to 50 non-hydrogen atoms; n is 1, 2, 3, 4, 5, or 6, provided that when $Z^1$, $Z^2$, $Z^3$ or $Z^4$ are each methoxy and T is an ethylene or methylene bridge, the metal precursor is not $CrCl_3(THF)_3$; and 4) optionally, one or more activators.

In another alternate embodiment, three of $Z^1$, $Z^2$, $Z^3$ or $Z^4$ are, independently, selected from the group consisting alkoxy, aryloxy, alkylthio, arylthio, hydroxyl, mercapto and amino and one of $Z^1$, $Z^2$, $Z^3$ or $Z^4$ is, independently, selected from the group consisting of hydrogen and hydrocarbyl.

In another alternate embodiment, each of $Z^1$, $Z^2$, $Z^3$ or $Z^4$ is, independently, selected from the group consisting alkoxy, aryloxy, alkylthio, arylthio, hydroxyl, mercapto and amino further provided that $Z^1$, $Z^2$, $Z^3$ and $Z^4$ may not all be methoxy in certain aspects of the invention as described below.

In some embodiments $Z^1$, $Z^2$, $Z^3$ and $Z^4$ are, independently selected from the group consisting of methoxy, ethoxy, propoxy, isopropoxy, butoxy, isobutoxy, tert-butoxy, pentoxy, phenoxy, methylthio, ethylthio, propylthio, isopropylthiio, butylthio, isobutylthio, tert-butylthio, phenylthio, dimethylamino, diethylamino, dipropylamino, diisopropylamino, dibutylamino, diisobutylamino, hydroxyl, and mercapto.

A specific group of ligands useful in this invention include those represented by the formulae:

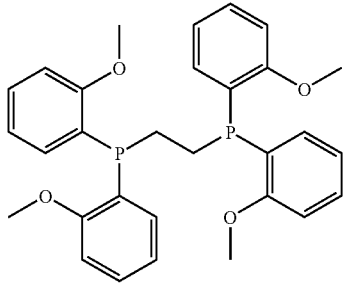

A1

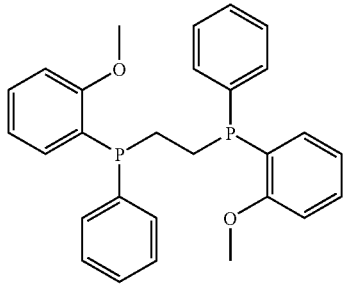

A2

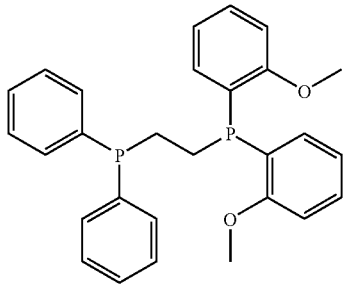

A3

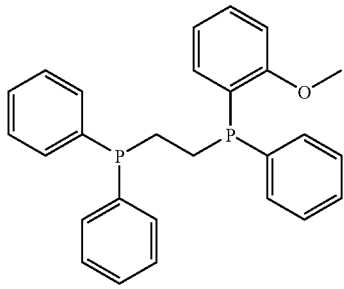

A4

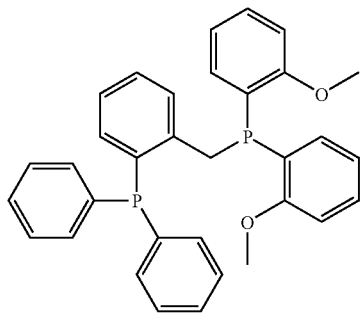

A5

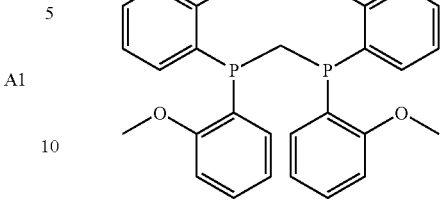

A6

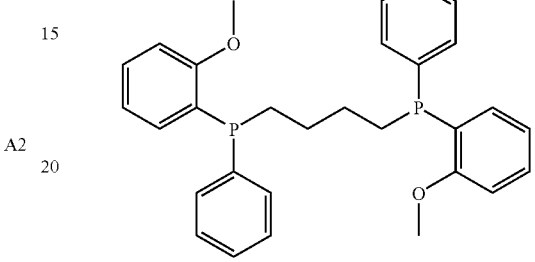

A7

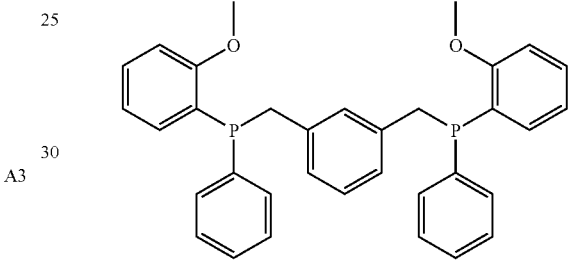

A8

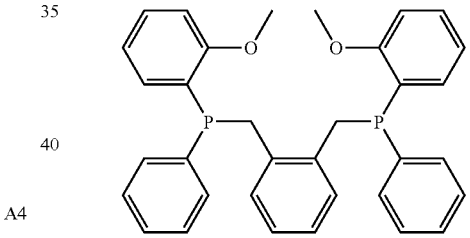

A9

In certain aspects, methods of oligomerization, compositions and catalysts are excluded from the invention when the catalyst precursor is $CrCl_3(THF)_3$ and the ligand is A1 or A6. More specifically, methods of oligomerization, compositions and catalysts are excluded from certain aspects of the invention when the catalyst precursor is $CrCl_3(THF)_3$, the ligand is A1 or A6 and the activator is modified methylalumoxane ("MMAO"). Still more specifically, methods of oligomerization, compositions and catalysts are excluded from certain aspects of the invention when the catalyst precursor is $CrCl_3(THF)_3$, the ligand is A1 or A6, the activator is MMAO, the ratio of ligand to $CrCl_3(THF)_3$ catalyst is 0.02 mmol to 0.02 mmol, in the presence of 300 equivalents MMAO, in toluene, at 1 bar of pressure with ethylene, at ambient temperature with a 60 minute run cycle, as described by Anthea Carter, et al. in Chem. Commun. 2002, 858-859 and the supplementary information appended thereto, the contents of which are incorporated herein by reference for all purposes. In view of this, it has been surprisingly found, and contrary to the teachings of Carter et al., that oligomerization can be accomplished with ligands such as A1 and A6 under appropriate conditions as evidenced by results 1 through 9 in Table 1. (For purposes of this invention and the claims thereto MMAO is defined to be methylalumoxane which includes alkyl groups other than methyl such as ethyl, isobutyl, and n-octyl.)

More specific ligands useful in the invention include: Ar$_2$PCH$_2$CH$_2$P(2-MeOPh)$_2$, where Ar is arene (in particular Ar is Ph, 2-MePh, 2,6-Me$_2$Ph, 2,4,6-Me$_3$Ph, 1-Naphthyl, 2-Naphthyl), Me is methyl, Ph is phenyl.

Where asymmetric substitution at the phosphine leads a chiral center, pure enantiomers, pure diastereomers, or mixtures thereof may be used.

Many of the ligands described throughout can be purchased. For example 1,2-Bis((2-methoxyphenyl)phenylphosphino) ethane is available from Aldrich. However, useful methods to synthesize the ligands are described below.

Ligand A2 was purchased from Aldrich. Other diphosphine bridged ligands within the scope of this invention may be prepared according to the general schemes shown below, where building blocks are first prepared and then coupled together to prepare diverse ligand structures.

Abbreviations used in this section include: Hal="halogen", preferably Cl or Br. PG="protecting group" preferably a phosphine protecting group including, but not limited to: BH$_3$. LG="leaving group" such as leaving groups for nucleophilic displacement reactions including, but not limited to: chloride, bromide, iodide, tosylate and triflate. R$^1$ to R$^{16}$, Z$^1$ to Z$^4$ and T are as defined as above.

Synthesis of Building Blocks
Synthesis of Aryl-Disubstituted Phosphines

Aryl-substituted including mono-, di- and tri-substituted phosphines can be prepared according to the procedures known to those of ordinary skill in the art (McEwen, W. E.; Beaver, B. D. *Phosphorus and Sulfur and the Related Elements* 1985, 24, 259) as illustrated by the reaction scheme given in Scheme 1 and 2.

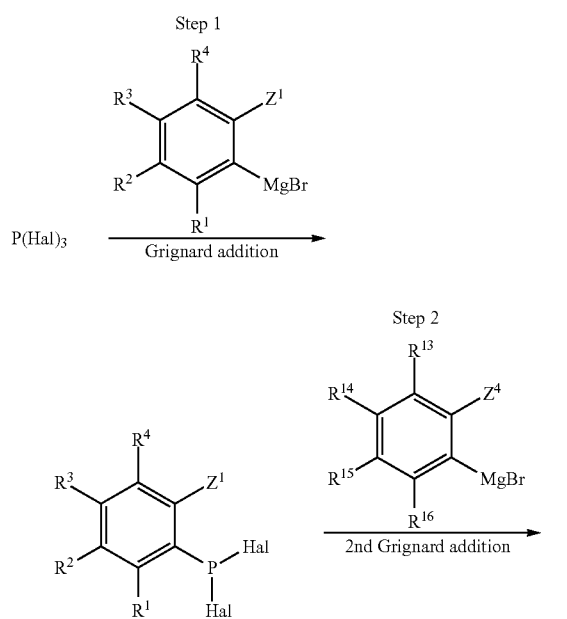

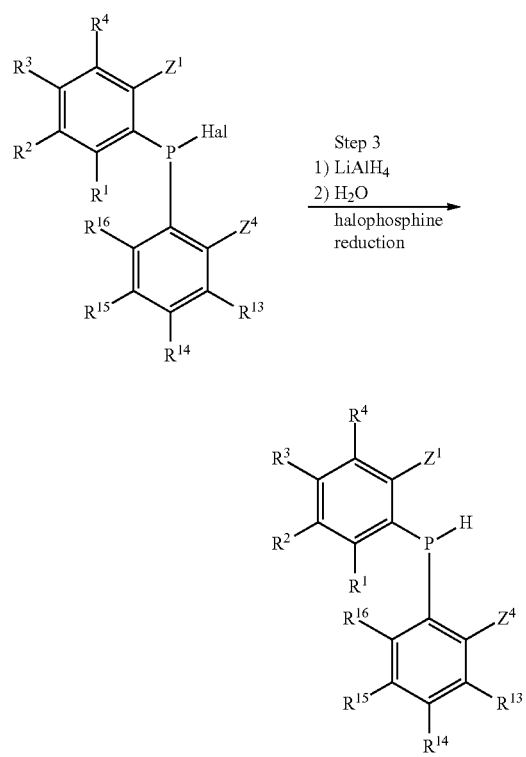

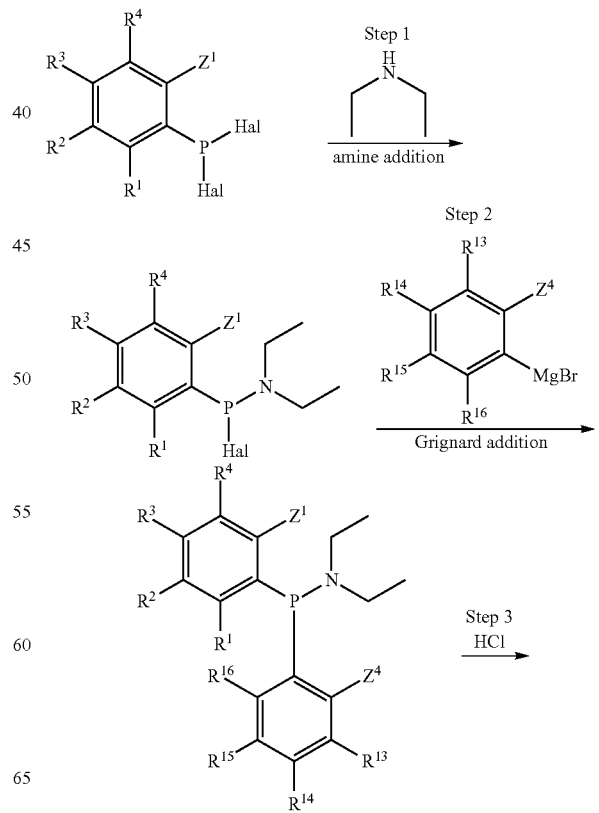

-continued

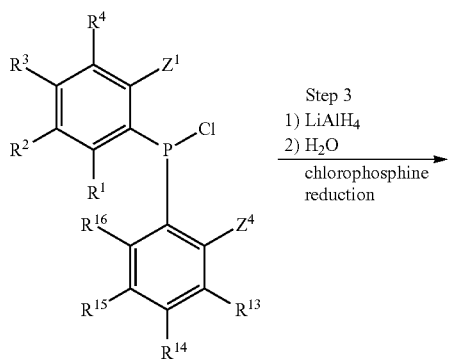

Step 3
1) LiAlH₄
2) H₂O
chlorophosphine reduction

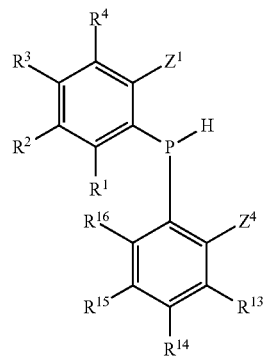

Borane Complexes of Trivalent Phosphines

Due to the air-sensitive limitations for phosphines, borane protected phosphines constitute an alternative for the synthesis of a variety of substituted phosphines (Ohff, M.; Holz, J.; Quirmbach, M.; Börner, A. *Synthesis* 1998, 1392) and can be obtained by direct treatment of the corresponding phosphines with borane (BH₃) Scheme 3.

Scheme 3

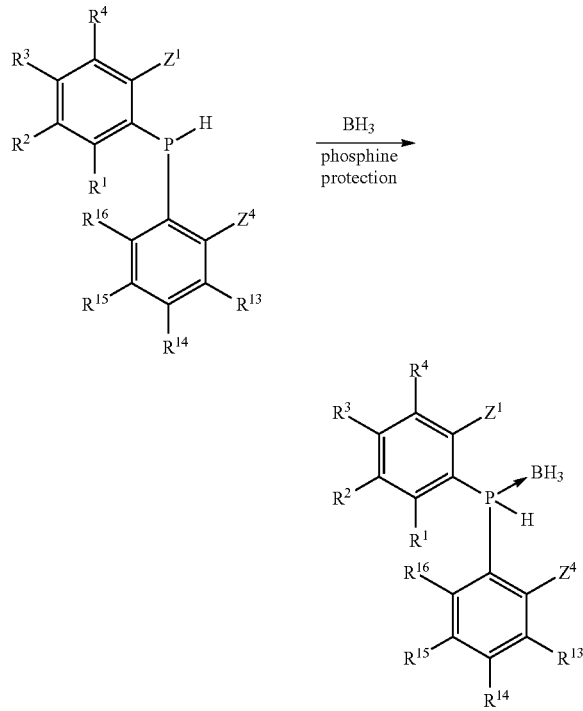

Phosphorus Containing Building Blocks

Phosphine-building blocks that contain hydroxyl or carbonyl functionalities constitute excellent starting materials to prepare phosphorus containing electrophilic building blocks. The carbonyl functionality can be reduced to the corresponding alcohols by addition of hydrides or various organometallic reagents and in a second step the resulting alcohols can be transformed in to halides by treatment with different phosphorus halides as shown in Scheme 4.

Scheme 4

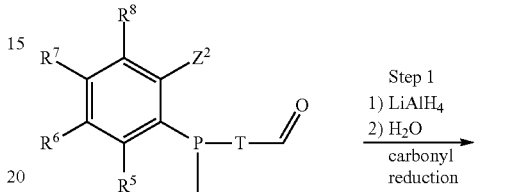

Step 1
1) LiAlH₄
2) H₂O
carbonyl reduction

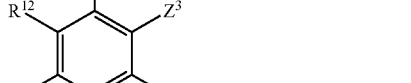

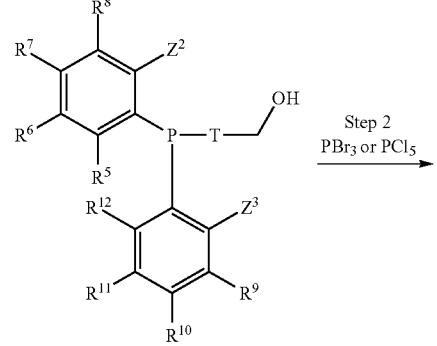

Step 2
PBr₃ or PCl₅

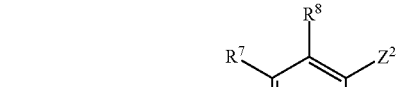
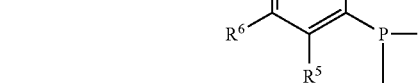
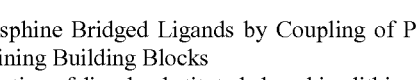

Hal = Br, Cl

Diphosphine Bridged Ligands by Coupling of Phosphorus Containing Building Blocks Reaction of diaryl-substituted phosphine lithium salts with phosphine containing electrophilic building blocks produce the diphosphine bridged ligands of the invention (Honaker, M. T.; Salvatore, R. N. *Phosphorus and Sulfur and the Related Elements* 2004, 179, 277). In this approach the phosphine lithium salt is prepared in an initial step from the respective phosphine by treatment with nBuLi and subsequent addition of the electrophile leads to the final diphosphine ligand as described in Scheme 5.

Scheme 5

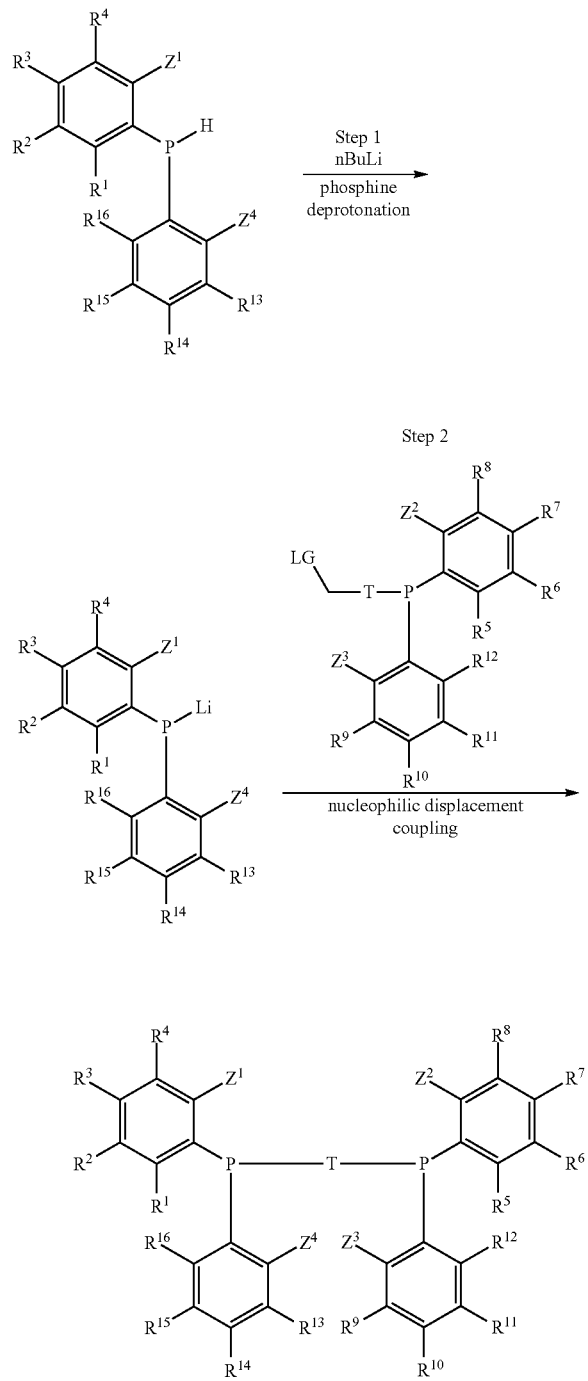

Scheme 6

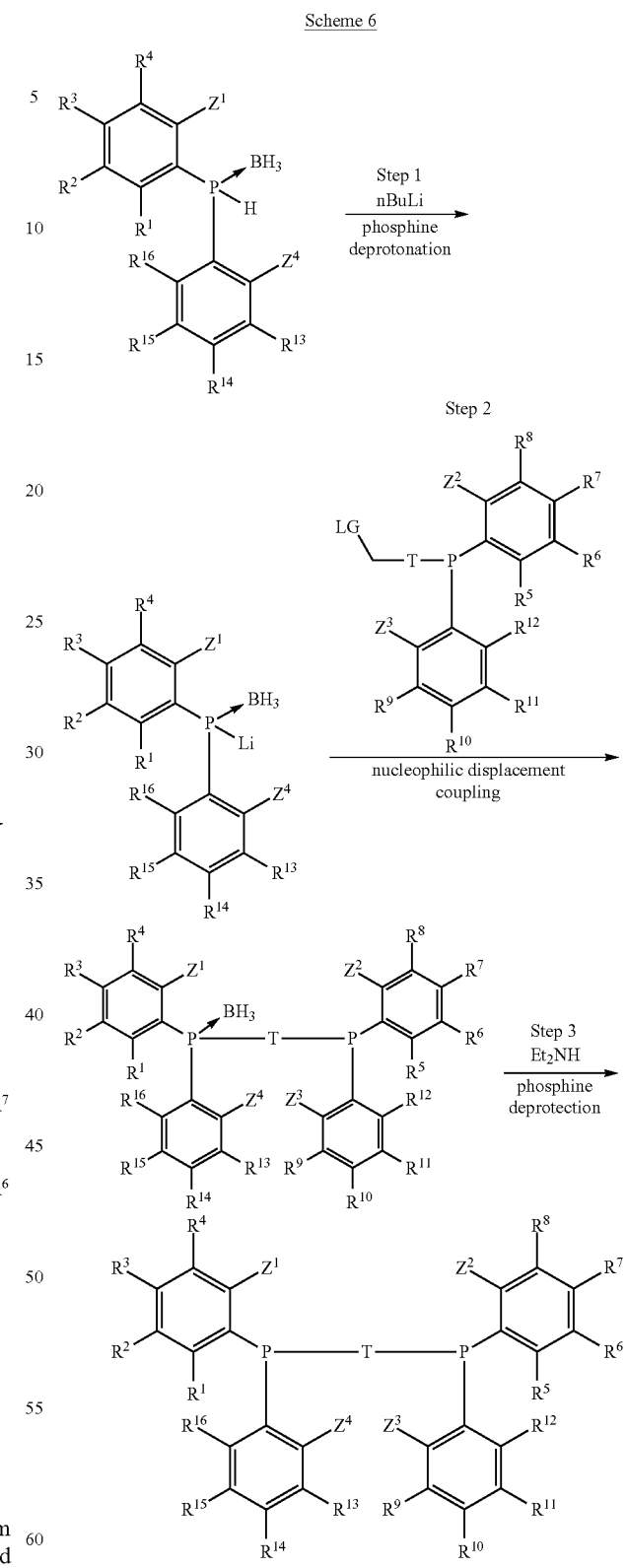

Additionally, as for diaryl-substituted phosphine lithium salts, the nucleophilic displacement of borane protected phosphine lithium salts on single, double or multiple electrophiles will generate the corresponding phosphine ligand with phosphine functionalities protected by the borane group, which can be easily removed by different methods such as, for example, treatment with an amine ($Et_2NH$) as illustrated in Scheme 6.

The addition of primary or secondary phosphine to alkene-functionalized building blocks constitute another synthetic procedure for diphosphine ligands or ligands with multiple phosphine functionalizations (Askham F. R. et al *J. Am. Chem. Soc.* 1985, 107, 7423) The reaction takes place via radical addition initiated by radical initiators such as AIBN (Azobisisobutylonitrile), as illustrated in Scheme 7.

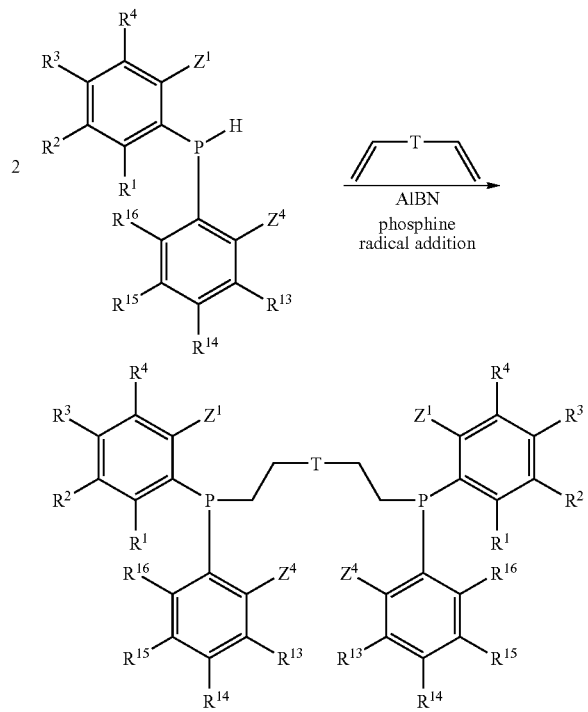

Scheme 7

It should be understood by a person having ordinary skill in the art that in the above synthetic examples, phosphorus, sulfur and nitrogen atoms can replace the oxygen heteroatom in $Z^1$, $Z^2$, $Z^3$ and/or $Z^4$.

In certain embodiments, useful ligands are prepared according to the following scheme: $Cl_2PCH_2CH_2PCl_2$+4 $Et2NH \rightarrow Cl(Et_2N)PCH_2CH_2P(NEt_2)Cl$ $Cl(Et_2N)PCH_2CH_2P(NEt_2)Cl$+2ArM$\rightarrow$Ar(Et_2N)PCH_2CH_2P(NEt_2)Ar, Ar(Et_2N)PCH_2CH_2P(NEt_2)Ar+4HCl$\rightarrow$ClArPCH_2CH_2PArCl ClArPCH_2CH_2PArCl+2Ar'M$\rightarrow$Ar'ArPCH_2CH_2PArAr', where Et is ethyl, Ar and Ar' are the same or different optionally substituted arene, M is Li or MgX, and X is Cl, or Br.

In certain embodiments, useful ligands are prepared according to the following scheme: $ClCH_2CH_2Br$+ $MPAr_2 \rightarrow ClCH_2CH_2PAr_2$, $ClCH_2CH_2PAr_2$+MPAr'$_2 \rightarrow$ Ar'$_2$PCH$_2$CH$_2$PAr$_2$ where Ar and Ar' are the same or different optionally substituted arene, M is Li, Na or K In certain embodiments, useful ligands are prepared according to the following scheme: $Ar_2PCH=CH_2$+ HPAr'$_2 \rightarrow Ar_2PCH_2CH_2PAr'_2$, where Ar and Ar' are the same or different optionally substituted arene.

For purposes of this invention, the metal containing compound may be described as a metal precursor, catalyst precursor, a pre-catalyst compound, a transition metal compound, or a catalyst compound, and these terms are used interchangeably. For purposes of this invention a metal ligand complex is defined to be the product of the combination of a metal precursor and a ligand.

Once the desired ligand is formed, it can be combined with a Cr atom, ion, compound or other Cr precursor compound, and in some embodiments the present invention encompasses compositions that include any of the above-mentioned ligands in combination with an appropriate Cr precursor and an optional activator. For example, in some embodiments, the Cr precursor can be an activated Cr precursor, which refers to a Cr precursor (described below) that has been combined or reacted with an activator (described below) prior to combination or reaction with the ancillary ligand. As noted above, in one aspect the invention provides compositions that include such combinations of ligand and Cr atom, ion, compound or precursor. In some applications, the ligands are combined with a Cr compound or precursor and the product of such combination is not determined, if a product forms. For example, the ligand may be added to a reaction vessel at the same time as the Cr precursor compound along with the reactants, activators, scavengers, etc. Additionally, the ligand can be modified prior to addition to or after the addition of the Cr precursor, e.g., through a deprotonation reaction or some other modification.

The Cr metal precursor compounds may be characterized by the general formula Cr(L)n where L is an organic group, an inorganic group, or an anionic atom; and n is an integer of 1 to 6, and when n is not less than 2, L may be the same or different from each other. Each L is a ligand independently selected from the group consisting of hydrogen, halogen, optionally substituted alkyl, heteroalkyl, allyl, diene, alkenyl, heteroalkenyl, alkynyl, heteroalkynyl, aryl, heteroaryl, alkoxy, aryloxy, boryl, silyl, amino, phosphino, ether, thioether, phosphine, amine, carboxylate, alkylthio, arylthio, 1,3 dionate, oxalate, carbonate, nitrate, sulfate, and combinations thereof. Optionally, two or more L groups are joined into a ring structure. One or more of the ligands L may be ionically bonded to Cr and, for example, L may be a non-coordinated or loosely coordinated or weakly coordinated anion (e.g., L may be selected from the group consisting of those anions described below in the conjunction with the activators). See Marks et al., Chem. Rev. 100, pp 1391-1434 (2000) for a detailed discussion of these weak interactions. The chromium precursors may be monomeric, dimeric or higher orders thereof.

Specific examples of suitable chromium precursors include, but are not limited to $(THF)_3CrCl_3$, $(THF)_3CrMeCl_2$, $(Mes)_3Cr(THF)$, $[\{TFA\}_2Cr(OEt_2)]_2$, $(THF)_3CrPh_3$, $Cr(acac)_2Ph$, $Cr(acac)_2Me$, $CrCl_3(THF)_3$, $CrCl_4(NH_3)_2$, $Cr(NMe_3)_2Cl_3$, $CrCl_3$, $Cr(acac)_3$ (acac=acetylacetonate), Cr(2-ethylhexanoate)$_3$, Cr(neopentyl)$_4$, $Cr(CH_2—C_6H_4$-o-$NMe_2)_3$, $Cr(TFA)_3$, $Cr(CH(SiMe_3)_2)_3$, $Cr(Mes)_2(THF)_3$, $Cr(Mes)_2(THF)$, $Cr(Mes)Cl(THF)_2$, $Cr(Mes)Cl(THF)_{0.5}$, $Cr(p$-tolyl$)Cl_2(THF)_3$, $Cr(diisopropylamide)_3$, $Cr(picolinate)_3$, $[Cr_2Me_8][Li(THF)]_4$, $CrCl_2$, $CrCl_2(THF)$, $Cr(NO_3)_3$, $[CrMe_6][Li(Et_2O)]_3$, $[CrPh_6][Li(THF)]_3$, $[CrPh_6][Li(n$-$Bu_2O)]_3$, $[Cr(C_4H_8)_3][Li(THF)]_3$, and other well known chromium compounds commonly used as precursors in the formation of Cr complexes and catalysts.

In certain aspects, at least one L of the metal precursor is selected from a heterocarbyl, (e.g., an alkyl or an aryl), an acetate (e.g., TFA) or a sulfonate (e.g., a mesylate). In particular, such metal precursors are useful with the ligand A1.

The ligand may be mixed with a suitable metal precursor compound prior to or simultaneously with allowing the mixture to be contacted with the reactants (e.g., monomers). In this context, the ligand to metal precursor compound ratio can be in the range of about 0.01:1 to about 100:1, more specifically in the range of about 0.1:1 to about 10:1.

Generally, the ligand (or optionally a modified ligand as discussed above) is mixed with a suitable metal (preferably Cr) precursor (and optionally other components, such as activators) prior to or simultaneously with allowing the mixture to be contacted with the reactants (e.g., monomers). When the ligand is mixed with the metal (preferably Cr) precursor compound, a metal-(preferably Cr)-ligand complex may be formed, which may itself be an active catalyst or may be transformed into a catalyst upon activation. In some embodiments the metal (preferably Cr) precursor is contacted with other ligands, then activators, then monomers.

In some embodiments, the ligand will be mixed with a suitable metal precursor prior to or simultaneous with allowing the mixture to be contacted to the reactants. When the ligand is mixed with the metal precursor, a metal-ligand complex may be formed. In connection with the metal-ligand complex and depending on the ligand or ligands chosen, the metal-ligand complex may take the form of dimers, trimers or higher orders thereof or there may be two or more metal atoms that are bridged by one or more ligands. Furthermore, two or more ligands may coordinate with a single metal atom. The exact nature of the metal-ligand complex(es) formed depends on the chemistry of the ligand and the method of combining the metal precursor and ligand, such that a distribution of metal-ligand complexes may form with the number of ligands bound to the metal being greater than, equal to or less than the number of equivalents of ligands added relative to an equivalent of metal precursor.

Cr-ligand complexes can take a number of different coordination modes. General examples of possible coordination modes include those characterized by the following general formulas:

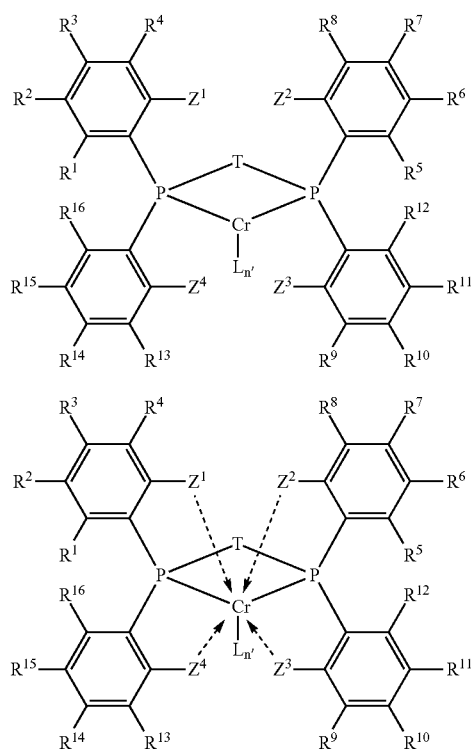

wherein n'=0, 1, 2, 3, or 4. In formula 2, any one or more of $Z^1$, $Z^2$, $Z^3$ and $Z^4$ forms a dative bond to chromium and $R^1$ to $R^{16}$, T, L, and $Z^1$ to $Z^4$ are as defined above. In certain circumstances, for instance, during catalysis, the formation of the dative bonds may be reversible. Specific examples of Cr-ligand complexes useful in the invention are shown below:

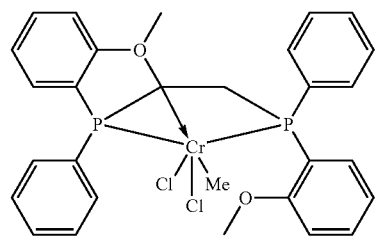

M1

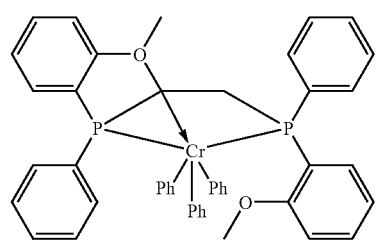

M2

In addition, the catalyst systems of this invention may be combined with other catalysts in a single reactor and/or employed in a series of reactors (parallel or serial).

The ligands-metal-precursor combinations and the metal ligand complexes, described above, are optionally activated in various ways to yield compositions active for selective ethylene oligomerization. For the purposes of this patent specification and appended claims, the terms "cocatalyst" and "activator" are used herein interchangeably and are defined to be any compound which can activate any one of the ligands-metal-precursor-combinations and the metal ligand complexes, described above by converting the combination, complex, or composition into a catalytically active species. Non-limiting activators, for example, include alumoxanes, aluminum alkyls, other metal or main group alkyl or aryl compounds, ionizing activators, which may be neutral or ionic, Lewis acids, reducing agents, oxidizing agents, and combinations thereof.

In one embodiment, alumoxane activators (also referred to as alkylalumoxane activators) are utilized as an activator in the compositions useful in the invention. Alumoxanes are generally oligomeric compounds containing —Al(R*)—O— sub-units, where R* is an alkyl group. Examples of alumoxanes include methylalumoxane (MAO), ethylalumoxane, isobutylalumoxane, and modified methylalumoxanes (MMAO), which include alkyl groups other than methyl such as ethyl, isobutyl, and n-octyl, such as MMAO-3A, PMAO-IP (referring to polymethylaluminoxane, improved process, manufactured by Akzo-Nobel and meaning an MAO prepared from a non-hydrolytic process). Alkylalumoxanes and modified alkylalumoxanes are suitable as catalyst activators, particularly when the abstractable ligand of the catalyst is a halide, alkoxide or amide. Mixtures of different alumoxanes and modified alumoxanes may also be used.

The activator compounds comprising Lewis-acid activators and in particular alumoxanes are specifically characterized by the following general formulae:

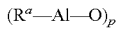

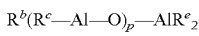

where $R^a$, $R^b$, $R^c$ and $R^e$ are, independently a $C_1$-$C_{30}$ alkyl radical, for example, methyl, ethyl, propyl, butyl, pentyl, hexyl, heptyl, octyl, nonyl, decyl, and "p" is an integer from 1 to about 50. Most specifically, $R^a$, $R^b$, $R^c$ and $R^d$ are each methyl and "p" is a least 4. When an alkyl aluminum halide or alkoxide is employed in the preparation of the alumoxane, one or more $R^a$, $R^b$, $R^c$ or $R^e$ are groups may be halide or alkoxide.

It is recognized that alumoxane is not a discrete material. An alumoxane is generally a mixture of both the linear and cyclic compounds. A typical alumoxane will contain free trisubstituted or trialkyl aluminum, bound trisubstituted or trialkyl aluminum, and alumoxane molecules of varying degree of oligomerization. Those methylalumoxanes most preferred typically contain lower levels of trimethylaluminum. Lower levels of trimethylaluminum can be achieved by reaction of the trimethylaluminum with a Lewis base or by vacuum distillation of the trimethylaluminum or by any other means known in the art.

For further descriptions, see U.S. Pat. Nos. 4,665,208, 4,952,540, 5,041,584, 5,091,352, 5,206,199, 5,204,419, 4,874,734, 4,924,018, 4,908,463, 4,968,827, 5,329,032, 5,248,801, 5,235,081, 5,157,137, 5,103,031 and EP0561476A1, EP0279586B1, EP0516476A1, EP0594218A1 and WO94/10180.

When the activator is an alumoxane (modified or unmodified), some embodiments select the maximum amount of activator at a 5000-fold molar excess Al/Cr over the catalyst precursor. A minimum preferred activator-to-catalyst-precursor is a 1:1 molar ratio. More specifically, the Al/Cr ratio is preferably from 1000:1 to 100:1.

Alumoxanes may be produced by the hydrolysis of the respective trialkylaluminum compound. MMAO may be produced by the hydrolysis of trimethylaluminum and a higher trialkylaluminum such as triisobutylaluminum. MMAO's are generally more soluble in aliphatic solvents and more stable during storage. There are a variety of methods for preparing alumoxane and modified alumoxanes, non-limiting examples of which are described in U.S. Pat. Nos. 4,665,208, 4,952,540, 5,091,352, 5,206,199, 5,204,419, 4,874,734, 4,924,018, 4,908,463, 4,968,827, 5,308,815, 5,329,032, 5,248,801, 5,235,081, 5,157,137, 5,103,031, 5,391,793, 5,391,529, 5,693,838, 5,731,253, 5,731,451, 5,744,656, 5,847,177, 5,854,166, 5,856,256 and 5,939,346 and European publications EP0561476A1, EP0279586B1, EP0594218A1 and EP0586665B1, and PCT publications WO94/10180 and WO99/15534, all of which are herein fully incorporated by reference. It may be preferable to use a visually clear methylalumoxane. A cloudy or gelled alumoxane can be filtered to produce a clear solution or clear alumoxane can be decanted from a cloudy solution. Another useful alumoxane is a modified methyl alumoxane (MMAO) cocatalyst type 3A (commercially available from Akzo Chemicals, Inc. under the trade name Modified Methylalumoxane type 3A, covered under patent number U.S. Pat. No. 5,041,584).

Aluminum alkyl or organoaluminum compounds which may be utilized as activators (or scavengers) include trimethylaluminum, triethylaluminum, triisobutylaluminum, tri-n-hexylaluminum, tri-n-octylaluminum, diisobutylaluminum hydride, ethylaluminum dichloride, diethylaluminum chloride, diethylaluminum ethoxide, and the like.

Ionizing Activators

In some embodiments, the activator includes compounds that may abstract a ligand making the metal complex cationic and providing a charge-balancing non-coordinating or weakly coordinating anion. The term "non-coordinating anion" (NCA) means an anion which either does not coordinate to said cation or which is only weakly coordinated to said cation thereby remaining sufficiently labile to be displaced by a neutral Lewis base.

It is within the scope of this invention to use an ionizing or stoichiometric activator, neutral or ionic, such as tri(n-butyl) ammonium tetrakis (pentafluorophenyl) boron, a tris(perfluorophenyl) boron metalloid precursor or a tris(perfluoronaphthyl) boron metalloid precursor, polyhalogenated heteroborane anions (WO98/43983), boric acid (U.S. Pat. No. 5,942,459) or combinations thereof. It is also within the scope of this invention to use neutral or ionic activators alone or in combination with alumoxane or modified alumoxane activators.

Examples of neutral stoichiometric activators include trisubstituted boron, tellurium, aluminum, gallium and indium or mixtures thereof. The three substituent groups are each independently selected from alkyls, alkenyls, halogen, substituted alkyls, aryls, arylhalides, alkoxy and halides. In some embodiments, the three groups are independently selected from halogen, mono or multicyclic (including halosubstituted) aryls, alkyls, and alkenyl compounds and mixtures thereof, preferred are alkenyl groups having 1 to 20 carbon atoms, alkyl groups having 1 to 20 carbon atoms, alkoxy groups having 1 to 20 carbon atoms and aryl groups having 3 to 20 carbon atoms (including substituted aryls). In other embodiments, the three groups are alkyls having 1 to 4 carbon groups, phenyl, naphthyl or mixtures thereof. In further embodiments, the three groups are halogenated, specifically fluorinated, aryl groups. In even further embodiments, the neutral stoichiometric activator is tris(perfluorophenyl) boron or tris(perfluoronaphthyl) boron.

Ionic stoichiometric activator compounds may contain an active proton, or some other cation associated with, but not coordinated to, or only loosely coordinated to, the remaining ion of the ionizing compound. Such compounds and the like are described in European publications EP0570982A1, EP0520732A1, EP0495375A1, EP0500944B1, EP0277003A1 and EP0277004A1, and U.S. Pat. Nos. 5,153,157, 5,198,401, 5,066,741, 5,206,197, 5,241,025, 5,384,299 and 5,502,124 and U.S. patent application Ser. No. 08/285,380, filed Aug. 3, 1994, all of which are herein fully incorporated by reference.

Ionic catalysts can be prepared by reacting a Cr compound with some neutral Lewis acids, such as $B(C_6F_6)_3$, which upon reaction with the abstractable ligand (X) of the Cr compound forms an anion, such as $([B(C_6F_5)_3(X)]^-)$, which stabilizes the cationic Cr species generated by the reaction. The catalysts can be prepared with activator components which are ionic compounds or compositions.

In some embodiments, compounds useful as an activator component in the preparation of the ionic catalyst systems used in the process of this invention comprise a cation, which is optionally a Brönsted acid capable of donating a proton, and a compatible non-coordinating anion which is capable of stabilizing the active catalyst species which is formed when the two compounds are combined and said anion will be sufficiently labile to be displaced by olefinic substrates or other neutral Lewis bases such as ethers, nitriles and the like. Two classes of compatible non-coordinating anions useful herein have been disclosed in EP0277003A1 and EP0277004A1 published 1988: anionic coordination complexes comprising a plurality of lipophilic radicals covalently coordinated to and shielding a central charge-bearing metal or metalloid core; and, anions comprising a plurality of boron atoms such as carboranes, metallacarboranes and boranes.

In one preferred embodiment, the stoichiometric activators include a cation and an anion component, and may be represented by the following formula:

$$(L-H)_d^+(A^{d-})$$

where L is a neutral Lewis base; H is hydrogen; (L-H)$^+$ is a Brönsted acid; A$^{d-}$ is a non-coordinating anion having the charge d$^-$; and d is an integer from 1 to 3.

The cation component, (L-H)$_d^+$ may include Brönsted acids such as protons or protonated Lewis bases or reducible Lewis acids capable of protonating or abstracting a moiety, such as an alkyl or aryl, from the bulky ligand chromium catalyst precursor, resulting in a cationic transition metal species.

The activating cation (L-H)$_d^+$ may be a Brönsted acid, capable of donating a proton to the transition metal catalytic precursor resulting in a transition metal cation, including ammoniums, oxoniums, phosphoniums, silyliums, and mixtures thereof, specifically ammoniums of methylamine, aniline, dimethylamine, diethylamine, N-methylaniline, diphenylamine, trimethylamine, triethylamine, N,N-dimethylaniline, methyldiphenylamine, pyridine, p-bromo N,N-dimethylaniline, p-nitro-N,N-dimethylaniline, phosphoniums from triethylphosphine, triphenylphosphine, and diphenylphosphine, oxoniums from ethers such as dimethyl ether diethyl ether, tetrahydrofuran and dioxane, sulfoniums from thioethers, such as diethyl thioethers and tetrahydrothiophene, and mixtures thereof. The activating cation (L-H)$_d^+$ may also be a moiety such as silver, tropylium, carbeniums, ferroceniums and mixtures, specifically carboniums and ferroceniums. In one embodiment (L-H)$_d^+$ can be triphenyl carbonium.

The anion component A$^{d-}$ includes those having the formula [M$^{k+}$Q$_n$]$^{d-}$ wherein k is an integer from 1 to 3; n is an integer from 2 to 6; n−k=d; M is an element selected from Group 13 of the Periodic Table of the Elements, specifically boron or aluminum, and Q is independently a hydride, bridged or unbridged dialkylamido, halide, alkoxide, aryloxide, hydrocarbyl, substituted hydrocarbyl, halocarbyl, substituted halocarbyl, and halosubstituted-hydrocarbyl radicals, said Q having up to 20 carbon atoms with the proviso that in not more than 1 occurrence is Q a halide. Specifically, each Q is a fluorinated hydrocarbyl group having 1 to 20 carbon atoms, more specifically each Q is a fluorinated aryl group, and most specifically each Q is a pentafluoryl aryl group. Examples of suitable A$^{d-}$ also include diboron compounds as disclosed in U.S. Pat. No. 5,447,895, which is fully incorporated herein by reference.

Illustrative, but not limiting examples of boron compounds which may be used as an activating cocatalyst in the preparation of the improved catalysts of this invention are tri-substituted ammonium salts such as: trimethylammonium tetraphenylborate, triethylammonium tetraphenylborate, tripropylammonium tetraphenylborate, tri(n-butyl)ammonium tetraphenylborate, tri(t-butyl)ammonium tetraphenylborate, N,N-dimethylanilinium tetraphenylborate, N,N-diethylanilinium tetraphenylborate, N,N-dimethyl-(2,4,6-trimethylanilinium) tetraphenylborate, tropillium tetraphenylborate, triphenylcarbenium tetraphenylborate, triphenylphosphonium tetraphenylborate, triethylsilylium tetraphenylborate, benzene(diazonium)tetraphenylborate, trimethylammonium tetrakis(pentafluorophenyl)borate, triethylammonium tetrakis(pentafluorophenyl)borate, tripopylammonium tetrakis(pentafluorophenyl)borate, tri(n-butyl)ammonium tetrakis(pentafluorophenyl)borate, tri(sec-butyl)ammonium tetrakis(pentafluorophenyl)borate, N,N-dimethylanilinium tetrakis(pentafluorophenyl)borate, N,N-diethylanilinium tetrakis(pentafluorophenyl)borate, N,N-dimethyl-(2,4,6-trimethylanilinium) tetrakis (pentafluorophenyl)borate, tropillium tetrakis (pentafluorophenyl)borate, triphenylcarbenium tetrakis (pentafluorophenyl)borate, triphenylphosphonium tetrakis (pentafluorophenyl)borate, triethylsilylium tetrakis (pentafluorophenyl)borate, benzene(diazonium) tetrakis (pentafluorophenyl)borate, trimethylammonium tetrakis-(2,3,4,6-tetrafluorophenyl) borate, triethylammonium tetrakis-(2,3,4,6-tetrafluorophenyl)borate, tripropylammonium tetrakis-(2,3,4,6-tetrafluorophenyl)borate, tri(n-butyl)ammonium tetrakis-(2,3,4,6-tetrafluoro-phenyl)borate, dimethyl(t-butyl)ammonium tetrakis-(2,3,4,6-tetrafluorophenyl)borate, N,N-dimethylanilinium tetrakis-(2,3,4,6-tetrafluorophenyl)borate, N,N-diethylanilinium tetrakis-(2,3,4,6-tetrafluorophenyl)borate, N,N-dimethyl-(2,4,6-trimethylanilinium) tetrakis-(2,3,4,6-tetrafluorophenyl) borate, tropillium tetrakis-(2,3,4,6-tetrafluorophenyl)borate, triphenylcarbenium tetrakis-(2,3,4,6-tetrafluorophenyl)borate, triphenylphosphonium tetrakis-(2,3,4,6-tetrafluorophenyl)borate, triethylsilylium tetrakis-(2,3,4,6-tetrafluorophenyl)borate, benzene(diazonium) tetrakis-(2,3,4,6-tetrafluorophenyl)borate, trimethylammonium tetrakis (perfluoronaphthyl)borate, triethylammonium tetrakis (perfluoronaphthyl)borate, tripropylammonium tetrakis (perfluoronaphthyl)borate, tri(n-butyl)ammonium tetrakis (perfluoronaphthyl)borate, tri(t-butyl)ammonium tetrakis (perfluoronaphthyl)borate, N,N-dimethylanilinium tetrakis (perfluoronaphthyl)borate, N,N-diethylanilinium tetrakis (perfluoronaphthyl)borate, N,N-dimethyl-(2,4,6-trimethylanilinium) tetrakis(perfluoronaphthyl)borate, tropillium tetrakis(perfluoronaphthyl)borate, triphenylcarbenium tetrakis(perfluoronaphthyl)borate, triphenylphosphonium tetrakis(perfluoronaphthyl)borate, triethylsilylium tetrakis(perfluoronaphthyl)borate, benzene(diazonium) tetrakis (perfluoronaphthyl)borate, trimethylammonium tetrakis (perfluorobiphenyl)borate, triethylammonium tetrakis (perfluorobiphenyl)borate, tripropylammonium tetrakis (perfluorobiphenyl)borate, tri(n-butyl)ammonium tetrakis (perfluorobiphenyl)borate, tri(t-butyl)ammonium tetrakis (perfluorobiphenyl)borate, N,N-dimethylanilinium tetrakis (perfluorobiphenyl)borate, N,N-diethylanilinium tetrakis (perfluorobiphenyl)borate, N,N-dimethyl-(2,4,6-trimethylanilinium) tetrakis(perfluorobiphenyl)borate, tropillium tetrakis(perfluorobiphenyl)borate, triphenylcarbenium tetrakis(perfluorobiphenyl)borate, triphenylphosphonium tetrakis(perfluorobiphenyl)borate, triethylsilylium tetrakis(perfluorobiphenyl)borate, benzene(diazonium) tetrakis (perfluorobiphenyl)borate, trimethylammonium tetrakis(3,5-bis(trifluoromethyl)phenyl)borate, triethylammonium tetrakis(3,5-bis(trifluoromethyl)phenyl)borate, tripropylammonium tetrakis(3,5-bis(trifluoromethyl)phenyl)borate, tri(n-butyl)ammonium tetrakis(3,5-bis(trifluoromethyl)phenyl)borate, tri(t-butyl)ammonium tetrakis(3,5-bis(trifluoromethyl)phenyl)borate, N,N-dimethylanilinium tetrakis(3,5-bis(trifluoromethyl)phenyl)borate, N,N-diethylanilinium tetrakis(3,5-bis(trifluoromethyl)phenyl)borate, N,N-dimethyl-(2,4,6-trimethylanilinium) tetrakis(3,5-bis (trifluoromethyl)phenyl)borate, tropillium tetrakis(3,5-bis (trifluoromethyl)phenyl)borate, triphenylcarbenium tetrakis (3,5-bis(trifluoromethyl)phenyl)borate, triphenylphosphonium tetrakis(3,5-bis(trifluoromethyl)phenyl)borate, triethylsilylium tetrakis(3,5-bis(trifluoromethyl) phenyl)borate, benzene(diazonium) tetrakis(3,5-bis(trifluoromethyl)phenyl)borate, and dialkyl ammonium salts such as: di-(i-propyl)ammonium tetrakis(pentafluorophenyl)borate, and dicyclohexylammonium tetrakis(pentafluorophenyl)borate; and additional tri-substituted phosphonium salts such as tri(o-tolyl)phosphonium tetrakis(pentafluorophenyl) borate, and tri(2,6-dimethylphenyl)phosphonium tetrakis (pentafluorophenyl)borate.

Most specifically, the ionic stoichiometric activator $(L-H)_d^+ (A^{d-})$ is N,N-dimethylanilinium tetra(perfluorophenyl)borate, N,N-dimethylanilinium tetrakis(perfluoronaphthyl)borate, N,N-dimethylanilinium tetrakis(perfluorobiphenyl)borate, N,N-dimethylanilinium tetrakis(3,5-bis (trifluoromethyl)phenyl)borate, triphenylcarbenium tetrakis (perfluoronaphthyl)borate, triphenylcarbenium tetrakis (perfluorobiphenyl)borate, triphenylcarbenium tetrakis(3,5-bis(trifluoromethyl)phenyl)borate, or triphenylcarbenium tetra(perfluorophenyl)borate.

Other examples of preferred ionizing activators include, $HNMe(C_{18}H_{37})_2^+B(C_6F_5)_4^-$ $HNPh(C_{18}H_{37})_2^+B(C_6F_5)_4^-$ and $((4\text{-n-Bu-}C_6H_4)NH(n\text{-hexyl})_2)^+B(C_6F_5)_4^-$ and $((4\text{-n-Bu-}C_6H_4)NH(n\text{-decyl})_2)^+B(C_6F_5)_4^-$. Specific preferred $(L^*\text{-H})^+$ cations are N,N-dialkylanilinium cations, such as $HNMe_2Ph^+$, substituted N,N-dialkylanilinium cations, such as $(4\text{-n-Bu-}C_6H_4)NH(n\text{-}C_6H_{13})_2^+$ and $(4\text{-n-Bu-}C_6H_4)NH(n\text{-}C_{10}H_{21})_2^+$ and $HNMe(C_{18}H_{37})_2^+$. Specific examples of anions are tetrakis(3,5-bis(trifluoromethyl)phenyl)borate and tetrakis(pentafluorophenyl)borate.

In one embodiment, activation methods using ionizing ionic compounds not containing an active proton but capable of producing an active oligomerization catalyst are also contemplated. Such methods are described in relation to metallocene catalyst compounds in EP 0 426 637 A1, EP 0 573 403 A1 and U.S. Pat. No. 5,387,568, which are all herein incorporated by reference.

The process can also employ cocatalyst compounds or activator compounds that are initially neutral Lewis acids but form a cationic metal complex and a noncoordinating anion, or a zwitterionic complex upon reaction with the compounds of this invention. For example, tris(pentafluorophenyl) boron or aluminum may act to abstract a hydrocarbyl or hydride ligand to yield a cationic metal complex and stabilizing non-coordinating anion.

In some embodiments, ionizing activators may be employed as described in Kohn et al. (*J. Organomet. Chem.*, 683, pp 200-208, (2003)) to, for example, improve solubility.

In another embodiment, the aforementioned cocatalyst compounds can also react with the compounds to produce a neutral, uncharged catalyst capable of selective ethylene oligomerization. For example, Lewis acidic reagents such as, for example, alkyl or aryl aluminum or boron compounds, can abstract a Lewis basic ligand such as, for example, THF or $Et_2O$, from a compound yielding a coordinatively unsaturated catalyst capable of selective ethylene oligomerization.

When the cations of noncoordinating anion precursors are Brönsted acids such as protons or protonated Lewis bases (excluding water), or reducible Lewis acids such as ferrocenium or silver cations, or alkali or alkaline earth metal cations such as those of sodium, magnesium or lithium, the activator-to-catalyst-precursor molar ratio may be any ratio, however, useful ratios can be from 1000:1 to 1:1.

Combinations of two or more activators may also be used in the practice of this invention.

Another suitable ion forming, activating cocatalyst comprises a salt of a cationic oxidizing agent and a noncoordinating, compatible anion characterized by the general formula:

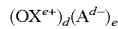

$$(OX^{e+})_d(A^{d-})_e$$

where $OX^{e+}$ is a cationic oxidizing agent having a charge of e+; e is an integer from 1 to 3; d is an integer from 1 to 3, and $A^{d-}$ is as previously defined. Examples of cationic oxidizing agents include: ferrocenium, hydrocarbyl-substituted ferrocenium, $Ag^+$, or $Pb^{+2}$. Preferred embodiments of $A^{d-}$ are those anions previously defined with respect to the Brönsted acid containing activators, especially tetrakis(pentafluorophenyl)borate.

Group 13 Reagents, Divalent Metal Reagents, and Alkali Metal Reagents

Other general activators or compounds useful in an oligomerization reaction may be used. These compounds may be activators in some contexts, but may also serve other functions in the reaction system, such as alkylating a metal center or scavenging impurities. These compounds are within the general definition of "activator," but are not considered herein to be ion-forming activators. These compounds include a group 13 reagent that may be characterized by the formula $G^{13}R^{50}_{3-p}D_p$ where $G^{13}$ is selected from the group consisting of B, Al, Ga, In, and combinations thereof, p is 0, 1 or 2, each $R^{50}$ is independently selected from the group consisting of hydrogen, halogen, and optionally substituted alkyl, alkenyl, alkynyl, heteroalkyl, heteroalkenyl, heteroalkynyl, aryl, heteroaryl, and combinations thereof, and each D is independently selected from the group consisting of halogen, hydrogen, alkoxy, aryloxy, amino, mercapto, alkylthio, arylthio, phosphino and combinations thereof.

In other embodiments, the group 13 activator is an oligomeric or polymeric alumoxane compound, such as methylalumoxane and the known modifications thereof. See, for example, Barron, "*Alkylalumoxanes, Synthesis, Structure and Reactivity*", pp. 33-67 in *Metallocene-Based Polyolefins: Preparation, Properties and Technology*, J. Schiers and W. Kaminsky (eds.), Wiley Series in Polymer Science, John Wiley & Sons Ltd., Chichester, England, 2000, and references cited therein.

In other embodiments, a divalent metal reagent may be used that is characterized by the general formula $M'R^{50}_{2-p'}D_{p'}$ and p' is 0 or 1 in this embodiment and $R^{50}$ and D are as defined above. M' is the metal and is selected from the group consisting of Mg, Ca, Sr, Ba, Zn, Cd, Cu and combinations thereof.

In still other embodiments, an alkali metal reagent may be used that is defined by the general formula $M^{iv}R^{50}$ and in this embodiment $R^{50}$ is as defined above, and $M^{iv}$ is the alkali metal and is selected from the group consisting of Li, Na, K, Rb, Cs and combinations thereof. Additionally, hydrogen and/or silanes may be used in the catalytic composition or added to the polymerization system. Silanes may be characterized by the formula $SiR^{50}_{4-q}D_q$ where $R^{50}$ is defined as above, q is 1, 2, 3 or 4 and D is as defined above, with the proviso that at least one D is hydrogen.

Non-limiting examples of Group 13 reagents, divalent metal reagents, and alkali metal reagents useful as activators for the catalyst compounds described above include methyl lithium, butyl lithium, phenyl lithium, dihexylmercury, butyl-magnesium, diethylcadmium, benzylpotassium, diethyl zinc, tri-n-butyl aluminum, diisobutyl ethylboron, diethylcadmium, di-n-butyl zinc and tri-n-amyl boron, and, in particular, the aluminum alkyls, such as trihexyl-aluminum, triethylaluminum, trimethylaluminum, and triisobutyl aluminum, diisobutyl aluminum bromide, diethylaluminum chloride, ethylaluminum dichloride, isobutyl boron dichloride, methyl magnesium chloride, ethyl beryllium chloride, ethyl calcium bromide, diisobutyl aluminum hydride, methyl cadmium hydride, diethyl boron hydride, hexylberyllium hydride, dipropylboron hydride, octylmagnesium hydride, butyl zinc hydride, dichloroboron hydride, di-bromo-aluminum hydride and bromocadmium hydride. Other Group 13 reagents, divalent metal reagents, and alkali metal reagents useful as activators for the catalyst compounds described above are known to those in the art, and a more complete discussion of these compounds may be found in U.S. Pat. Nos. 3,221,002 and 5,093,415, which are herein fully incorporated by reference.

Other activators include those described in PCT publication WO98/07515 such as tris(2,2',2"-nonafluorobiphenyl) fluoroaluminate, which publication is fully incorporated herein by reference. Combinations of activators are also contemplated by the invention, for example, alumoxanes and ionizing activators in combinations, see for example, EP 0 573 120 B1, PCT publications WO94/07928 and WO95/14044 and U.S. Pat. Nos. 5,153,157 and 5,453,410, all of which are herein fully incorporated by reference.

Other suitable activators are disclosed in WO98/09996, incorporated herein by reference, which describes activating bulky ligand metallocene catalyst compounds with perchlorates, periodates and iodates including their hydrates. WO98/30602 and WO98/30603, incorporated by reference, describe the use of lithium (2,2'-bisphenyl-ditrimethylsilicate)·4THF as an activator for a bulky ligand metallocene catalyst compound. WO99/18135, incorporated herein by reference, describes the use of organo-boron-aluminum activators. EP 0 781 299 B1 describes using a silylium salt in combination with a non-coordinating compatible anion. Also, methods of activation such as using radiation (see EP 0 615 981 B1 herein incorporated by reference), electro-chemical oxidation, and the like are also contemplated as activating methods for the purposes of rendering the chromium complexes or compositions active for the selective oligomerization of olefins. Other activators or methods are described in for example, U.S. Pat. Nos. 5,849,852, 5,859,653 and 5,869,723 and WO98/32775, WO99/42467 (dioctadecylmethylammonium-bis(tris(pentafluorophenyl)borane) benzimidazolide), which are herein incorporated by reference.

Additional optional activators include metal salts of non-coordinating or weakly coordinating anions, for example where the metal is selected from Li, Na, K, Ag, Ti, Zn, Mg, Cs, and Ba.

It is within the scope of this invention that metal-ligand complexes and or ligand-metal-precursor-combinations can be combined with one or more activators or activation methods described above. For example, a combination of activators has been described in U.S. Pat. Nos. 5,153,157 and 5,453,410, EP 0 573 120 B1, and PCT publications WO94/07928 and WO95/14044. These documents all discuss the use of an alumoxane in combination with an ionizing activator.

In one embodiment, the molar ratio of metal (from the metal-ligand-complex or the ligand-metal-precursor-combination) to activator (specifically Cr: activator, specifically Cr:Al or Cr:B) can range from 1:1 to 1:5000. In another embodiment, the molar ratio of metal to activator employed can range from 1:1 to 1:500. In another embodiment, the molar ratio of metal to activator employed can range from 1:1 to 1:100. In another embodiment, the molar ratio of chromium to activator employed can range from 1:1 to 1:500. In another embodiment, the molar ratio of chromium to activator employed can range from 1:1 to 1:100.

In embodiments where more than one activator is used, the order in which the activators are combined with the metal-ligand-complex or the ligand-metal-precursor-combination may be varied.

In some embodiments, the process of the invention relates to the oligomerization, and more specifically the trimerization and/or tetramerization of ethylene. The ligand-metal-precursor-combinations, metal-ligand-complexes, and/or catalyst systems of this invention are particularly effective at oligomerizing and specifically trimerizing and/or tetramerizing ethylene to form 1-hexene and/or 1-octene.

In other embodiments, this invention relates to the oligomerization and more specifically the trimerization and/or tetramerization of α-olefins or co-oligomerization of ethylene with α-olefins. The trimerization of α-olefins is described in Köhn et al., Angew. Chem. Int. Ed., 39 (23), pp 4337-4339 (2000).

Very generally, oligomerization can be carried out in the Ziegler-Natta or Kaminsky-Sinn methodology, including temperatures from –100° C. to 300° C. and pressures from atmospheric to 3000 atmospheres (303,900 kPa). Suspension, solution, slurry, bulk, gas phase, or high-pressure oligomerization processes may be employed with the catalysts and compounds of this invention. Such processes can be run in a batch, semi-batch, or continuous mode. Examples of such processes are well known in the art.

Suitable solvents for oligomerization are non-coordinating, inert liquids. Examples include straight and branched-chain hydrocarbons such as isobutane, butane, pentane, isopentane, hexane, isohexane, heptane, octane, dodecane, and mixtures thereof, cyclic and alicyclic hydrocarbons such as cyclohexane, cycloheptane, methylcyclohexane, methylcycloheptane, and mixtures thereof, perhalogenated hydrocarbons such as perfluorinated $C_{4-10}$ alkanes, chlorobenzene, and aromatic and alkylsubstituted aromatic compounds such as benzene, toluene, mesitylene, and xylene. Suitable solvents also include liquid olefins which may act as monomers or comonomers including ethylene, propylene, 1-butene, 1-hexene, 1-pentene, 3-methyl-1-pentene, 4-methyl-1-pentene, 1-octene, and 1-decene. Mixtures of the foregoing are also suitable.

Other additives that are useful in an oligomerization reaction may be employed, such as scavengers, promoters, modifiers, reducing agents, oxidizing agents, dihydrogen, aluminum alkyls, or silanes. For example, Jolly et al. (*Organometallics*, 16, pp 1511-1513 (1997)) has reported the use of magnesium as a reducing agent for Cr compounds that were synthesized as models for intermediates in selective ethylene oligomerization reactions.

In some useful embodiments, the activator (such as methylalumoxane or modified methylalumoxame-3A) is combined with the metal-ligand-complex or the ligand-metal-precursor-combination immediately prior to introduction into the reactor. Such mixing may be achieved by mixing in a separate tank then swift injection into the reactor, mixing in-line just prior to injection into the reactor, or the like. It has been observed that in some instances, a short activation time is very useful. Likewise in-situ activation, where the catalyst system components are injected separately into the reactor, with or without monomer, and allowed to combine within the reactor directly is also useful in the practice of this invention. In some embodiments, the catalyst system components are allowed to contact each other for 30 minutes or less, prior to contact with monomer, alternately for 5 minutes or less, alternately for 3 minutes or less, alternately for 1 minute or less.

In another embodiment, this invention relates to:
1. A method to selectively oligomerize an olefin comprising contacting the olefin with a composition comprising:
   1) at least one ligand characterized by the general formula:

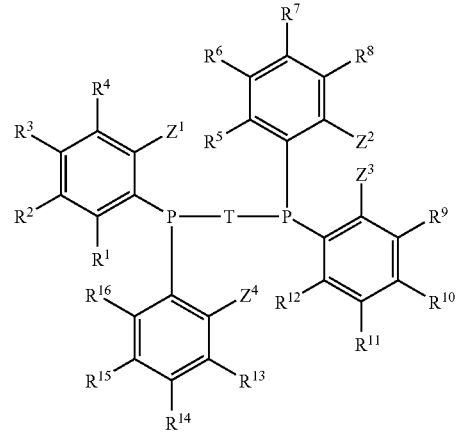

wherein
P is phosphorus;
each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$ and $R^{16}$ is, independently, selected from the group consisting of hydrogen, halogen, optionally substituted hydrocarbyl and optionally substituted heteroatom containing hydrocarbyl;

each of $Z^1$, $Z^2$, $Z^3$, and $Z^4$ is, independently, selected from a first group consisting of hydrogen, a hydrocarbyl, alkoxy, aryloxy, alkylthio, arylthio, hydroxyl, mercapto and amino;

T is a bridging group selected from the group consisting of optionally substituted hydrocarbyl having from 2 to 20 carbon atoms;

2) a metal precursor characterized by the general formula $Cr(L)_n$ where each L is independently selected from the group consisting of halide, alkyl, substituted alkyl, cycloalkyl, substituted cycloalkyl, heteroalkyl, substituted heteroalkyl heterocycloalkyl, substituted heterocycloalkyl, aryl, substituted aryl, heteroaryl, substituted heteroaryl, alkoxy, aryloxy, hydroxy, boryl, silyl, amino, amine, hydrido, allyl, diene, seleno, phosphino, phosphine, ether, thioether, carboxylates, thio, 1,3-dionates, oxalates, carbonates, nitrates, sulfates, ethers, thioethers and combinations thereof, and wherein two or more L groups may be combined in a ring structure having from 3 to 50 non-hydrogen atoms; n is 1, 2, 3, 4, 5, or 6; and 3) optionally, one or more activators, and wherein at least one of the following conditions are satisfied:

a) at least two and less than all four of $Z^1$, $Z^2$, $Z^3$, and $Z^4$ are selected from a second group consisting of alkoxy, aryloxy, alkylthio, arylthio, hydroxyl, mercapto, and amino, and $Z^1$, $Z^2$, $Z^3$, and $Z^4$ may not all be methoxy, and either of the pairs of $Z^1$ and $Z^2$ or $Z^3$ and $Z^4$ are not both selected from the second group; and b) when $Z^1$, $Z^2$, $Z^3$, and $Z^4$ are each methoxy and T is an ethylene or methylene bridge, the metal precursor is not $CrCl_3(THF)_3$, where THF is tetrahydrofuran.

2. The method of paragraph 1, wherein T has from 2 to 16 carbon atoms.

3. The method of paragraph 2, wherein T is selected from the group consisting of ethyl, propyl, butyl, pentyl, hexyl, cyclohexyl, aryl, heptyl, tolyl, octyl, nonyl, decyl, phenyl, napthyl, and dodecyl.

4. The method of any one of paragraphs 1-3, wherein each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$ is, independently, selected from the group consisting of hydrogen, a hydrocarbyl group having 1 to 20 carbon atoms, a substituted hydrocarbyl group having 1 to 20 carbon atoms and halogen.

5. The method of any one of paragraphs 1-3, wherein each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$ is, independently, selected from the group consisting of hydrogen or a $C_1$ to $C_{20}$ hydrocarbyl or substituted $C_1$ to $C_{20}$ hydrocarbyl.

6. The method of any one of paragraphs 1-5, wherein each of $Z^1$, $Z^2$, $Z^3$ or $Z^4$ is, independently, hydrogen, alkoxy, aryloxy, alkylthio, arylthio, hydroxyl, mercapto, amino, with the alkyl or aryl or substituents on these groups are a $C_1$ to $C_{20}$ hydrocarbyl group.

7. The method of paragraph 6, wherein the $C_1$ to $C_{20}$ hydrocarbyl group is selected from the group consisting of methyl, ethyl, propyl, butyl, pentyl, hexyl, cyclohexyl, aryl, heptyl, tolyl, octyl, nonyl, decyl, phenyl, napthyl, benzyl, tolyl, or dodecyl.

8. The method of any one of paragraphs 1-7, wherein each L is independently a hydrocarbyl, halide, alkoxy, carboxylate, diaonate, amino, ether, or amine.

9. The method of any one of paragraphs 1-7, wherein each L is independently chloride, mesityl, tetrahydrofuran, methyl, ethyl, butyl, pentyl, hexyl, octyl, phenyl, $Et_2O$, $NH_3$, $NMe_3$, acetylacetonate, 2-ethylhexanoate, neopentyl, $SMe_2$, $CH_2$—$C_6H_4$-o-$NMe_2$, trifluoroacetate, $CH(SiMe_3)_2$, p-tolyl, diisopropylamide, picolinate, or $NO_3$, where Et is ethyl, and Me is methyl.

10. The method of paragraph 1-5, wherein three of $Z^1$, $Z^2$, $Z^3$ or $Z^4$ are selected from the group consisting of alkoxy, aryloxy, alkylthio, arylthio, hydroxyl, mercapto, and amino.

11. The method of paragraph 1-5, wherein each of $Z^1$, $Z^2$, $Z^3$ or $Z^4$ is selected from the group consisting of aryloxy, alkylthio, arylthio, hydroxyl, mercapto and amino.

12. The method of paragraph 1, wherein the ligand is characterized by one of the general formula:

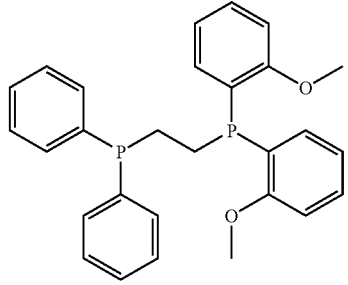

A3

13. The method of paragraph 1, wherein the ligand comprises $Ar_2PCH_2CH_2P(2-MeOPh)_2$, wherein Ar is arene, Me is methyl, and Ph is phenyl.

14. The method of any one of paragraphs 1-13, wherein the metal precursor is selected from the group consisting of $(THF)_3CrCl_3$, $(THF)_3CrMeCl_2$, $(Mes)_3Cr(THF)$, $[\{TFA\}_2Cr(OEt_2)]_2$, $(THF)_3CrPh_3$, $Cr(acac)_2Ph$, $Cr(acac)_2Me$, $CrCl_3(THF)_3$, $CrCl_4(NH_3)_2$, $Cr(NMe_3)_2Cl_3$, $CrCl_3$, $Cr(acac)_3$, $Cr(2$-ethylhexanoate$)_3$, $Cr(neopentyl)_4$, $Cr(CH_2$—$C_6H_4$-o-$NMe_2)_3$, $Cr(TFA)_3$, $Cr(CH(SiMe_3)_2)_3$, $Cr(Mes)_2(THF)_3$, $Cr(Mes)_2(THF)$, $Cr(Mes)Cl(THF)_2$, $Cr(Mes)Cl(THF)_{0.5}$, $Cr(p$-tolyl$)Cl_2(THF)_3$, $Cr(diisopropylamide)_3$, $Cr(picolinate)_3$, $[Cr_2Me_8][Li(THF)]_4$, $CrCl_2$, $CrCl_2(THF)$, $Cr(NO_3)_3$, $[CrMe_6][Li(Et_2O)]_3[CrPh_6][Li(THF)]_3$, $[CrPh_6][Li(n-Bu_2O)]_3$, $[Cr(C_4H_8)_3][Li(THF)]_3$ and mixtures thereof, where THF is tetrahydrofuran, Me is methyl, Et is ethyl, Mes is mesityl (2,4,6-trimethyl phenyl), TFA is trifluoroacetate, acac is acetylacetonate, Ph is phenyl, and n-Bu is n-butyl.

15. The method of any one of paragraphs 1-13, wherein the metal precursor is selected from the group consisting of $(THF)_3CrMeCl_2$, $(THF)_3CrCl_3$, $(Mes)_3Cr(THF)$, $Cr_2(TFA)_4(Et_2O)_2$, $(THF)_3CrPh_3$, and mixtures thereof, where THF is tetrahydrofuran, Me is methyl, Et is ethyl, Mes is mesityl (2,4,6-trimethyl phenyl), TFA is trifluoroacetate, and Ph is phenyl.

16. The method of any one of paragraphs 1-15, wherein the ligand to metal precursor compound ratio is in the range of about 0.01:1 to about 100:1.

17. The method of any one of paragraphs 1-16, wherein the activator is selected from the group consisting of modified methylalumoxane (MMAO), methylalumoxane (MAO), trimethylaluminum (TMA), triisobutyl aluminum (TIBA), polymethylalumoxane-IP (PMAO), N,N-di(n-decyl)-4-n-butyl-anilinium tetrakis(perfluorophenyl)borate, $BF_{15}$ (tris (pentafluororphenyl)borane) and mixtures thereof.

18. The method of any one of paragraphs 1-17, wherein the olefin is a $C_2$ to $C_{12}$ olefin.

19. The method of paragraph 18, wherein the olefin is a $C_2$ to $C_8$ olefin.

20. The method of paragraph 19, wherein the olefin is ethylene.

21. The method of any one of paragraphs 18-20, wherein the process produces a trimer or a tetramer of the olefin.

22. The method of paragraph 20, wherein the process produces 1-hexene.

23. The method of paragraph 20, wherein the process produces 1-octene.

24. The method of paragraph 20, wherein the process produces a mixture of 1-hexene and 1-octene.

25. The method of any one of paragraphs 1-24, wherein the reaction occurs in a hydrocarbon solvent.

26. The method of any one of paragraphs 1-31, wherein the method produces at least 70% selectivity for the desired oligomer(s), calculated based upon the amount of the desired oligomer produced relative to the total yield; and at least 70% of the olefin monomer reacts to form product.

27. A composition comprising:
   1) at least one ligand characterized by the general formula:

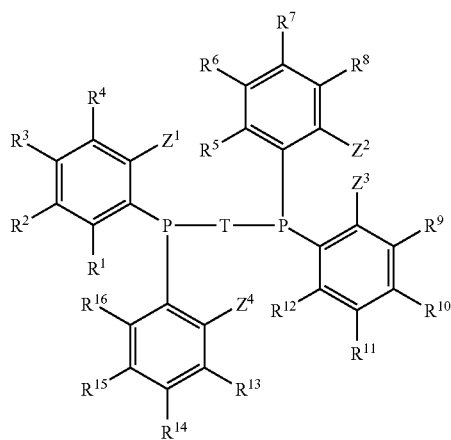

wherein
P is phosphorus;
each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$ and $R^{16}$ is, independently, selected from the group consisting of hydrogen, halogen, optionally substituted hydrocarbyl and optionally substituted heteroatom containing hydrocarbyl;
each of $Z^1$, $Z^2$, $Z^3$, and $Z^4$ is, independently, selected from a first group consisting of hydrogen, a hydrocarbyl, alkoxy, aryloxy, alkylthio, arylthio, hydroxyl, mercapto, and amino;
T is a bridging group selected from the group consisting of optionally substituted hydrocarbyl having from 2 to 20 carbon atoms;
   2) a metal precursor characterized by the general formula $Cr(L)_n$ where each L is independently selected from the group consisting of halide, alkyl, substituted alkyl, cycloalkyl, substituted cycloalkyl, heteroalkyl, substituted heteroalkyl heterocycloalkyl, substituted heterocycloalkyl, aryl, substituted aryl, heteroaryl, substituted heteroaryl, alkoxy, aryloxy, hydroxy, boryl, silyl, amino, amine, hydrido, allyl, diene, seleno, phosphino, phosphine, ether, thioether, carboxylates, thio, 1,3-dionates, oxalates, carbonates, nitrates, sulfates, ethers, thioethers and combinations thereof, and wherein two or more L groups may be combined in a ring structure having from 3 to 50 non-hydrogen atoms; n is 1, 2, 3, 4, 5, or 6; and
   3) optionally, one or more activators,
and wherein at least one of the following conditions are satisfied:
   a) at least two and less than all four of $Z^1$, $Z^2$, $Z^3$, and $Z^4$ are selected from a second group consisting of alkoxy, aryloxy, alkylthio, arylthio, hydroxyl, mercapto, and amino, and $Z^1$, $Z^2$, $Z^3$, and $Z^4$ may not all be methoxy, and either of the pairs of $Z^1$ and $Z^2$ or $Z^3$ and $Z^4$ are not both selected from the second group; and
   b) when $Z^1$, $Z^2$, $Z^3$, and $Z^4$ are each methoxy and T is an ethylene or methylene bridge, the metal precursor is not $CrCl_3(THF)_3$, where THF is tetrahydrofuran.

27. The composition of paragraph 27, wherein T has from 2 to 16 carbon atoms.

28. The composition of paragraph 28, wherein T is selected from the group consisting of ethyl, propyl, butyl, pentyl, hexyl, cyclohexyl, aryl, heptyl, tolyl, octyl, nonyl, decyl, phenyl, naphthyl, and dodecyl.

29. The composition of any one of paragraphs 27-29, wherein each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$ is, independently, selected from the group consisting of hydrogen, a hydrocarbyl group having 1 to 20 carbon atoms, a substituted hydrocarbyl group having 1 to 20 carbon atoms and halogen.

30. The composition of any one of paragraphs 27-29, wherein each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$ is, independently, selected from the group consisting of hydrogen or a $C_1$ to $C_{20}$ hydrocarbyl or substituted $C_1$ to $C_{20}$ hydrocarbyl.

31. The composition of any one of paragraphs 27-31, wherein each of $Z^1$, $Z^2$, $Z^3$ or $Z^4$ is, independently, hydrogen, alkoxy, aryloxy, alkylthio, arylthio, hydroxyl, mercapto, amino, with the alkyl or aryl or substituents on these groups are a $C_1$ to $C_{20}$ hydrocarbyl group.

32. The composition of paragraph 32, wherein the $C_1$ to $C_{20}$ hydrocarbyl group is selected from the group consisting of methyl, ethyl, propyl, butyl, pentyl, hexyl, cyclohexyl, aryl, heptyl, tolyl, octyl, nonyl, decyl, phenyl, napthyl, benzyl, tolyl, or dodecyl.

33. The composition of any one of paragraphs 27-33, wherein each L is independently a hydrocarbyl, halide, alkoxy, carboxylate, diaonate, amino, ether, or amine.

34. The composition of any one of paragraphs 27-33, wherein each L is independently chloride, mesityl, tetrahydrofuran, methyl, ethyl, butyl, pentyl, hexyl, octyl, phenyl, $Et_2O$, $NH_3$, $NMe_3$, acetylacetonate, 2-ethylhexanoate, neopentyl, $SMe_2$, $CH_2$—$C_6H_4$-o-$NMe_2$, trifluoroacetate, $CH(SiMe_3)_2$, p-tolyl, diisopropylamide, picolinate, or $NO_3$, where Et is ethyl, Me is methyl.

35. The composition of paragraph 27, wherein three of $Z^1$, $Z^2$, $Z^3$ or $Z^4$ are selected from the group consisting of alkoxy, aryloxy, alkylthio, arylthio, hydroxyl, mercapto, and amino.

36. The composition of paragraph 27, wherein each of $Z^1$, $Z^2$, $Z^3$ or $Z^4$ is selected from the group consisting of aryloxy, alkylthio, arylthio, hydroxyl, mercapto and amino.

37. The composition of paragraph 27, wherein the ligand is characterized by one of the general formula:

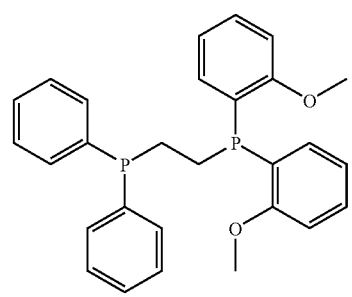

A3

38. The composition of paragraph 27, wherein the ligand comprises Ar$_2$PCH$_2$CH$_2$P(2-MeOPh)$_2$, wherein Ar is arene, Me is methyl, Ph is phenyl.

39. The composition of any one of paragraphs 27-39, wherein the metal precursor is selected from the group consisting of (THF)$_3$CrCl$_3$, (THF)$_3$CrMeCl$_2$, (Mes)$_3$Cr(THF), [{TFA}$_2$Cr(OEt$_2$)]$_2$, (THF)$_3$CrPh$_3$, Cr(acac)$_2$Ph, Cr(acac)$_2$Me, CrCl$_3$(THF)$_3$, CrCl$_4$(NH$_3$)$_2$, Cr(NMe$_3$)$_2$Cl$_3$, CrCl$_3$, Cr(acac)$_3$, Cr(2-ethylhexanoate)$_3$, Cr(neopentyl)$_4$, Cr(CH$_2$—C$_6$H$_4$-o-NMe$_2$)$_3$, Cr(TFA)$_3$, Cr(CH(SiMe$_3$)$_2$)$_3$, Cr(Mes)$_2$(THF)$_3$, Cr(Mes)$_2$(THF), Cr(Mes)Cl(THF)$_2$, Cr(Mes)Cl(THF)$_{0.5}$, Cr(p-tolyl)Cl$_2$(THF)$_3$, Cr(diisopropylamide)$_3$, Cr(picolinate)$_3$, [Cr$_2$Me$_8$][Li(THF)]$_4$, CrCl$_2$, CrCl$_2$(THF), Cr(NO$_3$)$_3$, [CrMe$_6$][Li(Et$_2$O)]$_3$[CrPh$_6$][Li(THF)]$_3$, [CrPh$_6$][Li(n-Bu$_2$O)]$_3$, [Cr(C$_4$H$_8$)$_3$][Li(THF)]$_3$ and mixtures thereof, where THF is tetrahydrofuran, Me is methyl, Et is ethyl, Mes is mesityl (2,4,6-trimethyl phenyl), TFA is trifluoroacetate, acac is acetylacetonate, Ph is phenyl, and n-Bu is n-butyl.

40. The composition of any one of paragraphs 27-39, wherein the metal precursor is selected from the group consisting of (THF)$_3$CrMeCl$_2$, (THF)$_3$CrCl$_3$, (Mes)$_3$Cr(THF), Cr$_2$(TFA)$_4$(Et$_2$O)$_2$, (THF)$_3$CrPh$_3$, and mixtures thereof, where THF is tetrahydrofuran, Me is methyl, Et is ethyl, Mes is mesityl (2,4,6-trimethyl phenyl), TFA is trifluoroacetate, Ph is phenyl.

41. The composition of any one of paragraphs 27-41, wherein the ligand to metal precursor compound ratio is in the range of about 0.01:1 to about 100:1.

42. The composition of any one of paragraphs 27-42, wherein the activator is selected from the group consisting of modified methylalumoxane (MMAO), methylalumoxane (MAO), trimethylaluminum (TMA), triisobutyl aluminum (TIBA), polymethylaluminoxane-IP (PMAO), N,N-di(n-decyl)-4-n-butyl-anilinium tetrakis(perfluorophenyl)borate, BF$_{15}$ (tris(pentafluororphenyl)borane) and mixtures thereof 43. A method to selectively oligomerize an olefin, comprising contacting the olefin with a composition comprising:
   1) at least one ligand characterized by the general formula:

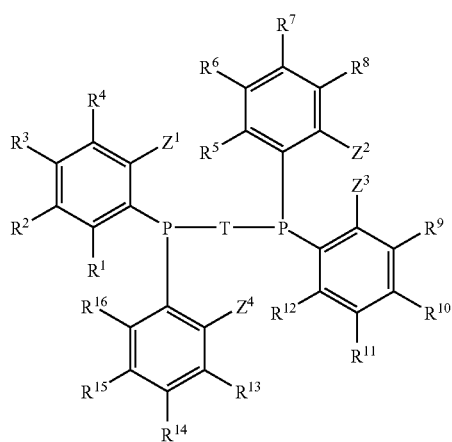

wherein
P is phosphorus;
each of R$^1$, R$^2$, R$^3$, R$^4$, R$^5$, R$^6$, R$^7$, R$^8$, R$^9$, R$^{10}$, R$^{11}$, R$^{12}$, R$^{13}$, R$^{14}$, R$^{15}$ and R$^{16}$ is, independently, selected from the group consisting of hydrogen, halogen, optionally substituted hydrocarbyl and optionally substituted heteroatom containing hydrocarbyl;
each of Z$^1$, Z$^2$, Z$^3$ or Z$^4$ is, independently selected from the group consisting of a hydrocarbyl, alkoxy, aryloxy, alkylthio, arylthio, hydroxyl, mercapto and amino;

T is a bridging group selected from the group consisting of optionally substituted hydrocarbyl having from 2 to 20 carbon atoms;
   2) a metal precursor characterized by the general formula Cr(L)$_n$ where each L is independently selected from the group consisting of halide, alkyl, substituted alkyl, cycloalkyl, substituted cycloalkyl, heteroalkyl, substituted heteroalkyl heterocycloalkyl, substituted heterocycloalkyl, aryl, substituted aryl, heteroaryl, substituted heteroaryl, alkoxy, aryloxy, hydroxy, boryl, silyl, amino, amine, hydrido, allyl, diene, seleno, phosphino, phosphine, ether, thioether, carboxylates, thio, 1,3-dionates, oxalates, carbonates, nitrates, sulfates, ethers, thioethers and combinations thereof, and wherein two or more L groups may be combined in a ring structure having from 3 to 50 non-hydrogen atoms; n is 1, 2, 3, 4, 5, or 6, provided that when Z$^1$, Z$^2$, Z$^3$ or Z$^4$ are each methoxy and T is an ethylene or methylene bridge, the metal precursor is not CrCl$_3$(THF)$_3$, where THF is tetrahydrofuran, and
   3) optionally, one or more activators.

44. The method of paragraph 44, wherein T has from 2 to 16 carbon atoms.

45. The method of paragraph 45, wherein T is selected from the group consisting of ethyl, propyl, butyl, pentyl, hexyl, cyclohexyl, aryl, heptyl, tolyl, octyl, nonyl, decyl, phenyl, naphthyl, and dodecyl.

46. The method of any of paragraphs 44, 45 or 46, wherein each of R$^1$, R$^2$, R$^3$, R$^4$, R$^5$, R$^6$, R$^7$, R$^8$, R$^9$, R$^{10}$, R$^{11}$, R$^{12}$, R$^{13}$, R$^{14}$, R$^{15}$, and R$^{16}$ is, independently, selected from the group consisting of hydrogen, a hydrocarbyl group having 1 to 20 carbon atoms, a substituted hydrocarbyl group having 1 to 20 carbon atoms and halogen.

47. The method of any of paragraphs 44, 45 or 46, wherein each of R$^1$, R$^2$, R$^4$, R$^5$, R$^6$, R$^7$, R$^8$, R$^9$, R$^{10}$, R$^{11}$, R$^{12}$, R$^{13}$, R$^{14}$, R$^{15}$, and R$^{16}$ is, independently, selected from the group consisting of hydrogen or a C$_1$ to C$_{20}$ hydrocarbyl or substituted C$_1$ to C$_{20}$ hydrocarbyl.

48. The method of paragraph 44, wherein each Z$^1$, Z$^2$, Z$^3$ and Z$^4$, independently, is selected from the group consisting of alkoxy, aryloxy, alkylthio, arylthio, hydroxyl, mercapto and amino.

49. The method of paragraph 49, wherein each Z$^1$, Z$^2$, Z$^3$ and Z$^4$, independently, is an alkoxy.

50. The method of paragraph 50, wherein each Z$^1$, Z$^2$, Z$^3$ and Z$^4$ is a methoxy.

51. The method of paragraph 44, wherein the ligand is characterized by one of the general formula:

A1

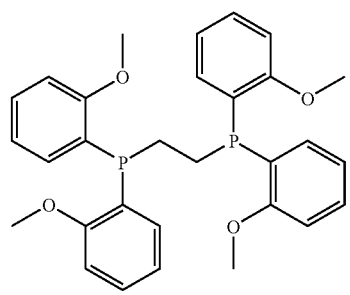

52. The method of any of paragraphs 44 through 52, wherein each L is independently a hydrocarbyl, halide, alkoxy, carboxylate, dionate, amino, ether, or amine.

53. The method of any of paragraphs 44 through 52, wherein each L is independently chloride, mesityl, tetrahydrofuran, methyl, ethyl, butyl, pentyl, hexyl, octyl, phenyl, $Et_2O$, $NH_3$, $NMe_3$, acetylacetonate, 2-ethylhexanoate, neopentyl, $SMe_2$, $CH_2$—$C_6H_4$-o-$NMe_2$, trifluoroacetate, $CH(SiMe_3)_2$, p-tolyl, diisopropylamide, picolinate, or $NO_3$, where Et is ethyl, Me is methyl.

54. The method of any of paragraphs 44 through 52, wherein the metal precursor is selected from the group consisting of: $(THF)_3CrMeCl_2$, $(Mes)_3Cr(THF)$, $[\{TFA\}_2Cr(OEt_2)]_2$, $(THF)_3CrPh_3$, $Cr(acac)_2Ph$, $Cr(acac)_2Me$, $CrCl_3(THF)_3$, $CrCl_4(NH_3)_2$, $Cr(NMe_3)_2Cl_3$, $CrCl_3$, $Cr(acac)_3$, $Cr(2$-ethylhexanoate$)_3$, $Cr(neopentyl)_4$, $Cr(CH_2$—$C_6H_4$-o-$NMe_2)_3$, $Cr(TFA)_3$, $Cr(CH(SiMe_3)_2)_3$, $Cr(Mes)_2(THF)_3$, $Cr(Mes)_2(THF)$, $Cr(Mes)Cl(THF)_2$, $Cr(Mes)Cl(THF)_{0.5}$, $Cr(p$-tolyl$)Cl_2(THF)_3$, $Cr(diisopropylamide)_3$, $Cr(picolinate)_3$, $[Cr_2Me_8][Li(THF)]_4$, $CrCl_2$, $CrCl_2(THF)$, $Cr(NO_3)_3$, $[CrMe_6][Li(Et_2O)]_3[CrPh_6][Li(THF)]_3$, $[CrPh_6][Li(n$-$Bu_2O)]_3$, $[Cr(C_4H_8)_3][Li(THF)]_3$ and mixtures thereof, where THF is tetrahydrofuran, Me is methyl, Et is ethyl, Mes is mesityl (2,4,6-trimethyl phenyl), TFA is trifluoroacetate, acac is acetylacetonate, Ph is phenyl, and n-Bu is n-butyl.

55. The method of any of paragraphs 44 through 52, wherein the metal precursor is selected from the group consisting of $(THF)_3CrMeCl_2$, $(Mes)_3Cr(THF)$, $Cr_2(TFA)_4(Et_2O)_2$, $(THF)_3CrPh_3$, and mixtures thereof, where THF is tetrahydrofuran, Me is methyl, Et is ethyl, Mes is mesityl (2,4,6-trimethyl phenyl), TFA is trifluoroacetate, and Ph is phenyl.

56. The method of any paragraphs 44 through 56, wherein the ligand to metal precursor compound ratio is in the range of about 0.01:1 to about 100:1.

57. The method of any of paragraphs 44 through 57, wherein the activator is selected from the group consisting of modified methylalumoxane (MMAO), methylalumoxane (MAO), trimethylaluminum (TMA), triisobutyl aluminum (TIBA), polymethylaluminoxane-IP (PMAO), N,N-di(n-decyl)-4-n-butyl-anilinium tetrakis(perfluorophenyl)borate, $BF_{15}$ (tris(pentafluororphenyl)borane) and mixtures thereof.

58. The method of any of paragraphs 44 through 58, wherein the olefin is a $C_2$ to $C_{12}$ olefin.

59. The method of paragraph 59, wherein the olefin is a $C_2$ to $C_8$ olefin.

60. The method of paragraph 60, wherein the olefin is ethylene.

61. The method of any of paragraphs 59, 60 or 61, wherein the process produces a trimer or a tetramer of the olefin.

62. The method of paragraph 61, wherein the process produces 1-hexene.

63. The method of paragraph 61, wherein the process produces 1-octene.

64. The method of paragraph 61, wherein the process produces a mixture of 1-hexene and 1-octene.

65. The method of any of paragraphs 44 through 65, wherein the reaction occurs in a hydrocarbon solvent.

66. The method of any of paragraphs 44 through 66, wherein the method produces at least 70% selectivity for the desired oligomer(s), calculated based upon the amount of the desired oligomer produced relative to the total yield; and at least 70% of the olefin monomer reacts to form product.

67. A composition comprising:
1) at least one ligand characterized by the general formula:

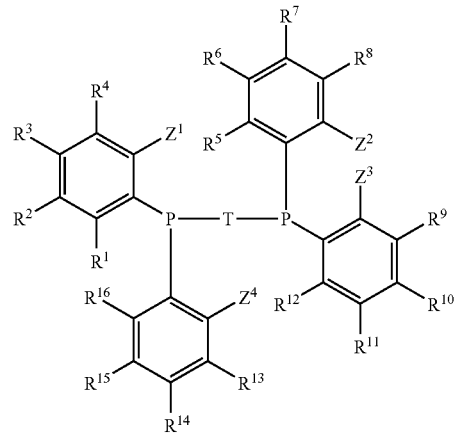

wherein
P is phosphorus;
each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$ and $R^{16}$ is, independently, selected from the group consisting of hydrogen, halogen, optionally substituted hydrocarbyl and optionally substituted heteroatom containing hydrocarbyl;
each of $Z^1$, $Z^2$, $Z^3$ or $Z^4$ is, independently, selected from the group consisting of a hydrocarbyl, alkoxy, aryloxy, alkylthio, arylthio, hydroxyl, mercapto and amino;
T is a bridging group selected from the group consisting of optionally substituted hydrocarbyl having from 2 to 20 carbon atoms;
2) a metal precursor characterized by the general formula $Cr(L)_n$ where each L is independently selected from the group consisting of halide, alkyl, substituted alkyl, cycloalkyl, substituted cycloalkyl, heteroalkyl, substituted heteroalkyl heterocycloalkyl, substituted heterocycloalkyl, aryl, substituted aryl, heteroaryl, substituted heteroaryl, alkoxy, aryloxy, hydroxy, boryl, silyl, amino, amine, hydrido, allyl, diene, seleno, phosphino, phosphine, ether, thioether, carboxylates, thio, 1,3-dionates, oxalates, carbonates, nitrates, sulfates, ethers, thioethers and combinations thereof, and wherein two or more L groups may be combined in a ring structure having from 3 to 50 non-hydrogen atoms; n is 1, 2, 3, 4, 5, or 6, provided that when $Z^1$, $Z^2$, $Z^3$ or $Z^4$ are each methoxy and T is an ethylene or methylene bridge, the metal precursor is not $CrCl_3(THF)_3$, where THF is tetrahydrofuran; and
3) optionally, one or more activators.

68. The composition of paragraph 68, wherein T has from 2 to 16 carbon atoms.

69. The composition of paragraph 69, wherein T is selected from the group consisting of ethyl, propyl, butyl, pentyl, hexyl, cyclohexyl, aryl, heptyl, tolyl, octyl, nonyl, decyl, phenyl, naphthyl, and dodecyl.

70. The composition of any of paragraphs 68, 69 or 70, wherein each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$ is, independently, selected from the group consisting of hydrogen, a hydrocarbyl group having 1 to 20 carbon atoms, a substituted hydrocarbyl group having 1 to 20 carbon atoms and halogen.

71. The composition of any of paragraphs 68, 69 or 70, wherein each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$ is, independently, selected from the group consisting of hydrogen or a $C_1$ to $C_{20}$ hydrocarbyl or substituted $C_1$ to $C_{20}$ hydrocarbyl.

72. The composition of paragraph 68, wherein each $Z^1$, $Z^2$, $Z^3$ and $Z^4$, independently, is selected from the group consisting of alkoxy, aryloxy, alkylthio, arylthio, hydroxyl, mercapto and amino.

73. The composition of paragraph 73, wherein each $Z^1$, $Z^2$, $Z^3$ and $Z^4$, independently, is an alkoxy.

74. The composition of paragraph 74, wherein each $Z^1$, $Z^2$, $Z^3$ and $Z^4$ is a methoxy.

75. The composition of paragraph 68, wherein the ligand is characterized by one of the general formula:

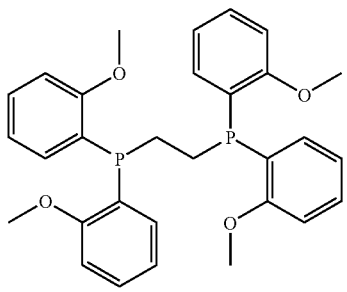

A1

76. The composition of any of paragraphs 68 through 76, wherein each L is independently a hydrocarbyl, halide, alkoxy, carboxylate, diaonate, amino, ether, or amine.

77. The composition of any of paragraphs 68 through 76, wherein each L is independently chloride, mesityl, tetrahydrofuran, methyl, ethyl, butyl, pentyl, hexyl, octyl, phenyl, $Et_2O$, $NH_3$, $NMe_3$, acetylacetonate, 2-ethylhexanoate, neopentyl, $SMe_2$, $CH_2$—$C_6H_4$-o-$NMe_2$, trifluoroacetate, $CH(SiMe_3)_2$, p-tolyl, diisopropylamide, picolinate, or $NO_3$, where Et is ethyl, Me is methyl.

78. The composition of any of paragraphs 68 through 76, wherein the metal precursor is selected from the group consisting of: $(THF)_3CrMeCl_2$, $(Mes)_3Cr(THF)$, $[\{TFA\}_2Cr(OEt_2)]_2$, $(THF)_3CrPh_3$, $Cr(acac)_2Ph$, $Cr(acac)_2Me$, $CrCl_3(THF)_3$, $CrCl_4(NH_3)_2$, $Cr(NMe_3)_2Cl_3$, $CrCl_3$, $Cr(acac)_3$ (acac=acetylacetonate), $Cr(2$-ethylhexanoate$)_3$, $Cr(neopentyl)_4$, $Cr(CH_2$—$C_6H_4$—O—$NMe_2)_3$, $Cr(TFA)_3$, $Cr(CH(SiMe_3)_2)_3$, $Cr(Mes)_2(THF)_3$, $Cr(Mes)_2(THF)$, $Cr(Mes)Cl(THF)_2$, $Cr(Mes)Cl(THF)_{0.5}$, $Cr(p$-tolyl$)Cl_2(THF)_3$, $Cr(diisopropylamide)_3$, $Cr(picolinate)_3$, $[Cr_2Me_8][Li(THF)]_4$, $CrCl_2$, $CrCl_2(THF)$, $Cr(NO_3)_3$, $[CrMe_6][Li(Et_2O)]_3$ $[CrPh_6][Li(THF)]_3$, $[CrPh_6][Li(n$-$Bu_2O)]_3$, $[Cr(C_4H_8)_3][Li(THF)]_3$ and mixtures thereof, where THF is tetrahydrofuran, Me is methyl, Et is ethyl, Mes is mesityl (2,4,6-trimethyl phenyl), TFA is trifluoroacetate, acac is acetylacetonate, Ph is phenyl, and n-Bu is n-butyl.

79. The composition of any of paragraphs 68 through 76, wherein the metal precursor is selected from the group consisting of $(THF)_3CrMeCl_2$, $(Mes)_3Cr(THF)$, $Cr_2(TFA)_4(Et_2O)_2$, $(THF)_3CrPh_3$, and mixtures thereof, where THF is tetrahydrofuran, Me is methyl, Et is ethyl, Mes is mesityl (2,4,6-trimethyl phenyl), TFA is trifluoroacetate, and Ph is phenyl.

80. The composition of any paragraphs 68 through 80, wherein the ligand to metal precursor compound ratio is in the range of about 0.01:1 to about 100:1.

81. The composition of any of paragraphs 68 through 81, wherein the activator is selected from the group consisting of modified methylalumoxane (MMAO), methylalumoxane (MAO), trimethylaluminum (TMA), triisobutyl aluminum (TIBA), polymethylaluminoxane-IP (PMAO), N,N-di(n-decyl)-4-n-butyl-anilinium tetrakis(perfluorophenyl)borate, $BF_{15}$ (tris(pentafluororphenyl)borane) and mixtures thereof 82. A metal complex characterized by the following general formula:

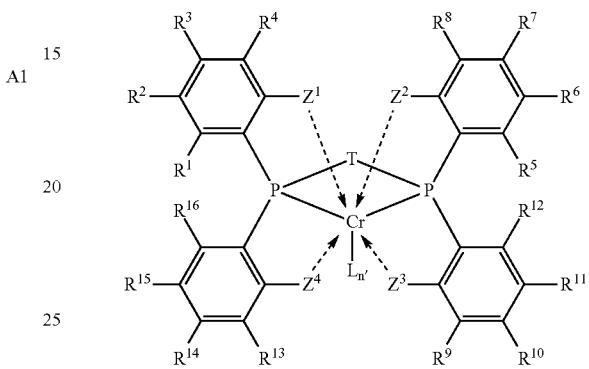

P is phosphorus;

each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$ and $R^{16}$ is, independently, selected from the group consisting of hydrogen, halogen, optionally substituted hydrocarbyl and optionally substituted heteroatom containing hydrocarbyl;

each of $Z^1$, $Z^2$, $Z^3$ or $Z^4$ is, independently, selected from a first group consisting of hydrogen, a hydrocarbyl, alkoxy, aryloxy, alkylthio, arylthio, hydroxyl, mercapto and amino, provided that at least two and less than all four of $Z^1$, $Z^2$, $Z^3$ or $Z^4$ is selected from a second group consisting of alkoxy, aryloxy, alkylthio, arylthio, hydroxyl, mercapto and amino, further provided that $Z^1$, $Z^2$, $Z^3$ and $Z^4$ may not all be methoxy, still further provided that either of the pairs of $Z^1$ and $Z^2$ or $Z^3$ and $Z^4$ are not both selected from the second group;

T is a bridging group selected from the group consisting of optionally substituted hydrocarbyl having from 2 to 20 carbon atoms;

L is independently selected from the group consisting of halide, alkyl, substituted alkyl, cycloalkyl, substituted cycloalkyl, heteroalkyl, substituted heteroalkyl heterocycloalkyl, substituted heterocycloalkyl, aryl, substituted aryl, heteroaryl, substituted heteroaryl, alkoxy, aryloxy, hydroxy, boryl, silyl, amino, amine, hydrido, allyl, diene, seleno, phosphino, phosphine, ether, thioether, carboxylates, thio, 1,3-dionates, oxalates, carbonates, nitrates, sulfates, ethers, thioethers and combinations thereof, and wherein two or more L groups may be combined in a ring structure having from 3 to 50 non-hydrogen atoms;

n' is 0, 1, 2, 3, or 4; and a dashed arrow indicates that the dative bond is an optional dative bond which may or may not be present.

83. A metal complex characterized by the following general formula:

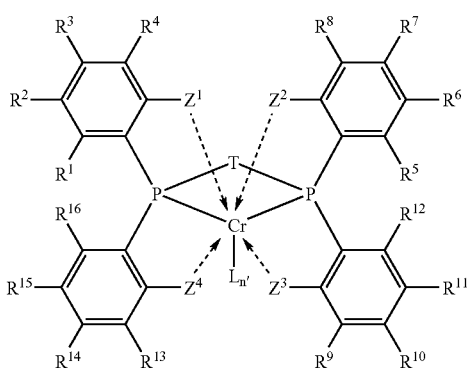

wherein

P is phosphorus;

each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$ and $R^{16}$ is, independently, selected from the group consisting of hydrogen, halogen, optionally substituted hydrocarbyl and optionally substituted heteroatom containing hydrocarbyl;

each of $Z^1$, $Z^2$, $Z^3$ or $Z^4$ is, independently selected from the group consisting of a hydrocarbyl, alkoxy, aryloxy, alkylthio, arylthio, hydroxyl, mercapto and amino;

T is a bridging group selected from the group consisting of optionally substituted hydrocarbyl having from 2 to 20 carbon atoms;

L is independently selected from the group consisting of halide, alkyl, substituted alkyl, cycloalkyl, substituted cycloalkyl, heteroalkyl, substituted heteroalkyl heterocycloalkyl, substituted heterocycloalkyl, aryl, substituted aryl, heteroaryl, substituted heteroaryl, alkoxy, aryloxy, hydroxy, boryl, silyl, amino, amine, hydrido, allyl, diene, seleno, phosphino, phosphine, ether, thioether, carboxylates, thio, 1,3-dionates, oxalates, carbonates, nitrates, sulfates, ethers, thioethers and combinations thereof, and wherein two or more L groups may be combined in a ring structure having from 3 to 50 non-hydrogen atoms, provided that when $Z^1$, $Z^2$, $Z^3$ or $Z^4$ are each methoxy and T is an ethylene or methylene bridge, L is not 3 Cl's and not 3 THF's, where THF is tetrahydrofuran;

n' is 0, 1, 2, 3, or 4; and a dashed arrow indicates that the dative bond is an optional dative bond which may or may not be present.

EXAMPLES

General: All air sensitive procedures were performed under a purified argon or nitrogen atmosphere in a Vacuum Atmospheres or MBraun glove box. All solvents used were anhydrous, de-oxygenated and purified according to known techniques (see for example, D. D. Perrin & W. L. F. Armarego Purification of Laboratory Chemicals, 3rd Ed., (Pergamon Press: New York, 1988)). All ligands and metal precursors were prepared according to procedures known to those of skill in the art, e.g., under inert atmosphere conditions, etc. Ethylene oligomerization experiments were carried out in a parallel pressure reactor, described in U.S. Pat. Nos. 6,306,658, 6,455,316 and 6,489,168, and in U.S. application Ser. No. 09/177,170, filed Oct. 22, 1998, WO 00/09255, and a parallel batch reactor with in situ injection capability, as described in WO 04/060550, and U.S. Application No. 2004/0121448, each of which is incorporated herein by reference.

Quantitative analysis of the liquid olefin products was performed using an automated Agilent 6890 Dual Channel Gas Chromatograph fitted with 2 Flame Ionization Detectors. The liquid olefin products were first separated using RT-x1 columns (1.25 m length×0.25 mm thickness×1 μm width; manufactured by Restek and spooled into module by RVM Scientific) and quantified by flame ionization detection by comparison with calibration standards. Cyclooctane was used as an internal standard. Samples were loaded onto the columns from an 8×12 array of 1 mL glass vials using a CTC HTS PAL LC-MS autosampler purchased from LEAPTEC. Polyethylene yields were determined using a Bohdan model BA-100 automated weighing module.

Ligand Synthesis

Method A

Reaction of Diaryl-Substituted Phosphine Lithium Salts with Phosphine Containing Electrophilic Building Blocks Example

[2-(diphenylphosphino)benzyl](2-methoxypheynyl)(phenyl)phosphine (A5)

Step 1

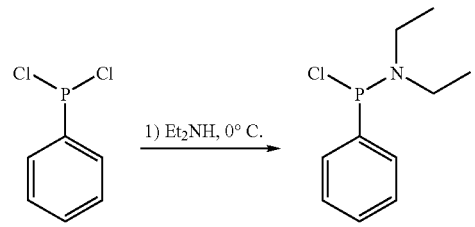

Phenyldichlorophosphine (4.47 g, 25.0 mmol) was dissolved in 80 mL of toluene and then cooled to 0° C. under N2. Diethylamine (3.65 g, 50.0 mmol) was added dropwise and the resulting reaction mixture was allowed to warm-up to room temperature (ca. 20° C.) overnight (ca. 12 hrs). Reaction was then filtered and the liquid phase was concentrated to give 5.25 g (97% yield) of N,N-diethyl-phenylphosphoramidous chloride.

Step 2

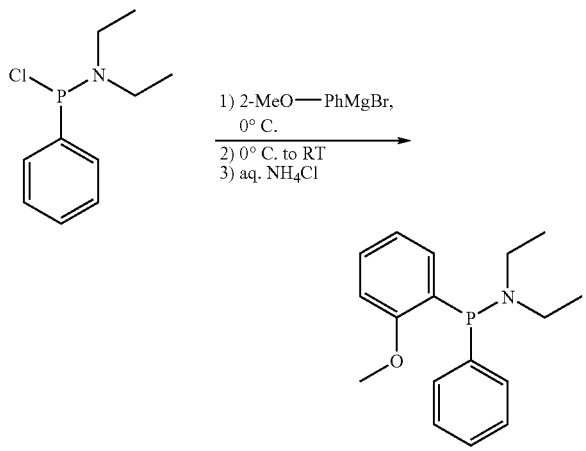

A solution of N,N-diethyl-phenylphosphoramidous (4.00 g, 18.5 mmol) in 80 mL THF was cooled to 0° C. and then a solution of 2-methoxyphenylmegnesium bromide 1.0 M in THF (20.4 mL, 20.4 mmol) was added dropwise. This solution was then allowed to warm-up to room temperature over a period of 10 hrs. Reaction was quenched with 60 mL of saturated solution of aq. NH₄Cl. The organic phase was separated and the aqueous phase was washed with ether (2×60 mL). The combined organic layers were dried over MgSO₄ and concentrated to give 4.40 g (83% yield) of N,N-diethyl-(2-methoxyphenyl)phenylphosphorus amide.

Step 3

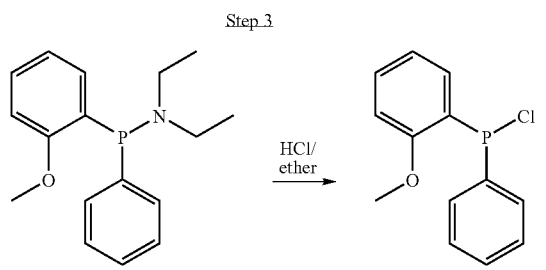 [SMILES: CCN(CC)P(c1ccccc1)c1ccccc1OC ; COc1ccccc1P(Cl)c1ccccc1]

To a solution of N,N-diethyl-(2-methoxyphenyl)phenylphosphorus amide (4.20 g, 14.61 mmol) in 40 mL ether was added dropwise a solution of hydrogen chloride 2.0 M in diethyl ether (17.0 mL, 34.0 mmol). Reaction mixture was heated under reflux for 12 hrs and then allowed to cool down. The resulting solid was filtered off and the solution was concentrated to give 3.20 g (89% yield) of 2-methoxyphenyl-phenylchlorophosphine.

Step 4

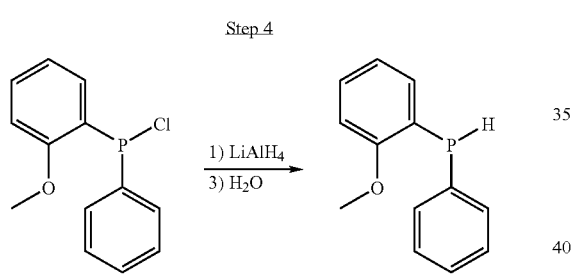

To a well stirred suspension of lithiumaluminium hydride (266.0 mg, 7.0 mmol) in 50 mL of ether was added dropwise a solution of 2-methoxyphenyl-phenylchlorophosphine (3.20 g, 12.8 mmol) in 10 mL ether. Reaction was heated under reflux for 12 hrs and then allowed to cool to room temperature (ca. 20° C.). The excess of hydride was destroyed by the careful addition (dropwise) of 30 mL of water. Organic phase was separated and the aqueous phase was extracted with ether (2×60 mL). The organic layers were combined, dried over MgSO₄ and concentrated to give 2.2 g (82%) of 2-methoxyphenyl-phenylphosphine.

Step 5

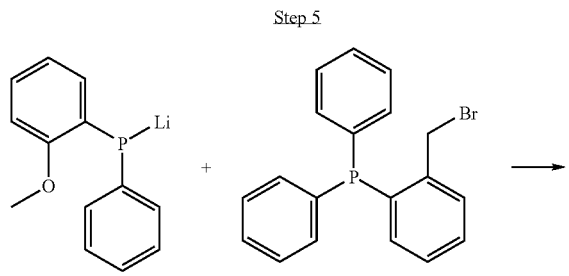

-continued

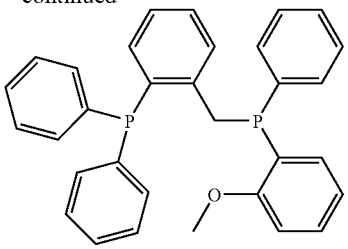

A fresh phosphine lithium salt solution was prepared from the addition of an nBuLi solution 1.6 M in hexanes (0.29 mL, 0.45 mmol) to 2-methoxyphenyl-phenylphosphine (98 mg, 0.45 mmol) in 10 mL THF at −30° C. The resulting solution was stirred for 1 hr and then treated with a solution of 2-bromomethylphenyl-diphenylphosphine (160 mg, 0.45 mmol) in 2 mL THF. Reaction was allowed to warm-up to room temperature (ca. 20° C.) over a period of 12 hrs. Solvent was removed and the residue was purified by silica-gel chromatography (95:5, hexanes:EtOAc), to give 154 mg (70% yield) of [2-(diphenylphosphino)benzyl](2-methoxyphenyl)(phenyl)phosphine (A5) a white solid.

Ligands A3, A4, A7 and A9 were also synthesized using Method A.

Method B

Reaction of Diaryl-Substituted Phosphine-Borane Lithium Salts with Phosphine Containing Electrophilic Building Blocks Example 1,3-bis[(2-methoxyphenylphenylphosphino)methyl]benzene (A8)

Step 1

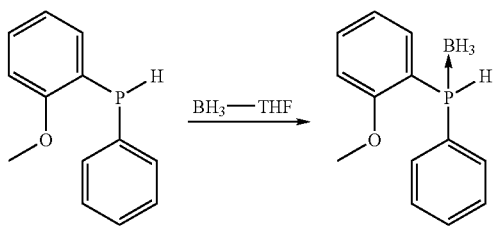

A solution of 2-methoxyphenyl-phenylphosphine (2.00 g, 9.25 mmol) in 20 mL THF was cooled to 30° C. and then a solution of borane-tetrahydrofuran complex 1.0 M in THF (13.0 mL, 13.0 mmol) was added dropwise. This solution was then allowed to warm-up to room temperature over a period of 12 hrs. Solvent was removed and the residue was purified by silica-gel chromatography (95:5-90:10, hexanes:EtOAc gradient), to give 1.87 g (88% yield) of 2-methoxyphenyl-phenylphosphine borane complex.

45

Step 2

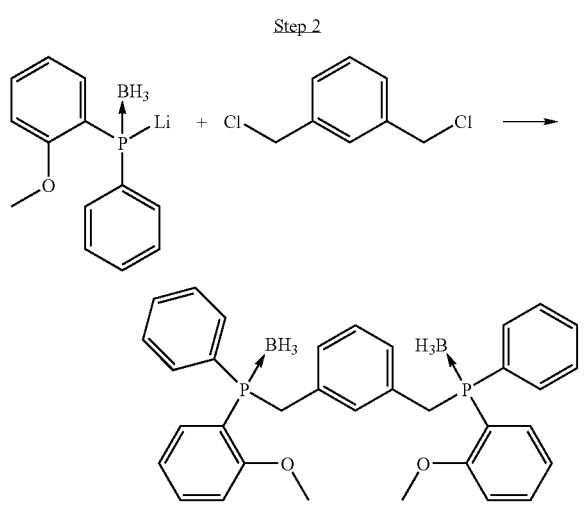

A fresh phosphine lithium salt solution was prepared from the addition of an nBuLi solution 1.6 M in hexanes (0.27 mL, 0.42 mmol) to 2-methoxyphenyl-phenylphosphine borane complex (100 mg, 0.42 mmol) in 10 mL THF at −30° C. The resulting solution was stirred for 1 hr and then treated with a solution of α,α'-dichloro-m-xylene (36.7 mg, 0.21 mmol) in 2 mL THF. Reaction was allowed to warm-up to room temperature (ca. 20° C.) over a period of 12 hrs. Solvent was removed and the residue was purified by silica-gel chromatography (95:5, hexanes:EtOAc), to give 105.0 mg (89% yield) of 1,3-bis[(2-methoxyphenylphenylphosphino)methyl]benzene diboraborane complex.

Step 3

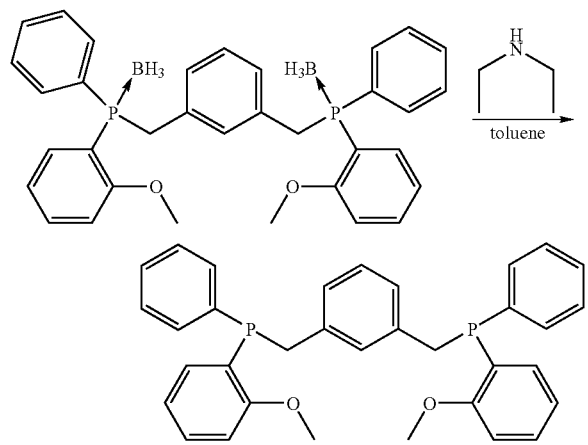

To a solution of 1,3-bis[(2-methoxyphenylphenylphosphino)methyl]benzene diboraborane complex (105.0 mg, 0.19 mmol) in 20 mL toluene was added diethylamine (30.0 mg, 0.41 mmol). Reaction mixture was heated at 60° C. for 8 hrs and then allowed to cool down to room temperature (ca. 20° C.). Solvent was removed and the solid residue was washed with ether (3×5 mL). The combined organic extracts were concentrated to give 95 mg (94% yield) of 1,3-bis[(2-methoxyphenylphenylphosphino)methyl]benzene (A8).

46

Method C

Aryllithium or Arylmagnesium Bromide Addition to bis-dichlorophosphines

Example

Bis[di(2-methoxyphenyl)phosphino]methane (A6)

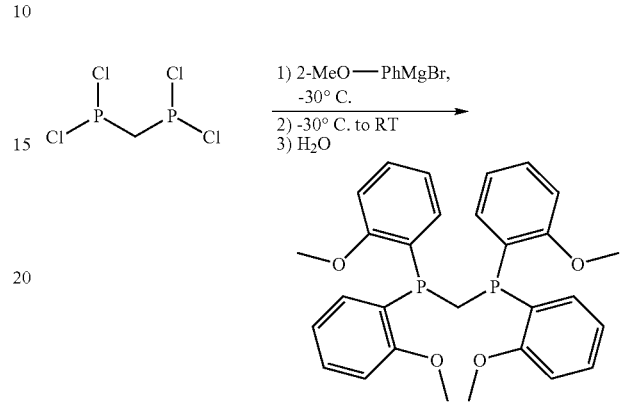

To a solution of bis(dichlorophosphino)methane (100 mg, 0.46 mmol) in 10 mL THF cooled to −30° C. was added dropwise a solution of 1.90 mL (1.90 mmol) of 1.0 M 2-methoxyphenylmegnesium bromide in THF. This solution was then allowed to warm-up to room temperature overnight (ca. 12 hrs). Reaction was diluted by addition of 10 mL of ether and the quenched with 10 mL of saturated solution of aq. $NH_4Cl$. The organic phase was separated and the aqueous phase was washed with ether (3×10 mL). The organic layers were combined, dried over $MgSO_4$ and concentrated. The residue was purified by silica-gel chromatography (90:10, hexanes:EtOAc), to give 95 (41% yield) mg of bis[di(2-methoxyphenyl)phosphino]methane (A6) as a white solid.

Ligand A1 was also synthesized using Method C.
Selective Ethylene Oligomerization Examples in a 96-Well Format
General Protocols Ethylene oligomerization reactions were performed in a 96-well format using 1 mL glass vials arranged in an 8×12 array within an aluminum block. Reagents were added from stock solutions or slurries to the 1 mL vials using a Cavro liquid handling robot driven by Symyx software, see, for example, U.S. Pat. No. 6,507,945, which is incorporated herein by reference, or a manual hand pipettor. The vials contained parylene coated stir-bars and were weighed prior to their use in screening (described below). Solutions of a parent array of desired ligands were transferred to arrays of glass vials (0.3 μmol of each ligand) and the solvent was then removed from the ligand array using a nitrogen or argon stream. The resultant ligand array was then contacted with a suitable chromium precursor, an activator (or combination of activators) and pressurized with ethylene within a parallel batch reactor with in situ injection capability. Specific details are described below. The parallel batch reactor is described in WO04/060550, and U.S. Application No. 2004/0121448, each of which is incorporated herein by reference.
Chromium Precursor Synthesis $(THF)_3CrMeCl_2$ was prepared as described in Nishimura, K. et al. *J. Organomet. Chem.* 37, pp 317-329 (1972). The compound [{TFA}$_2$Cr(OEt$_2$)]$_2$ has been previously described in Cotton, F. A. et al. *Inorg. Chem.* 17, pp 176-186

(1978), but was prepared by a different method as described below. (THF)$_3$CrPh$_3$ was prepared as described in Herwig, W. and Zeiss, H. *J. Am. Chem. Soc.* 81, pp 4798-4801 (1959). (Mes)$_3$Cr(THF) was prepared as described in Stolze, G. *J. Organomet. Chem.* 6, pp 383-388 (1966). (Mes)CrCl(THF)$_2$ was prepared as described by Stolze, G. et al. *J. Organomet. Chem.* 7, 301-310 (1967). All other Cr reagents were purchased from commercial sources.

Preparation of [{TFA}$_2$Cr(OEt$_2$)]$_2$

To a mixture of 1.00 g of CrCl$_2$ (8.14 mmol) and 1.96 g of LiTFA (16.28 mmol) was added 20 mL of diethyl ether. The pale green suspension was stirred for 15 h producing a deep violet supernatant with some traces of pale green solids. The suspension was reduced to dryness under a stream of argon and then was further dried in vacuo for about 5 minutes. The solids were then extracted with 40 mL of hexane and filtered, and were then further extracted twice with 20 mL of hexane and filtered. The filtrates were combined and reduced to dryness under a stream of argon, producing a deep purple, free-flowing crystalline solid. Isolated yield: 1.96 g.

Stock Solutions

Stock solution concentrations were as follows:

Chromium Precursors

For Complexations in Toluene: (THF)$_3$CrMeCl$_2$ (0.01 M in toluene), (Mes)$_3$Cr(THF) (0.01 M in toluene), [{TFA}$_2$Cr(OEt$_2$)]$_2$ (0.005 M in toluene).

For Complexations in THF: (THF)$_3$CrPh$_3$ (0.005 M in THF), (THF)$_3$CrMeCl$_2$ (0.005 M in THF), (Mes)$_3$Cr(THF) (0.005 M in THF), [{TFA}$_2$Cr(OEt$_2$)]$_2$ (0.005 M in THF).

Activators/Group 13 Reagents

Solutions of activators and group 13 reagents were prepared in toluene, n-heptane, or n-dodecane, depending on the choice of solvent for the selective ethylene oligomerization reaction (see Table 1). Alumoxanes were supplied by Akzo Chemical Inc., Chicago, Ill. MMAO-3A/AlR$_3$, PMAO-IP/AlR$_3$, and SJ2BF$_{20}$/AlR$_3$ mixtures were prepared within an hour prior to addition to the ligand-chromium precursor composition. SJ2BF$_{20}$ refers to [(n-C$_{10}$H$_{21}$)$_2$(4-n-C$_4$H$_9$—C$_6$H$_4$)NH][B(C$_6$F$_5$)$_4$]. AlR$_3$ refers to TMA or TIBA. Stock solutions were as follows:

MMAO-3A: 0.30 M plus 0.195 M cyclooctane as an internal standard,
MMAO-3A/TMA: 0.150 M MMAO-3A, 0.0375 M TMA plus 0.195 M cyclooctane as an internal standard,
PMAO-IP/TMA: 0.150 M PMAO-IP, 0.0375 M TMA plus 0.195 M cyclooctane as an internal standard,
MMAO-3A/TIBA: 0.150 M MMAO-3A, 0.0375 M TIBA plus 0.195 M cyclooctane as an internal standard,
SJ2BF$_{20}$/TMA: 0.0015 M SJ2BF$_{20}$, 0.0375 M TMA plus 0.195 M cyclooctane as an internal standard, and
SJ2BF$_{20}$/TIBA: 0.0015 M SJ2BF$_{20}$, 0.0375 M TIBA plus 0.195 M cyclooctane as an internal standard.

1. In Situ Preparation and Screening of Ligand-Chromium Compositions

Method 1: Toluene Room Temperature Complexation, Toluene Screening.

The ligand array (0.3 μmol of each ligand) was first contacted with toluene (ca. 30 μL per well) and then toluene solutions of the desired chromium precursor (ca. 30 μL per well, 0.3 μmol) were added. The resultant mixtures were stirred for a period of 1 hour at ambient temperature in the presence of 100-150 psi (0.67-1.03 MPa) of ethylene. The array was then treated with a stock solution of the appropriate activator (or activator mixture, 200 μL per well, contact time of ≦5 minutes), and placed into the parallel batch reactor and stirred at 50° C. under 150 psi (1.03 MPa) of ethylene for 1 hour.

Method 2: THF Room Temperature Complexation, Toluene Screening.

The ligand array (0.3 μmol of each ligand) was contacted with THF solutions of the chromium complexes (ca. 60 μL per well, 0.3 μmol) and stirred at room temperature for a period of 2 hours (in the absence of ethylene). The THF was removed by directing a stream of nitrogen or argon over each well in the array. 60 μL of toluene was then added to each well in the array, which was subsequently stirred under 100-150 psi (0.67-1.03 MPa) of ethylene for 15 minutes. The array was then treated with a stock solution of the appropriate activator (or activator mixture, 200 μL per well, contact time of ≦5 minutes), and placed into the parallel batch reactor and stirred at 50° C. under 150 psi (1.03 MPa) of ethylene for 1 hour.

Synthesis of Isolated Chromium-Compounds

Compound M1

{1(R), 2(R)-bis[(2-methoxyphenyl)phenylphosphino]ethane}CrMeCl$_2$

Ligand A2 (26.4 mg, 57.6 μmoles) and CrMeCl$_2$(THF)$_3$ (19.4 mg, 54.8 μmoles) were both dissolved in 0.6 mL toluene. While stirring, the CrMeCl2(THF)$_3$ solution was added to the ligand solution. A dark green precipitate formed immediately. The reaction was allowed to stir overnight. The majority of the reaction solvent was removed from the precipitate. The precipitate was washed with 3×1 mL toluene and dried for 10 minutes under an N$_2$ stream. The precipitate was further dried under vacuum for 15 minutes, and 23.0 mg of the compound was isolated (70.4% yield).

Compound M2

{1(R), 2(R)-bis[(2-methoxyphenyl)phenylphosphino]ethane}CrPh$_3$

Ligand A2 (55.2 mg, 120.4 μmoles) was dissolved in 2.5 mL dichloromethane. CrPh$_3$(THF)$_3$ (59.0 mg, 118.1 μmoles) was slurried in 200 μL of THF. While stirring, the CrPh$_3$(THF)$_3$ slurry was added to the ligand solution. Upon addition, the color of solution turns deep red. The solvent was removed with an N$_2$ stream after 25 minutes. The dark red residue was dissolved in 0.5 mL CH$_2$Cl$_2$, layered with 3.5 mL pentane, and placed in a −35° C. freezer overnight. The supernatant was removed while the vial was cold, and the reddish-orange solid was washed with 3×1 mL room temperature pentane. The powder was dried under vacuum for 15 minutes, and 57.3 mg of the compound was isolated (65.4% yield).

Product Analysis

After 1 hour of reaction, the parallel batch reactor was depressurized and the array was removed. The array of vials was then transferred to a room temperature aluminum block, and to each vial was added ca. 200 μL of toluene followed by 30-50 μL of water. The vials were stirred and then topped off with toluene to bring the total volume to ca. 800 μL. A Teflon sheet and rubber gasket were placed over the top of the array and an aluminum cover was screwed on the top to seal the array. The array was then mechanically agitated and centrifuged at 1500 rpm for 10 minutes before analyzing the composition of each well using Gas Chromatography with a Flame Ionization Detector (e.g. the GC-FID technique). Following the GC analysis of the array, the volatiles were removed under vacuum centrifuge and the vials were weighed in order to determine the yield of solid product. The calculated catalyst and cocatalyst residues were then subtracted from the weight to give the yield of polyethylene produced. Table 1 presents selected results from the selective ethylene oligomerization reactions performed in 96-well formats. In Table 1, 1-hexene selectivity is shown as a percentage and is defined as 100×[micromoles of 1-hexene]/[sum of micromoles of $C_6$-$C_{16}$ olefins].

TABLE 1A

| Example | Ligand (0.3 µmol) | Chromium Precursor (0.3 µmol) | Method | Solvent | Reactor Temp (° C.) |
|---|---|---|---|---|---|
| 1 | A1 | $Cr(CH_3)Cl_2(THF)_3$ | 1 | Toluene | 50 |
| 2 | A1 | $Cr(mes)_3(THF)$ | 1 | Toluene | 50 |
| 3 | A1 | $[Cr\{TFA\}_2(Et_2O)]_2$ | 1 | Toluene | 50 |
| 4 | A1 | $CrPh_3(THF)_3$ | 2 | Toluene | 50 |
| 5 | A1 | $Cr(CH_3)Cl_2(THF)_3$ | 1 | Toluene | 50 |
| 6 | A1 | $[Cr\{TFA\}_2(Et_2O)]_2$ | 1 | Toluene | 50 |
| 7 | A1 | $Cr(mes)_3(THF)$ | 1 | Toluene | 50 |
| 8 | A1 | $CrPh_3(THF)_3$ | 2 | Toluene | 50 |
| 9 | A2 | $Cr(CH_3)Cl_2(THF)_3$ | 1 | Toluene | 50 |
| 10 | A2 | $Cr(mes)_3(THF)$ | 1 | Toluene | 50 |
| 11 | A2 | $[Cr\{TFA\}_2(Et_2O)]_2$ | 1 | Toluene | 50 |
| 12 | A2 | $CrPh_3(THF)_3$ | 2 | Toluene | 50 |
| 13 | A2 | $Cr(CH_3)Cl_2(THF)_3$ | 1 | Toluene | 50 |
| 14 | A2 | $Cr(mes)_3(THF)$ | 1 | Toluene | 50 |
| 15 | A2 | $CrPh_3(THF)_3$ | 2 | Toluene | 50 |
| 16 | A3 | $Cr(CH_3)Cl_2(THF)_3$ | 1 | Toluene | 50 |
| 17 | A3 | $Cr(CH_3)Cl_2(THF)_3$ | 1 | Toluene | 50 |
| 18 | A3 | $Cr(CH_3)Cl_2(THF)_3$ | 1 | Toluene | 50 |
| 19 | A3 | $Cr(CH_3)Cl_2(THF)_3$ | 1 | Toluene | 50 |
| 20 | A3 | $Cr(mes)_3(THF)$ | 1 | Toluene | 50 |
| 21 | A3 | $CrPh_3(THF)_3$ | 2 | Toluene | 50 |
| 22 | A3 | $Cr(mes)_3(THF)$ | 1 | Toluene | 50 |
| 23 | A3 | $CrPh_3(THF)_3$ | 2 | Toluene | 50 |
| 24 | A4 | $Cr(CH_3)Cl_2(THF)_3$ | 1 | Toluene | 50 |
| 25 | A4 | $Cr(CH_3)Cl_2(THF)_3$ | 1 | Toluene | 50 |
| 26 | A4 | $Cr(CH_3)Cl_2(THF)_3$ | 1 | Toluene | 50 |
| 27 | A4 | $Cr(CH_3)Cl_2(THF)_3$ | 1 | Toluene | 50 |
| 28 | A4 | $Cr(mes)_3(THF)$ | 1 | Toluene | 50 |
| 29 | A4 | $CrPh_3(THF)_3$ | 2 | Toluene | 50 |
| 30 | A4 | $Cr(mes)_3(THF)$ | 1 | Toluene | 50 |
| 31 | A4 | $CrPh_3(THF)_3$ | 2 | Toluene | 50 |
| 32 | A5 | $Cr(mes)_3(THF)$ | 1 | Toluene | 50 |
| 33 | A5 | $CrPh_3(THF)_3$ | 2 | Toluene | 50 |
| 34 | A5 | $Cr(mes)_3(THF)$ | 1 | Toluene | 50 |

THF is tetrahydrofuran, mes is mesityl, Et is ethyl, TFA is trifluoroacetate, Ph is phenyl.

TABLE 1B

| Ex | Activation Method and mol Equivalents versus Cr | µmol Catalyst | µmol 1-Hexene Produced | 1-hexene Selectivity (%) | mg Polyethylene produced |
|---|---|---|---|---|---|
| 1 | 100 MMAO-3A/25 TIBA | 0.3 | 97 | 97 | 1 |
| 2 | 100 MMAO-3A/25 TIBA | 0.3 | 908 | 98 | 2 |
| 3 | 100 MMAO-3A/25 TIBA | 0.3 | 85 | 98 | <1 |
| 4 | 100 MMAO-3A/25 TIBA | 0.3 | 579 | 97 | 2 |
| 5 | 100 PMAO-IP/25 TMA | 0.3 | 94 | 97 | 2 |
| 6 | 100 PMAO-IP/25 TMA | 0.3 | 96 | 97 | 1 |
| 7 | 1.1 SJ2BF$_{20}$/25 TIBA | 0.3 | 224 | 98 | 6 |
| 8 | 1.1 SJ2BF$_{20}$/25 TIBA | 0.3 | 732 | 98 | 12 |
| 9 | 100 MMAO-3A/25 TIBA | 0.3 | 1185 | 95 | 1 |
| 10 | 100 MMAO-3A/25 TIBA | 0.3 | 1830 | 89 | 2 |
| 11 | 100 MMAO-3A/25 TIBA | 0.3 | 202 | 96 | 56 |
| 12 | 100 MMAO-3A/25 TIBA | 0.3 | 1112 | 83 | 2 |
| 13 | 100 PMAO-IP/25 TMA | 0.3 | 950 | 93 | 2 |
| 14 | 1.1 SJ2BF$_{20}$/25 TIBA | 0.3 | 817 | 94 | 3 |
| 15 | 1.1 SJ2BF$_{20}$/25 TIBA | 0.3 | 783 | 88 | 4 |
| 16 | 100 MMAO-3A/25 TIBA | 0.3 | 2710 | 91 | 1 |
| 17 | 100 MMAO-3A/25 TIBA | 0.3 | 2523 | 89 | 2 |
| 18 | 100 PMAO-IP/25 TMA | 0.3 | 1581 | 94 | 4 |
| 19 | 100 PMAO-IP/25 TMA | 0.3 | 1575 | 95 | 4 |
| 20 | 100 MMAO-3A/25 TIBA | 0.3 | 1269 | 83 | 2 |
| 21 | 100 MMAO-3A/25 TIBA | 0.3 | 1148 | 85 | 2 |
| 22 | 1.1 SJ2BF$_{20}$/25 TIBA | 0.3 | 950 | 86 | 1 |
| 23 | 1.1 SJ2BF$_{20}$/25 TIBA | 0.3 | 1020 | 91 | 6 |
| 24 | 100 MMAO-3A/25 TIBA | 0.3 | 2111 | 88 | 2 |
| 25 | 100 MMAO-3A/25 TIBA | 0.3 | 1775 | 86 | 2 |
| 26 | 100 PMAO-IP/25 TMA | 0.3 | 1601 | 88 | 3 |

TABLE 1B-continued

| Ex | Activation Method and mol Equivalents versus Cr | μmol Catalyst | μmol 1-Hexene Produced | 1-hexene Selectivity (%) | mg Polyethylene produced |
|---|---|---|---|---|---|
| 27 | 100 PMAO-IP/25 TMA | 0.3 | 1416 | 86 | 3 |
| 28 | 100 MMAO-3A/25 TIBA | 0.3 | 1217 | 86 | 2 |
| 29 | 100 MMAO-3A/25 TIBA | 0.3 | 1013 | 86 | 2 |
| 30 | 1.1 SJ2BF$_{20}$/25 TIBA | 0.3 | 369 | 94 | <1 |
| 31 | 1.1 SJ2BF$_{20}$/25 TIBA | 0.3 | 970 | 92 | 6 |
| 32 | 100 MMAO-3A/25 TIBA | 0.3 | 823 | 91 | 29 |
| 33 | 100 MMAO-3A/25 TIBA | 0.3 | 590 | 85 | 72 |
| 34 | 1.1 SJ2BF$_{20}$/25 TIBA | 0.3 | 174 | 85 | 31 |

MMAO-3A is modified methylalumoxane (obtained from Akzo-Nobel); PMAO-IP is polymethylaluminoxane (obtained from Akzo-Nobel); SJ2BF$_{20}$ is [(n-C$_{10}$H$_{21}$)$_2$(4-n-C$_4$H$_9$—C$_6$H$_4$)NH][B(C$_6$F$_5$)$_4$], TIBA is triisobutylaluminum.

Example X

Selective Ethylene Oligomerization Reactions in a 48-Well Parallel Pressure Reactor Ethylene oligomerization experiments 2.1 to 2.4 were carried out in a parallel pressure reactor, described in U.S. Pat. Nos. 6,306,658, 6,455,316 and 6,489,168, and WO 00/09255. Ethylene oligomerization experiment 2.5 was carried out in a parallel pressure reactor described in U.S. Pat. No. 6,759,014. All air-sensitive procedures were performed under a purified argon or nitrogen atmosphere in a Vacuum Atmospheres or MBraun glove box. All solvents used were anhydrous and de-oxygenated. All glassware and the disposable paddles were dried in a vacuum oven at 200° C. for at least 24 hours.

Xa. Stock Solution & Suspension Preparation
Preparation of the Group 13 Reagent and Activator Stock Solutions:

A 600 mM solution of Modified Methylaluminoxane-3A (MMAO-3A) in toluene was prepared by combining 5.10 mL of a 2.35 M solution of MMAO-3A in toluene (purchased from Akzo Chemical Inc., Chicago, Ill.) and 14.89 mL of toluene. The 200 mM and 300 mM solutions of MMAO-3A in toluene were prepared by further dilution of the 600 mM solution of MMAO-3A in toluene.

A 600 mM solution of MMAO in heptane was prepared by combining 6.60 mL of a 1.82 M solution of MMAO-3A in heptane (purchased from Akzo Chemical Inc., Chicago, Il) and 13.40 mL heptane. The 200 mM solution of MMAO-3A in heptane were prepared by further dilution of the 600 mM solution of MMAO-3A in heptane.

A 200 mM solution of TIBA (Triisobutylaluminum) in toluene was prepared by combining 1.59 g of neat Triisobutylaluminum (purchased from Aldrich, Milwaukee, Wis.) and 37.98 mL of toluene. The 50 mM solution of TIBA in toluene were prepared by further dilution of the 200 mM solution of TIBA in toluene.

The 2.5 mM solution of SJ2BF$_{20}$ (N,N-di(n-decyl)-4-n-butyl-anilinium tetrakis(perfluorophenyl)borate, [(4-n-Bu-C$_6$H$_4$)NH(n-decyl)$_2$]$^+$[B(C$_6$F$_5$)$_4$]$^-$) in toluene was prepared by dissolving 0.555 g of SJ2BF$_{20}$ in 20 mL of toluene.

Preparation of Toluene Slurry of Complex M1 for Example 2.1:

8.0 mg of Complex M1 and 2.68 mL of toluene were combined. A green colored slurry suspension was prepared by stirring the mixture vigorously for 3 hours at room temperature.

Preparation of Toluene Solution of Complex M2 for Example 2.2:

10.5 mg of Complex M2 was dissolved in 2.83 mL of toluene to give a clear, dark red colored 5 mM solution.

Preparation of Toluene Solution of Complex M2 for Examples 2.3 and 2.4:

10.3 mg of Complex M2 was dissolved in 2.78 mL of toluene to give a clear, dark red colored 5 mM solution.

Preparation of Heptane Slurry of Complex M2 for Example 2.5:

5.0 mg of Complex M2 and 2.70 mL heptane were combined. A beige colored slurry suspension was prepared by stirring the mixture vigorously for 5 hours at room temperature.

Xb. Reactor Preparation

A pre-weighed, pre-dried, glass vial insert and disposable stirring paddle were fitted to each reaction vessel of the reactor.

Example 2.1

Method A. The reactor was then closed, 0.100 mL of a 200 mM solution of MMAO-3A in toluene and 4.85 mL of toluene were injected into the pressure reaction vessel through a valve. The temperature was then set to 80° C., and the stirring speed was set to 800 rpm, and the mixture was exposed to ethylene at 100 psi (0.67 MPa) pressure. An ethylene pressure of 100 psi (0.67 MPa) in the pressure cell and the temperature setting were maintained, using computer control, until the end of the selective oligomerization experiment.

Example 2.2

Method B. The reactor was then closed, 0.100 mL of a 200 mM solution of MMAO-3A in heptane and 4.85 mL of heptane were injected into the pressure reaction vessel through a valve. The temperature was then set to 80° C., and the stirring speed was set to 800 rpm, and the mixture was exposed to ethylene at 100 psi (0.67 MPa) pressure. An ethylene pressure of 100 psi (0.67 MPa) in the pressure cell and the temperature setting were maintained, using computer control, until the end of the selective oligomerization experiment.

Example 2.3

Method C. The reactor was then closed, 0.100 mL of a 200 mM solution of MMAO-3A in toluene and 4.85 mL of toluene were injected into the pressure reaction vessel through a valve. The temperature was then set to 80° C., and the stirring speed was set to 800 rpm, and the mixture was exposed to ethylene at 100 psi (0.67 MPa) pressure. An ethylene pressure of 100 psi (0.67 MPa) in the pressure cell and the temperature setting were maintained, using computer control, until the end of the selective oligomerization experiment.

Example 2.4

Method D. The reactor was then closed, 0.200 mL of a 50 mM solution of TIBA in toluene and 4.85 mL of toluene were injected into the pressure reaction vessel through a valve. The temperature was then set to 80° C., and the stirring speed was set to 800 rpm, and the mixture was exposed to ethylene at 100 psi (0.67 MPa) pressure. An ethylene pressure of 100 psi (0.67 MPa) in the pressure cell and the temperature setting were maintained, using computer control, until the end of the selective oligomerization experiment.

Example 2.5

Method E. The reactor was then closed, 0.200 mL of a 200 mM solution of MMAO-3A in heptane and 3.36 mL of heptane were injected into the pressure reaction vessel through a valve. The temperature was then set to 80° C., and the stirring speed was set to 800 rpm, and the mixture was exposed to ethylene at 300 psi (2.0 MPa) pressure. An ethylene pressure of 300 psi (2.0 MPa) in the pressure cell and the temperature setting were maintained, using computer control, until the end of the selective oligomerization experiment.

Xc. Activation Methods and Injection of Solutions into the Pressure Reactor Vessel The following methods were employed to activate and inject the chromium-ligand compositions into the parallel pressure reactor. The examples are presented in Table X.

Example 2.1, Method AA: 333 μL of a 300 mM solution of MMAO in toluene was dispensed into a magnetically stirred 1 mL vial. About 30 seconds later, 100 μL of a rapidly stirred slurry suspension of Complex M2 (3.0 mg/ml slurry, equivalent to a concentration of 5 mM) was added. After approximately 9 minutes, 50 μL of toluene was added to the 1 mL vial. About another 30 seconds later, 121 μL of the vial contents was injected into the pre-pressurized reaction vessel and was followed immediately by injection of toluene (379 μL) to bring the total volume injected to 500 μL.

Example 2.2, Method BB: 400 μL of a 200 mM solution of MMAO-3A in heptane was dispensed into a magnetically stirred 1 mL vial. About 30 seconds later, 80 μL of the 5 mM solution of M2 in toluene was added. After approximately 60 seconds, 361 μL of the vial contents were injected into the pre-pressurized reaction vessel and was followed immediately by injection of heptane (639 μL) to bring the total volume injected to 1000 μL.

Example 2.3, Method CC: 400 μL of a 200 mM solution of MMAO-3A in toluene was dispensed into a magnetically stirred 1 mL vial. About 30 seconds later, 80 μL of the 5 mM solution of M2 in toluene was added. After approximately 60 seconds, 120 μL of the vial contents were injected into the pre-pressurized reaction vessel and was followed immediately by injection of toluene (380 μL) to bring the total volume injected to 500 μL.

Example 2.4, Method DD: 200 μL of 176 μL of a 2.5 mM solution of SJ2BF$_{20}$ (N,N-di(n-decyl)-4-n-butyl-anilinium tetrakis(perfluorophenyl)borate) in toluene was dispensed into a magnetically stirred 1 mL vial. About 30 seconds later, 80 μL of the 5 mM solution of M2 in toluene was added. After approximately 30 seconds, 200 μL of a 50 mM solution of TIBA in toluene was added to the 1 mL vial. About another 30 seconds later, 114 μL of the vial contents were injected into the pre-pressurized reaction vessel and was followed immediately by injection of toluene (386 μL) to bring the total volume injected to 500 μL.

Example 2.5, Method EE: 40 μL of a rapidly stirred slurry suspension of Complex M2 in heptane (1.85 mg/ml slurry, equivalent to a concentration of 2.5 mM) was aspirated from a 4 ml vial located on a magnetic stir plate, followed 5 seconds later by the aspiration of 80 μL of heptane, followed 3 seconds later by spraying the outside of the needle with heptane for 2 seconds, followed 6 seconds later by injection into the pre-pressurized reaction vessel, followed immediately by injection of heptane (480 μL) to bring the total volume injected to 500 μL.

Xd. Oligomerization Reactions

The trimerization reactions were allowed to continue for between 12 minutes and 48 minutes, during which time the temperature and pressure were maintained at their pre-set levels by computer control. The specific reaction times for each experiment are shown in Table X. After the reaction time elapsed, the reaction was quenched by addition of an overpressure of oxygen (approximately 40 psi (0.27 MPa) of a 20% $O_2$/80% $N_2$ mixture) sent to the reactor. The reaction times were the lesser of the maximum desired reaction time or the time taken for a predetermined amount of ethylene gas to be consumed in the reaction.

Xe. Product Analysis

After completion of the oligomerization reactions, the glass vial inserts containing the reaction products were removed from the pressure cell and removed from the inert atmosphere dry box, and deionized water (100 μL) was added. The glass vial inserts were then centrifuged for approximately 10 minutes. After centrifuging, 500 μL of the supernatant was then removed and analyzed by the GC-FID technique described above. The remaining supernatant was then decanted, and the vial insert containing insoluble residue was then placed in a centrifuge evaporator and the volatile components were removed. After most of the volatile components had evaporated, the vial contents were dried thoroughly (to constant weight) by evaporation at elevated temperature (approximately 80° C.) under reduced pressure in a vacuum oven. The vial was then weighed to determine the mass of solid product (final weight minus vial tare weight). The calculated mass of the catalyst and cocatalyst residue was then subtracted from the total mass to give the yield of polyethylene produced.

Table X presents the results from the ethylene oligomerization reactions performed in a 48-well parallel pressure reactor. In Table X, 1-hexene selectivity is shown as a percentage and is defined as 100×[micromoles of 1-hexene]/[sum of micromoles of $C_6$-$C_{16}$ olefins]. Catalyst activity (Turn Over Frequency, TOF) for production of the desired oligomer (1-hexene) is defined as the [micromoles of 1-hexene]/([micromoles of catalyst]*[reaction time in minutes]/60), as shown in the column "1-hexene TOF". In Table X, MMAO-3A is abbreviated to "MMAO".

TABLE Xa

| Example # | Externally Premixed Activators and mol equivalents versus Cr | Total Al/Cr molar ratio | Oligomerization Reaction Time (min) | μmol 1-hexene produced | 1-hexene Selectivity (%) | 1-hexene TOF (mol/mol * hour) | mg polyethylene produced |
|---|---|---|---|---|---|---|---|
| 2.1 | 200 MMAO | 360 | 47.8 | 4,390 | 96.9 | 44,200 | 5.9 |
| 2.2 | 200 MMAO | 267 | 45.1 | 3,960 | 96.6 | 17,600 | 2.2 |
| 2.3 | 200 MMAO | 400 | 22.8 | 4,700 | 97.3 | 123,000 | 1.8 |
| 2.4 | 1.1 SJ2BF$_{20}$/ 25 TIBA | 125 | 37.2 | 5,050 | 97.2 | 81,500 | 0.0 |
| 2.5 | N/A | 400 | 12.1 | 7,810 | 97.9 | 387,000 | 1.8 |

TABLE Xb

| Example # | Composition | Solvent | Reactor Temp (° C.) | Reactor Pressure (psi) | Group 13 reagent added to reactor | Group 13 reagent amount added to reactor (μmol) |
|---|---|---|---|---|---|---|
| 2.1 | M1 | Toluene | 80 | 100 | MMAO | 20 |
| 2.2 | M2 | Heptane | 80 | 100 | MMAO | 20 |
| 2.3 | M2 | Toluene | 80 | 100 | MMAO | 20 |
| 2.4 | M2 | Toluene | 80 | 100 | TIBA | 10 |
| 2.5 | M2 | Heptane | 80 | 300 | MMAO | 40 |

Rac/meso-1,2-Bis(chloro(diethylamino)phosphino)ethane

To a slightly hazy solution of 1,2-bis(dichlorophosphino)ethane (11.20 g, 48.3 mmol, 1.00 equiv.) in ether (250 mL) at −35 deg C. was added diethylamine (20.0 mL, 193 mmol, 4.00 equiv.) dropwise. The mixture quickly became thick with white precipitate. The reaction was allowed to warm to room temperature and stir 2 hours. The mixture was filtered, giving a white solid and a colorless solution. The solution was evaporated in vacuo, leaving a white solid that melted to a light yellow liquid at room temperature. Yield 14.68 g (100%). $^1$H NMR ($C_6D_6$): 0.84 (t, 12H, NCH$_2$CH$_3$), 2.14 (br s, 4H, CH$_2$CH$_2$), 2.83 (br m, 8H, NCH$_2$CH$_3$). {$^1$H}$^{31}$P NMR ($C_6D_6$): 147.7.

Rac/meso-1,2-Bis((diethylamino)phenylphosphino)ethane

To a hazy white solution of 1,2-bis(chloro(diethylamino)phosphino)ethane (2.00 g, 6.55 mmol, 1.00 equiv.) in ether (20 mL) at −35 deg. C. was added a solution of phenyllithium (1.10 g, 13.1 mmol, 2.00 equiv.) in ether (10 mL) dropwise. The reaction turned light yellow on adding phenyllithium, and precipitate formed after one half the phenyllithium was added. The reaction was allowed to warm to room temperature and stir 17 hours. The mixture was then was evaporated in vacuo, leaving an oily residue. The residue was extracted with pentane (20 mL, then 2×10 mL), and the extracts filtered to give a white solid and a yellow solution. The solution was evaporated in vacuo, leaving a yellow solid that melted to a yellow liquid at room temperature. Yield 2.47 g (97%). $^1$H NMR ($C_6D_6$): 0.95 (t, 12H, NCH$_2$CH$_3$), 2.06-2.32 (m, 4H, CH$_2$CH$_2$), 2.87-3.01 (br m, 8H, NCH$_2$CH$_3$), 7.08-7.20 (m, 6H, phenyl), 7.50-7.53 (m, 4H, phenyl). {$^1$H}$^{31}$P NMR ($C_6D_6$): 59.8 and 61.2.

Rac/meso-1,2-Bis(chlorophenylphosphino)ethane

To a yellow solution of 1,2-bis((diethylamino)phenylphosphino)ethane (2.42 g, 6.23 mmol, 1.00 equiv.) in ether (30 mL) at −35 deg. C. was rapidly added a 1.0 M solution of HCl in ether (30 mL, 30 mmol, 4.82 equiv.). The reaction turned white with much precipitate on adding HCl. The reaction was allowed to warm to room temperature and stir 50 minutes. The mixture was then filtered to give a white solid and a colorless solution. The solution was evaporated in vacuo, leaving a white solid. Yield 1.82 g (93%). $^1$H NMR ($C_6D_6$): 2.06 (br, 4H, CH$_2$CH$_2$), 6.96-7.00 (m, 6H, phenyl), 7.34-7.41 (m, 4H, phenyl). {1H} 31P NMR (C6D6): 92.5 and 93.0.

Rac/meso-1,2-Bis((2-methoxyphenyl)phenylphosphino)ethane

To a slightly cloudy solution of 1,2-bis(chlorophenylphosphino)ethane (1.78 g, 5.65 mmol, 1.00 equiv.) in ether (30 mL) at −35 deg. C. was added a solution of 2-methoxyphenyllithium (1.29 g, 11.3 mmol, 2.00 equiv.) in ether (10 mL) dropwise. White precipitate formed after one half of the 2-methoxyphenyllithium was added. The reaction turned yellow at the end of the addition. The mixture was allowed to warm to room temperature and stir 21 hours. The reaction was then evaporated in vacuo, leaving a white solid. The residue was extracted with ether (4×20 mL)), and the extracts filtered to give an off-white solid and a colorless solution. The solution was evaporated in vacuo, leaving white solid. Yield 2.48 g (96%). $^1$HNMR ($C_6D_6$): 2.22-2.60 (m, 4H, CH$_2$CH$_2$), 3.11 (s, 3H, OMe), 3.14 (s, 3H, OMe), 6.40 (d, 2H, aromatic H), 6.72 (t, 2H, aromatic H), 7.01-7.11 (m, 10H, aromatic H), 7.44-7.50 (m, 4H, aromatic H). {$^1$H}$^{31}$P NMR ($C_6D_6$): −19.9 and −20.2.

As discussed herein, catalytic performance can be determined a number of different ways, as those of skill in the art will appreciate. Catalytic performance can be determined by the yield of oligomer (for example, trimer or tetramer) obtained per mole of metal complex, which in some contexts may be considered as activity.

The results of selective ethylene trimerization or tetramerization using ligands of the invention in combination with chromium precursors or with isolated chromium metal complexes are surprising. The results illustrate that certain combinations are more productive in the trimerization of ethylene, for example, to produce 1-hexene at a higher selectivity and a lower selectivity toward polyethylene when compared with other chromium-ligand catalysts under similar conditions.

All documents described herein are incorporated by reference herein, including any priority documents and/or testing procedures. As is apparent from the foregoing general description and the specific embodiments, while forms of the invention have been illustrated and described, various modifications can be made without departing from the spirit and scope of the invention. Accordingly, it is not intended that the invention be limited thereby.

What is claimed is:

1. A method to selectively oligomerize an olefin comprising contacting the olefin with a composition comprising:

1) at least one ligand characterized by the general formula:

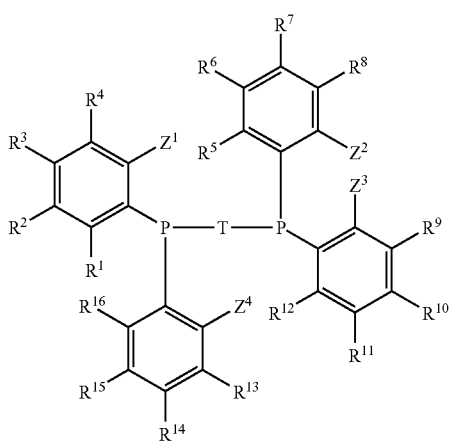

wherein

P is phosphorus;
each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$ is independently, selected from the group consisting of hydrogen, halogen, optionally substituted hydrocarbyl and optionally substituted heteroatom containing hydrocarbyl;
each of $Z^1$, $Z^2$, $Z^3$, and $Z^4$ is, independently, selected from a first group consisting of hydrogen, a hydrocarbyl, alkoxy, aryloxy, alkylthio, arylthio, hydroxyl, mercapto and amino;
T is a bridging group selected from the group consisting of optionally substituted hydrocarbyl having from 1 to 20 carbon atoms;

2) a metal precursor characterized by the general formula $Cr(L)_n$ where each L is independently selected from the group consisting of, mesityl, tetrahydrofuran, methyl, ethyl, butyl, pentyl, hexyl, octyl, phenyl, $Et_2O$, $NH_3$, $NMe_3$, acetylacetonate, 2-ethylhexanoate, neopentyl, $SMe_2$, $CH_2—C_6H_4$-o-$NMe_2$, trifluoroacetate, $CH(SiMe_3)_2$, diisopropylamide, picolinate, or $NO_3$, where Et is ethyl and Me is methyl, and wherein two or more L groups may be combined in a ring structure having from 3 to 50 non-hydrogen atoms; n is 3, 4, 5, or 6; and 3) optionally, one or more activators, and wherein at least two and less than all four of $Z^1$, $Z^2$, $Z^3$, and $Z^4$ are selected from a second group consisting of alkoxy, aryloxy, alkylthio, arylthio, hydroxyl, mercapto, and amino, and $Z^1$, $Z^2$, $Z^3$, and $Z^4$ may not all be methoxy, and either of the pairs of $Z^1$ and $Z^2$ or $Z^3$ and $Z^4$ are not both selected from the second group, wherein either both of $Z^2$ and $Z^3$ or both of $Z^1$ and $Z^4$ are selected from the second group.

2. The method of claim 1, wherein T has from 2 to 16 carbon atoms.

3. The method of claim 2, wherein T is selected from the group consisting of ethyl, propyl, butyl, pentyl, hexyl, cyclohexyl, aryl, heptyl, tolyl, octyl, nonyl, decyl, phenyl, naphthyl, and dodecyl.

4. The method of claim 1, wherein each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$ is independently, selected from the group consisting of hydrogen, a hydrocarbyl group having 1 to 20 carbon atoms, a substituted hydrocarbyl group having 1 to 20 carbon atoms and halogen.

5. The method of claim 1, wherein each of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, and $R^{16}$ is independently, selected from the group consisting of hydrogen or a $C_1$ to $C_{20}$ hydrocarbyl or substituted $C_1$ to $C_{20}$ hydrocarbyl.

6. The method of claim 1, wherein each of $Z^1$, $Z^2$, $Z^3$, and $Z^4$ is, independently, hydrogen, alkoxy, aryloxy, alkylthio, arylthio, hydroxyl, mercapto, amino, with the alkyl or aryl or substituents on these groups are a $C_1$ to $C_{20}$ hydrocarbyl group.

7. The method of claim 6, wherein the $C_1$ to $C_{20}$ hydrocarbyl group is selected from the group consisting of methyl, ethyl, propyl, butyl, pentyl, hexyl, cyclohexyl, aryl, heptyl, tolyl, octyl, nonyl, decyl, phenyl, napthyl, benzyl, tolyl, or dodecyl.

8. The method of claim 1, wherein the metal precursor is selected from the group consisting of $Cr(mes)_3(THF)$, $Cr(TFA)_2(Et_2O)_2$ and $CrPh_3(THF)_3$, wherein THF is tetrahydrofuran, mes is mesityl, Et is ethyl, TFA is trifluoroacetate and Ph is phenyl.

9. The method of claim 1, wherein three of $Z^1$, $Z^2$, $Z^3$, and $Z^4$ are selected from the group consisting of alkoxy, aryloxy, alkylthio, arylthio, hydroxyl, mercapto, and amino.

10. The method of claim 1, wherein at least two and less than all four of $Z^1$, $Z^2$, $Z^3$, and $Z^4$ is selected from the group consisting of aryloxy, alkylthio, arylthio, hydroxyl, mercapto, and amino.

11. The method of claim 1, wherein the ligand is characterized by the general formula:

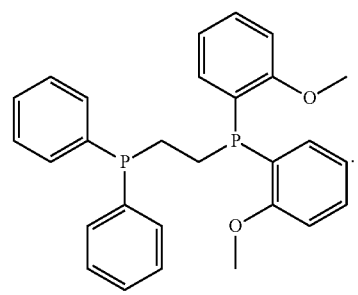

A3

12. The method of claim 1, wherein the ligand comprises $Ar_2PCH_2CH_2P(2\text{-MeOPh})_2$, wherein Ar is arene, Me is methyl, Ph is phenyl.

13. The method claim 1, wherein the metal precursor is selected from the group consisting of $(Mes)_3Cr(THF)$, $[\{TFA\}_2Cr(OEt_2)]_2$, $(THF)_3CrPh_3$, $Cr(acac)_2Ph$, $Cr(acac)_2Me$, $Cr(acac)_3$, $Cr(2\text{-ethylhexanoate})_3$, $Cr(neopentyl)_4$, $Cr(CH_2—C_6H_4\text{-o-NMe}_2)_3$, $Cr(TFA)_3$, $Cr(CH(SiMe_3)_2)_3$, Cr(Mes)$_2$(THF)$_3$, Cr(Mes)$_2$(THF), Cr(diisopropylamide)$_3$, Cr(picolinate)$_3$, [Cr$_2$Me$_8$][Li(THF)]$_4$, Cr(NO$_3$)$_3$, [CrMe$_6$][Li (Et$_2$O)]$_3$, [CrPh$_6$][Li(THF)]$_3$, [CrPh$_6$][Li(n-Bu$_2$O)]$_3$, [Cr (C$_4$H$_8$)$_3$][Li(THF)]$_3$, and mixtures thereof, where THF is tetrahydrofuran, Me is methyl, Et is ethyl, Mes is mesityl (2,4,6-trimethyl phenyl), TFA is trifluoroacetate, acac is acetylacetonate, Ph is phenyl, and n-Bu is n-butyl.

14. The method claim 1, wherein the metal precursor is selected from the group consisting of (Mes)$_3$Cr(THF), Cr$_2$(TFA)$_4$(Et$_2$O)$_2$, (THF)$_3$CrPh$_3$, and mixtures thereof, where THF is tetrahydrofuran, Me is methyl, Et is ethyl, Mes is mesityl (2,4,6-trimethyl phenyl), TFA is trifluoroacetate, and Ph is phenyl.

15. The method claim 1, wherein the ligand to metal precursor compound ratio is in the range of about 0.01:1 to about 100:1.

16. The method claim 1, wherein the activator is selected from the group consisting of modified methylalumoxane (MMAO), methylalumoxane (MAO), trimethylaluminum (TMA), triisobutyl aluminum (TIBA), polymethylalumoxane-IP (PMAO), N,N-di(n-decyl)-4-n-butyl-anilinium, tetrakis(perfluorophenyl)borate, BF$_{15}$ (tris(pentafluororphenyl)borane), and mixtures thereof.

17. The method claim 1, wherein the olefin is a C$_2$ to C$_{12}$ olefin.

18. The method of claim 17, wherein the olefin is a C$_2$ to C$_8$ olefin.

19. The method of claim 18, wherein the olefin is ethylene.

20. The method claim 1, wherein the process produces a trimer or a tetramer of the olefin.

21. The method of claim 19, wherein the process produces 1-hexene.

22. The method of claim 19, wherein the process produces 1-octene.

23. The method of claim 19, wherein the process produces a mixture of 1-hexene and 1-octene.

24. The method of claim 1, wherein the reaction occurs in a hydrocarbon solvent.

25. The method of claim 1, wherein the method produces at least 70% selectivity for the desired oligomer(s), calculated based upon the amount of the desired oligomer produced relative to the total yield; and at least 70% of the olefin monomer reacts to form product.

* * * * *